United States Patent [19]

Fisher et al.

[11] Patent Number: 5,420,027

[45] Date of Patent: May 30, 1995

[54] METHODS AND COMPOSITIONS FOR THE EXPRESSION OF BIOLOGICALLY ACTIVE FUSION PROTEINS COMPRISING A EUKARYOTIC CYTOCHROME P450 FUSED TO A REDUCTASE IN BACTERIA

[75] Inventors: Charles W. Fisher, Dallas, Tex.; Henry J. Barnes, Chula Vista, Calif.; Ronald W. Estabrook, Dallas, Tex.

[73] Assignee: Board of Regents, The University of Texas System, Austin, Tex.

[21] Appl. No.: 908,317

[22] Filed: Jul. 2, 1992

Related U.S. Application Data

[63] Continuation of Ser. No. 640,473, Jan. 10, 1991, Pat. No. 5,240,831.

[51] Int. Cl.$^6$ .................. C12N 9/02; C12N 15/53; C12N 15/62; C12N 15/63
[52] U.S. Cl. .................. 435/189; 435/69.7; 435/252.3; 435/252.33; 435/320.1; 536/23.4; 536/23.2; 935/10; 935/14; 935/27; 935/38; 935/44; 935/47
[58] Field of Search .................. 435/69.1, 69.7, 189, 435/252.3, 252.33, 320.1; 536/23.2, 23.4

[56] References Cited

U.S. PATENT DOCUMENTS

| | | | |
|---|---|---|---|
| 4,766,068 | 8/1988 | Oeda et al. | 435/68 |
| 4,910,141 | 3/1990 | Wong et al. | 435/172.3 |
| 5,045,471 | 9/1991 | Miller | 435/320.1 |
| 5,073,627 | 12/1991 | Curtis et al. | 530/351 |

FOREIGN PATENT DOCUMENTS

| | | | |
|---|---|---|---|
| 0360361 | 3/1990 | European Pat. Off. | 435/252.3 |
| WO89/10961 | 11/1989 | WIPO | 435/172.3 |
| 91/03561 | 3/1991 | WIPO | 435/184 |

OTHER PUBLICATIONS

White, P. C. et al., 1984, Proceedings of the National Academy of Sciences, USA, 81: 1986–1990.
Evans, L. T. et al., 1986, Proceedings of the National Academy of Sciences, USA, 83: 6387–6391.
Narhi, L. O. et al., 1988, Molecular and Cellular Biochemistry, 79: 63–71.
Porter, T. P. et al., 1987, Archives of Biochemistry and Biophysics, 254(1): 353–367.
Mittal, S., et al., 1988, Archives of Biochemistry and Biophysics, 264(2): 383–391.
Koga, H., et al., 1985, Biiochemical and Biophysical Research Communications, 130(1): 412–417.
Murakami, H., et al., 1987, DNA, 6(3): 189–197.
Higuchi, R., et al., 1988, Nucleic Acids Research, 20(12):3127–3133.
Bücheler, U. W., et al., 1990, Gene, 96(2): 271–276.
Bücheler, U. W., et al., 1992, Nucleic Acids Research, 20(12): 3127–3133.
Lawson, J. R., et al., 1991, Journal of Biological Chemistry 266(12): 7321–7324.
Li, Y. L., et al., 1991, Journal of Biological Chemistry 266(29): 19186–19191.
Huston, J. S., et al., 1988, Proceedings of the National Academy of Sciences, USA, 85: 5879–5883.

(List continued on next page.)

Primary Examiner—Robert A. Wax
Assistant Examiner—William W. Moore
Attorney, Agent, or Firm—Arnold, White & Durkee

[57] ABSTRACT

Disclosed are methods and compositions for effecting bacterial expression of eukaryotic cytochrome P450 enzymes and fusion proteins comprising a eukaryotic P450 domain fused to a reductase enzyme domain in a biologically active form. Certain embodiments involve the expression of eukaryotic cytochrome P450$_{17\alpha}$-hydroxylase which is expressed in large amounts in an E. coli host in a biologically active form without the need for coexpression or admixture of a cytochrome P450 reductase. Methods and compositions are also disclosed for the construction of cytochrome P450 enzyme hybrids or fusion proteins, incorporating the N-terminal 9 amino acids from bovine 17α-hydroxylase, which will enable many eukaryotic cytochrome P450 enzymes or fusion proteins to be expressed in bacteria.

49 Claims, 13 Drawing Sheets

```
19   M V L E M L N P I H Y N I T S I V P E A M P A A T M P V L L L T G L F L L V W
21                                               M V L A G L L L L L L T L L S G A H L
1A1                                        M L F P I S M S A T E F L L A S V I F C L V
1A2                                  M A L S Q S V P F S A T E L L L A S A I F C L V
2C8                                              M E P F V V L V L C L S F M L L F S L
3A4                                  M A L I P X L A M E T W L L L A V S L V L L Y
17A1                                                       M W L L L A V F L
```

OTHER PUBLICATIONS

Coghlan, V. M., et al., 1991, Journal of Biological Chemistry, 266(28): 18606–18612.

Brandt, M. E., et al, 1992, Archives of Biochemistry and Biophysics, 294(2): 735–740.

Old, S. E., et al., 1990, Proceedings of the National Academy of Sciences, USA, 87: 4942–4945.

Citron, B. A., et al., 1990, Proceedings of the National Academy of Sciences, USA, 87: 6436–6440.

Hyde, G. E., et al., 1990, Biochemical and Biophysical Research Communications, 168(3): 1285–1291.

Pharmacia, Inc., products catalogue, 1984, p. 63.

Argos, Patrick, "An Investigation of Oligopeptides Linking Domains in Protein Tertiary Structures and Possible Candidates for General Gene Fusion," *J. Mol. Biol.*, 211:943–958, 1990.

Harada et al., "Structural Characterization of the Human Estrogen Synthetase (Aromatase) Gene," *Biochem. Biophys. Res. Commun.*, 166(1): 365–372, 1990.

Kilgore et al., "Alternative Promotion of Aromatase P–450 Expression in the Human Placenta," *Mol. Cel. Endocrinol.* 83:R9–R16, 1992.

Mahendroo et al., "Tissue-specific Expression of Human P-450$_{AROM}$," *J. Biol. Chem.*, 266(17): 11276–11281, 1991.

Means et al., "Tissue-specific Promoters Regulate Aromatase Cytochrome P450 Gene Expression in Human Ovary and Fetal Tissues," *Mol. Endocrin.*, 5:2005–2013, 1991.

Means et al., "Structural Analysis of the Gene Encoding Human Aromatase Cytochrome P–450, the Enzyme Responsible for Estrogen Biosynthesis," *J. Biol. Chem.*, 264(32): 19385–19391, 1989.

Sakaki et al., "Expression of Bovine Cytochrome P450c21 and Its Fused Enzymes with Yeast NADPH–Cytochrome P450 Reductase in *Saccharomyces cerevisiae*," *DNA and Cell Biology*, 9(8): 603–614, 1990.

Shibata et al., "Genetically Engineered P450 Monooxygenases: Construction of Bovine P450c17/Yeast Reductase Fused Enzymes," *DNA and Cell Biology*, 9(1): 27–36, 1990.

Simpson et al., "Tissue-Specific Promoters Regulate Aromatase Cytochrome P450 Expression," *Clin. Chem.*, 39(2): 317–324, 1993.

Simpson et al., "Regulation of Human Aromatase Cytochrome P450 Gene Expression," *J. Steroid Biochem. Molec. Biol.*, 43(8): 923–930, 1992.

Simpson et al., "Regulation of Expression of the Genes Encoding Steroidogenic Enzymes," *J. Steroid Biochem. Molec. Biol.*, 40(1–3): 45–52, 1991.

Toda et al., "Characterization of a cis-acting Regulatory Element Involved in Human-Aromatase P–450 Gene Expression," *Eur. J. Biochem.*, 205:303–309, 1992.

Toda et al., "Structural and Functional Characterization of Human Aromatase P-450 Gene", *Eur. J. Biochem.*, 193: 559–565, 1990.

Wang, Jinfa and Chen, Shiuan, "Identification of a Promoter an a Silencer at the 3'-End of the First Intron of the Human Aromatase Gene," *Mol. Endocrin.*, 6:1479–1488, 1992.

Zhou et al., "Stable Expression of Human Aromatase Complementary DNA in Mammalian Cells: A Useful System for Aromatase Inhibitor Screening," *Cancer Res.*, 50:6949–6954, 1990.

International Search Report, Mailed Oct. 20, 1993, for International Patent Application No. PCT/US95/06171.

Porter et al., Proceedings of the VIIIth International Symposium on Microsomes and Drug Oxidations, Karolinska Institutet, Stockholm, Jun. 25–29, 1990, Eds. M. Ingelman-Sundberg, J-A. Gustafsson, S. Orrenius, Abstract L–35.

Feyereisen et al, PNAS, 86:1465–1469, 1989.

Andersson et al., J Bio Chem, 264(14):8222–8229, 1989.

Cullin and Pompon, Gene, 65:203–217, 1988.

Corbin et al., PNAS, 85:8948–8952, 1988.

Hardwick et al., J Biol Chem, 262(2):801–810, 1987.

Chua et al., PNAS, 84:7193–7197, 1987.

Zuber et al., J Biol Chem, 261(5):2475–2482, 1986.

Yoshioka et al., J Biol Chem, 261(9):4106–4109, 1986.

Gonzalez et al., J Bio Chem, 260(12):7435–7441, 1985.

Morohashi et al., PNAS, 81:4647–4651, 1984.

Yabusaki et al., Nuc Acid Res, 12(6):2929–2938, 1986.

Fujii-Kuriyama et al., PNAS, 79:2793–2797, 1982.

McCarthy and Gualerzi, Trends Genetics, 6(3):78–85, 1990.

Gold and Stormo, Methods in Enzymology, 185:89–93, 1990.

DeBoer and Hui, Methods in Enzymology, 185:103–114, 1990.

Chen and Inouye, Nucl Acid Res, 18(6):1465–1473, 1990.

Gold and Stormo, '*E. coli* and *Salmonella typhimerium* Cellular and Molecular Biology', American Society for Microbiology, Washington, D.C., Ed. F. C. Weidhardt, 1987, pp. 1302–1307.

(List continued on next page.)

OTHER PUBLICATIONS

Bachmair et al., Science, 234:179–, 1988. (Abstract only).
Gren, Biochimie, 66:1–29, 1984.
Stormo et al., Nucl Acid Res, 10(9):2971–2975, 1982.
Platt, Ann Rev Biochem, 55:339–372, 1986.
Hawley and McClure, Nucl Acid Res, 11(8):2237–2255, 1983.
Rosenberg and Court, Ann Rev Genet, 13:319–353, 1979.
Kawasaki, PCR Protocols: A Guide to Methods and Applications, Academic Press, Inc., 1990, pp. 21–27.
Hu & Chung, Mol. Endocrinology, 4(6):893–989, 1990).
Omer et al., J. Bacteriol., 172(6):3335–3345, 1990.
Imai et al., PNAS, 86:7823–7827, 1989.
Wen & Fulco, J. Biol. Chem., 262(14):6676–6682, 1989.
Unger et al., J. Biol. Chem., 26193:1158–1163, 1986.
Tobias et al., Science, 254, 1374–1377, 1991.
Schein, Current Opinion in Biotechnology, 2:746–750, 1991.
Gottesman, Methods in Enzymology, 185:119–129, 1990.
Kopetzki et al., Mol. Gen. Genet., 216:149–155, 1989.
Kulisch & Vilker, Biotechnol. Prog., 7:93–98, 1991.
Ohkawa et al., Ann. N.Y. Acad. Sci., 613:37–43, 1990.
Halpert et al., Biochem. Pharmacol., 37(15):3046–3048, 1988.
Zuber et al., PNAS, 85:699–703, 1988.
Megges et al., in Molecular Mechanisms of Adrenal Steroidogenesis and Aspects of Regulation and Application, K. Ruckpaul & H. Rein, Eds., Akademie-Verlag, Berlin, 1990, pp. 204–209.
Richardson & Johnson, Gordon Research Conference on Drug Metabolism, 15–19 Jul., 1991, Plymouth, N.H.
Gijutsuin, Kogyo, and Ooeda, Kenji, "Expression Plasmid Aiming at Expression of Rat Hepatic Cytochrome P–450MC Gene in Escherichia Coli," Patent Abstracts of Japan, 10(144) (C–349) [2201], 1986, JP, A, 615783.
Nebert, D. W. et al., "The P450 Superfamily: Updated Listing of All Genes and Recommended Nomenclature for the Chromosomal Loci," DNA, 8(1):1–13, 1989.
Porter, T. D. et al., "Expression of Mammalian P450s in Escherichia Coli," Methods in Enzymology, 206:108–116, 1991.
Wada, A. et al., "Expression of Functional Bovine Cholesterol Side Chain Cleavage Cytochrome P450 (P450scc) in Escherichia coli," Archives of Biochemistry and Biophysics, 290(2): 376–380, 1991.
Aoyama, T. et al., "Estradiol Metabolism by Complementary Deoxyribonucleic Acid–Expressed Human Cytochrome P450s," Chemical Abstracts, 113(7):79, abstract No. 52701a, 1990.
Barnes, H. J. et al., "Evaluation of Various Expression Systems for the Synthesis of Cytochrome P–45017a," Journal of Cell Biology, 107 (6 part 3):196A, abstract No. 1118, 1988.
Swart. P. et al., "The Catalytic Activity of Human and Bovine Adrenal Cytochromes P45017a," Journal of Cell Biology, 107 (6 part 3):196A, abstract No. 1120, 1988.
Barnes, H. J. et al., "Expression and Enzymatic Activity of Recombinant Cytochrome P450 17 α-Hydroxylase in Escherichia coli," Proceedings of the National Academy of Sciences of USA, 88:5597–5601, 1991.
Fischer, C. W. et al., "High–Level Expression of Functional Human Cytochrome P450 1A2 in Escherichia coli," The FASEB Journal, 6(2):759–764, 1992.
Looman, A. C. et al., "Influence of the Codon Following the AUG Initiation Codon on the Expression of a Modified lacZ Gene in Escherichia coli," The EMBO Journal, 6(8):2489–2492, 1987.
Fisher et al., High–level expression in Escherichia coli of enzymatically active fusion proteins containing the domains of mammalian cytochromes P450 and NADPA–P450 reductase flavoprotein, Proc. Natl. Acad. Sci. USA, 89:10817–10821, 1992.
Shet, M. and Estabrook, R. W., Purification and Characterization of an NADPH–Cytochrome P450 (Cytochrome C) Reductase from Higher Plant Microsomes, 75th Annual Meeting of the Federation of American Societies of Xperimental Biology, FASEB J., 5(6):A1516, 1991.
Strobel et al., Cytochrome P–450: Cytochrome P–450 Reductase Interactions, Drug Metabolism Reviews, 20(2–4):519–533, 1989.
Yabusaki et al., Functional analysis of microsomal P450 monooxygenases by construction of P450/reductase fused enzymes, Protein Engineering, 3(4):365, 1990.
Yoshiyasu et al., Genetically Engineered Modification of P450 Monooxygenases: Functional Analysis of the Amino–Terminal Hydrophobic Region and Hinge Region of the P450/Reductase Fused Enzyme, DNA, 7(10):701–711, 1988.

```
        ATG TGG CTG CTC CTG GCT GTC TTT  ...
nat17   Met Trp Leu Leu Leu Ala Val Phe  ...

ATG GCT CTG TTA TTA GCA GTT TTT  ...
mod17   Met Ala Leu Leu Leu Ala Val Phe  ...
```

```
       509           57
        |            |
   GlySerThrProSerThrIleGlnThr
   GGTAGCACCCCGTCGACTATCCAAACA
             Sal I
```

```
       509           57
        |            |
   LysLysLeuHisSerThrIleGlnThr
   GGTAGCACCCCCTCGACTATCCAAACA
           Sal I°/Xho I°
```

FIG.8

```
      Bovine 17A1                    Rat 4A1
                                23  24  25  26  27
Met Ala Leu Leu Leu Ala Val Phe Leu Gly Leu Leu Leu Leu
ATG GCT CTG TTA TTA GCA GTT TTT CTG GTT CTG CTG CTG GTC
```

FIG.9

METHODS AND COMPOSITIONS FOR THE EXPRESSION OF BIOLOGICALLY ACTIVE FUSION PROTEINS COMPRISING A EUKARYOTIC CYTOCHROME P450 FUSED TO A REDUCTASE IN BACTERIA

The U.S. government may own certain rights in the present invention pursuant to NIH grant GM37942.

The present application is a continuation in part of Patent Cooperation Treaty application Ser. No. US92/00168 filed 10 Jan., 1992, which is a continuation in part of U.S. Ser. No. 07/640,473, filed 10 Jan., 1991, now U.S. Pat. No. 5,240,831.

BACKGROUND OF THE INVENTION

1. Field of the Invention

The present invention relates to the functional expression of eukaryotic cytochrome P450 enzymes, P450 enzyme hybrids, and fusion proteins comprising a eukaryotic cytochrome P450 domain fused to a reductase domain in bacterial cells, genetic constructs for effecting such expression, and methods employing these bacteria and/or the recombinant enzymes, P450 enzyme hybrids or fusion proteins so produced, e.g., as bioreactors for effecting the metabolism of cytochrome P450 substrates.

2. Description of the Related Art

The cytochrome P450 superfamily includes multiple molecular forms of enzymes which catalyze monooxygenase reactions of a wide variety of endogenous as well as exogenous substrates (Lu, et al., 1980). Each form of these hemoproteins exhibits a unique substrate specificity. The cytochrome P450 superfamily of enzymes participate, for example, in the metabolism of steroids (Hall, 1980), eicosanoid, fatty acids (Kupfer, 1980), and bile acids (Hansson and Wikvall, 1980), as well as exogenous substrates such as drugs, insecticides, and chemical carcinogens (Gelboin, 1980). Comparison of several forms of cytochrome P450 whose primary structures have so far been reported indicates that they are structurally related to one another and possibly derived from a common ancestor (Gotoh, et al, 1983).

Microsomal cytochrome P450s are integral membrane hemoproteins which derive reducing equivalents from NADPH by means of a membrane bound flavoprotein oxido-reductase (NADPH-cytochrome P450 reductase). These so-called mixed-function oxidases activate molecular oxygen so as to insert one atom into a lipophilic substrate and the other atom into water. Cytochrome P450 and P450-like enzymes are ubiquitous in nature, being found in a broad range of eukaryotes as well as bacteria. In fact, many of the bacterial enzymes are similar to a certain degree to the P450 enzymes found in mammals. For example, in certain soil bacteria (i.e., *Pseudomonas putida*), the oxygenation of camphor involves an enzyme termed cytochrome P450$_{CAM}$ which acts in concert with an FAD-containing flavoprotein, putida redoxin reductase and an iron sulfur protein putida redoxin. (Katagira, et al., 1968). Interestingly, the bacterial electron transfer system in *P. putida* is very similar to the one functional in the mitochondria of higher organisms. However, the electron transfer system of *P. putida* cannot support the functional transfer of electrons to either mitochondrial or microsomal P450s. Because of sequence similarities between the medically important mammalian microsomal P450 (Family IV) and the bacterial fatty acid monooxygenase from *Bacillus megaterium* (cytochrome P450$_{BM-3}$), a large amount of effort has been expended in characterizing this and other bacterial enzymes.

Although a certain amount of research has been directed towards the characterization of bacterial cytochrome P450s, their use in commercial applications, such as in bioreactors, chemical degradation and drug synthesis, is quite limited. The primary reason for this is that the number of specific forms of bacterial P450s that have been well characterized is very small and the reactions that these enzymes catalyze are of limited biomedical or commercial value.

In contrast, a vast number of eukaryotic and mammalian P450s have been characterized. These enzymes catalyze important reactions involved in drug, steroid and xenobiotic metabolism, all of which have a direct impact on human health. For example, cytochrome P450 1A2 is of great importance as it plays a critical role in the metabolism of (a) a number of aromatic amines; (b) the natural food constituent caffeine; (c) the sex hormone estradiol; and (d) certain drugs, including phenacetin. The N-oxidation of arylamines, also catalyzed by P450 1A2, is considered to be a primary activation step for the formation of reactive metabolites that have carcinogenic potential (Aoyama et al., 1989; McManus et al., 1990). Furthermore, this P450 is of interest because it is induced by agents such as polycyclic aromatic hydrocarbons, side-stream cigarette smoke, and heterocyclic amines formed during the charbroiling of meat (Sesardic et al., 1990).

Enzymatically active human P450s, if available, would also be of use in predicting the metabolites likely to be produced in humans in vivo, and in the isolation and structural determination of such metabolites. Current animal models for toxicology depend upon the assumption that metabolites produced in the experimental animal are the same as those produced in humans. The ability to produce large quantities of human P450 metabolites would allow the direct testing of these metabolites in cell culture or other mutagenic assays. For example, the catechol estrogens are proposed to play a role in the initiation of carcinogenesis. Their ability to undergo oxidation-reduction cycling, with the associated formation of radical intermediates, including superoxide, makes the understanding of their formation of central importance.

Unfortunately, present eukaryotic systems for the production of eukaryotic cytochrome P450s are hampered by several serious drawbacks including low rates of production, the use of expensive tissue culture materials and facilities as well as the requirement for sophisticated methodologies, and extensive destruction of the enzyme by the expression host or even lack of biological activity.

Clearly, a method for the increased production of eukaryotic cytochrome P450s would provide many benefits, both in basic research and in further applications, for example, in the metabolism of drugs and other molecules of importance to human health. It is therefore very unfortunate that eukaryotic cytochrome P450s have, to date, been found to be unsuitable for expression in bacterial systems, which usually offer many advantages over expression in yeast and mammalian cells, such as the high-level, low-cost production of proteins with considerable ease.

Accordingly, there is a great need for the development of technology which would allow the many advantages of bacterial expression systems to be used for the production of eukaryotic and mammalian cytochrome P450s. Although bacteria have demonstrated great utility in the expression of many prokaryotic and eukaryotic proteins, bacterial expression systems for cytochrome P450 have heretofore been limited to the soluble bacterial forms of this gene superfamily (Unger et al., 1986). Although yeast (Oeda et al., 1985), COS 1 (Zuber et al., 1986) and virally infected eukaryotic cells (Battula et al., 1987; Asseffa et al., 1989) have been used as hosts for the heterologous expression of P450 molecules, each has limitations to their usefulness as expression systems. Unfortunately, the present understanding in the art is that eukaryotic cytochrome P450s simply cannot be expressed functionally in bacteria (Cullin, et al., 1988).

Due to the existence of numerous disadvantages with current systems for the expression of biologically active cytochrome P450s, there exists a continuing need for the development of novel systems, particularly bacterial expression systems, which can be used to produce biologically active cytochrome P450 enzymes. There is a particular need for bacterial expression systems for expressing biologically active eukaryotic cytochrome P450s which incorporate the advantages of bacterial expression. The development of novel technology which addresses one or more of these disadvantages would have broad research and commercial applications including steroid and prostaglandin biosynthesis, as bioreactors, in drug development and characterization, and even in environmental remediation.

SUMMARY OF THE INVENTION

The present invention addresses various of the foregoing and other disadvantages in the art by providing for the first time methods and compositions for the expression of biologically active eukaryotic cytochrome P450 enzymes and P450 enzyme hybrids in bacterial systems. In general, the present invention concerns stably transformed bacterial cells which express a biologically active eukaryotic cytochrome P450 enzyme or enzyme hybrid, methods for the production of biologically active cytochrome P450 enzymes and P450 enzyme hybrids in recombinant bacteria, methods for the metabolism of cytochrome P450 substrates in such bacteria, DNA segments encoding eukaryotic cytochrome P450 enzymes and hybrids which have been modified to allow effective bacterial expression, as well as methods for obtaining bacterial expression of a biologically active eukaryotic cytochrome P450 enzyme or P450 enzyme hybrid.

The present invention is also directed to embodiments comprising "fusion proteins." Generally, a fusion protein comprises a domain exhibiting P450 enzyme activity fused to a domain which exhibits reductase activity. The P450 and reductase domains of a fusion protein need comprise only those regions of the native P450 enzyme or reductase enzyme which are responsible for the activity of those enzymes, and not the entire native protein. The inventors have for the first time provided methods and compositions for the expression of biologically active P450 domain comprising fusion proteins in bacterial systems. In general, the present invention concerns stably transformed bacterial cells that express a biologically active fusion protein or that contain DNA segments encoding for fusion proteins and are useful as clone banks, methods for the production of biologically active fusion proteins in recombinant bacteria, methods for the metabolism of cytochrome P450 substrates with expressed fusion proteins, DNA segments encoding fusion proteins which have been modified to allow effective bacterials expression or are suitable for inclusion in bacterial genomes used as clone banks, methods for preparing bacterial cells comprising DNA segments encoding fusion proteins, methods for obtaining DNA segments comprising genes encoding fusion proteins, as well as methods for obtaining bacterial expression of a biologically active fusion protein.

Accordingly, in certain embodiments, the invention concerns stably transformed bacterial cells which express a biologically active eukaryotic cytochrome P450 enzyme or fusion protein. Such proteins include a P450 domain encoded by a recombinant gene, having associated expression elements capable of effecting bacterial transcription and translation of the gene. These elements include a bacterially compatible ribosome binding site, spacer region, transcription terminator, and promoter elements. As used herein, the term "bacterially compatible" is intended to refer to genetic elements that are compatible with and therefore capable of functioning in bacteria and include generally bacterial elements, phage elements and the like.

The development of the present invention rests in part on the inventor's discovery that most, if not all, eukaryotic P450 genes must be structurally modified so as to allow their expression in bacteria in a biologically active form. Most generally, this will include combining the eukaryotic cytochrome P450 gene with bacterial expression elements such as a bacterially compatible ribosome binding site, spacer region, transcription terminator and promoter. This is because most corresponding eukaryotic elements will not adequately function in bacterial hosts.

In connection with most if not all embodiments of this invention, one will typically also desire to modify the structural gene to effect an improved bacterial expression capability. In certain embodiments, one may chose to modify certain codons of the P450 structural gene. For example, it may be necessary to modify the codon for the second amino acid (defined as that codon which immediately follows the translation start codon, ATG) to reflect a codon preferred for bacterial expression and to thus effectuate biologically active bacterial expression. Such preferred codons include GCT (Ala), AAA (Lys), ACC, ACT (Thr), TAT (Tyr), AAT, AAC (Asn), CAC, CAT (His), CGT, AGA, CGC (Arg), TTT (Phe), ATC, ATA, ATT (Ile), GTA (Val), TTG, CTT, CTC, TTA (Leu), GCC, GCA (Ala), GAA (Glu), AGC, and AGT (Ser). Of these, GCT and AAA will be particularly preferred. Note that certain second codons should be avoided for bacterial expression, including TTC (Phe), CTA, CTG (Leu), TCA, TCT, TCC, TCA, TCG (Ser), CCG, CCT, CCC, CCA (Pro), ACA, ACG (Thr), GCG (Ala), CAG, CAA (Gln), GAT, GAC (Asp), GAG (Glu), TGT, TGC (Cys), TGG (Trp), CGG, AGG (Arg), GGT, GGC, GGA, GGG (Gly), ATG (Met), GTT, GTC, GTG (Val), TAC (Tyr), and AAG (Lys).

Where the N-terminus of the structural P450 gene is being selectively modified, an additional or alternative modification which the inventor has found to be beneficial is the modification of the codon encoding the fourth and/or fifth amino acid (as measured from the start codon) to create an AT rich codon. As used herein, the phrase "AT rich" codon is intended to refer to a codon which includes at least two As or Ts and preferably all three nucleotides of the codon should be an A or a T. Of course, where possible, one will desire to leave the same amino acid encoded at the fourth and fifth position and yet select a codon for this amino acid that is AT rich. Thus, for example, where the fourth and fifth amino acids are Leu and encoded by CTC or CTG, one can modify these positions to incorporate and AT rich codon such as TTA and achieve the objective of an AT rich codon without changing the encoded amino acid.

The inventors have found that an alternative and particularly fruitful approach to improve the expression of a protein comprising a eukaryotic cytochrome P450 domain in bacteria is to create a hybrid polypeptide or fusion in which the N-terminal amino acids of the protein are derived from another eukaryotic cytochrome P450, and preferably, in which the first 9 amino acids are derived from the bovine 17α-hydroxylase gene. The addition of this segment to the N-terminal of a distinct cytochrome P450 gene has been found to result in a P450 hybrid enzyme that is effectively expressed in bacteria, but which nevertheless exhibits only those properties of the chosen P450 enzyme.

Hybrid P450 enzymes created in this manner may contain their full P450 domain coding sequence and the additional N-terminal residues, or alternatively, the additional residues may be used to replace part of the original structural gene. Where the latter option is chosen it is generally considered that the nucleotides encoding between 1 and 40, and more preferably, between 12 and 22 of the amino acids originally at the N-terminal of the chosen P450 gene may be deleted before addition of the preferred N-terminal segment. The recombinant P450 enzyme so produced may then either be slightly larger or smaller than its native counterpart, but the inventors have determined that the catalytic and structural properties of such hybrid P450 enzymes are identical to the chosen native counterpart.

Accordingly, and as used herein, the terms "P450 enzyme hybrid" or "hybrid enzyme" generally refer to polypeptide comprising a eukaryotic cytochrome P450 domain in which the N-terminal residues are derived from a distinct eukaryotic P450 gene, and most preferably, in which the 9 N-terminal residues are derived from bovine 17α-hydroxylase. Therefore, in preferred embodiments, the 5' end of the P450 hybrid structural gene will contain the nucleotides ATG GCT CTG TTA TTA GCA GTT TTT CTG (SEQ ID NO:2) directing the expression of a P450 enzyme hybrid in which the N-terminal amino acids are Met Ala Leu Leu Leu Ala Val Phe Leu (SEQ ID NO: 1). However, it will be appreciated that this aspect of the present invention is not limited solely to the use of these 9 codons and amino acids per se. It is contemplated that variants of this sequence may be used in accordance with the present invention, in which certain nucleotides (and perhaps the amino acids thus encoded) may be substituted, whilst maintaining the general features advantageous for bacterial expression, as outlined above.

In other embodiments, advantages in accordance with the invention may be realized by ensuring that the first 25 codons of the cytochrome P450 domain of the gene include not more than 2 rare codons. As used herein, the term "rare codon" is intended to refer to those codons which are used at a frequency of less than 10% for the amino acid which they encode, and include CTA, TCA, AGT, ACA, GGA, CCC, ATA, GGG, CGA, CGG, AGA, AGG. More preferably, one may desire to ensure that the first 25 codons of the eukaryotic cytochrome P450 gene are devoid of rare codons, particularly AGA (Arg) and AGG (Arg).

An additional modification which may prove beneficial is the alteration of the coding sequence in a manner which will act to disrupt possible unfavorable secondary mRNA structure within approximately 20 nucleotides 5' or 3' of the ATG initiation codon. It is believed that the translational efficiency of bacterial mRNAs is dependent on the degree to which this region of single stranded RNA is unfolded. The greater the degree of an extended, open conformation in this region, as opposed to a folded structure stabilized by intramolecular base pairing, the greater the translational efficiency and subsequent synthesis of the gene product. Therefore, it may be helpful to alter specific nucleotides in this region to disrupt potential secondary structure. Several mathematical algorithms are available in software packages to predict the structure and stability of RNA's (e.g., Jaeger et al., 1989). These programs may be used to predict the stability of alternative mRNA sequences. Judicious changes in nucleotide sequence can significantly reduce the stability of secondary structures and therefore provide a better template for transcription initiation. Generally speaking, this can be achieved by maximizing the AT content of the codons for the first 8–12 amino acids of the P450 protein. Analysis of DNA sequences that function to promote translation initiation indicates a pronounced AT-richness as well as a deficiency of C residues in these DNA sequences (Dreyfus, 1988). Accordingly, degenerate codons for amino terminal P450 amino acids should be chosen so as to maximize the preferred nucleotides, the preference series being: A>T>G>C.

While the aforementioned modifications aim to minimize secondary structure formation between a particular ribosome binding site (RBS) spacer sequence and the amino terminal codons of a particular P450 they may not be necessary in all cases. There may be particular RBS spacer sequences, that due to their own nucleotide sequence, tend to not form inhibiting structures (e.g. the RBS spacer sequence from T7 gene 10). Likewise, there may be certain P450s whose amino terminal codons tend to not form inhibiting structures due to, for example, the natural occurrence of AT rich codons in this region of the cDNA. The inventor contemplates that these modifications will not always be required in that some eukaryotic cytochrome P450s or fusion proteins may be expressed directly. In these instances, however, it will nonetheless be necessary to combine the DNA segment encoding the cytochrome P450 domain with appropriate elements which are capable of effecting bacterial transcription and translation, including a bacterially compatible ribosome binding site, spacer region, transcription terminator, and promoter.

In terms of the promoter, it is believed that virtually any promoter functional in the selected bacterial host may be employed. However, preferred promoters include the tac, lac, lac UV5, tac, trc, $\lambda P_L$, T7 or T3 promoter. Of course, the $\lambda P_L$, T7 and T3 promoters are derived from bacteriophage and are known to be functional in bacteria such as E. coli. While conventional wisdom would suggest that strong promoters would be preferred, the present inventor has observed that this may not be the case for the functional expression of proteins comprising eukaryotic cytochrome P450 domains in bacteria. For example, while the T7 promoter is one of the strongest promoters yet identified, its use in connection with the cytochrome P45017α-hydroxylase (P₄₅₀17α) results in the expression in *E. coli* of large amounts of the enzyme, much of which, however, is spectrally inactive and found in an insoluble form. However, the use of a tightly regulated lac promoter in conjunction with the RBS and spacer sequence of gene 10 from T7 virus results in high level expression of active membrane bound P450 enzyme. Thus, transcription of the 17alpha gene from the lac promoter yields active enzyme while transcription from the T7 promoter yields an insoluble protein. It is possible that subtle changes in growth media, temperature and or induction regimen may be necessary for functional expression in these systems. Of particular interest is the possibility that hemin (a cofactor of all functional P450 enzymes) may be limited in these cells. Addition of the heme precursor, 5-aminolevulinic acid (ALA) may circumvent this problem. Alternatively, coexpressing the *E. coli* enzyme that produces ALA, ALA synthase, may also function in this regard. This gene has been cloned and its sequence has been published.

The inventor has found that the preferred promoter for bacterial expression is the tac promoter/ribosome binding site, which is available in "cassette" form (Pharmacia 27-4883-01). The activity of this promoter is negatively regulated by the production of the lac repressor from a cloned copy of the lac I gene.

One will often desire to incorporate an appropriate ribosome binding site for effectuating bacterial expression into the eukaryotic cytochrome P450 domain comprising gene. Often, the ribosome binding site and promoter can be incorporated as a "cassette" defined as a contiguous, pre-fabricated DNA segment which incorporates the desired elements and has useful restriction enzyme recognition sites at its two termini, allowing it to be readily inserted at an appropriate point within the desired cytochrome P450 gene by simple genetic manipulation.

Most conveniently, one may desire to simply employ a promoter and ribosome binding site from a homologous system, such as the lac promoter and its associated RBS. In general, however, it is proposed that one may employ any effective bacterial ribosome binding site, with those RBSs from *E. coli*, λ, T7 or T3 being preferred. Even more preferred ribosome binding sites are those from the T7 gene 10, or *E. coli* lac a, lac z, trp A, trp B, trp C, trp D, trp E, trp L, trp R or trp S genes. A particularly preferred ribosome binding site and spacer region comprises the sequence 5'-AGGAGGTCAT-3'(SEQ ID NO:3) wherein the underlined portion comprises the ribosome binding site and the adjacent CAT sequence comprises the spacer region. (The spacer region is that sequence between the ribosome site and the ATG initiation codon.)

One will also typically desire to incorporate an appropriate bacterial transcription terminator, which functions to terminate the function of bacterial RNA polymerases, the enzymes responsible for transcribing DNA into RNA into a gene prepared in accordance with the invention. The requirements for a functional bacterial transcription terminator are rather simple, and are usually characterized by a run of T residues preceded by a GC rich dyad symmetrical region. The more preferred terminators are those from the TRP gene, the ribosomal terminators, rrnB, or terminator sequences from the T7 phage. In fact, the T7 terminator sequences contain RNase III cleavage sites with a stem-loop structure at the 3'ends of mRNAs which apparently slows down message degradation.

Certain aspects of the present invention are exemplified by the expression of the bovine 17α-hydroxylase P450 gene. Further embodiments concerning the creation and expression of hybrid cytochrome P450s, containing a small N-terminal section of the 17α-hydroxylase gene, are exemplified by the expression of cytochromes 1A2, 3A4, 1A1 and 2C8. However, it is believed that the techniques disclosed herein will be generally applicable to all eukaryotic cytochrome P450s, many of which have similar structural and functional characteristics. Thus, it is proposed that the invention will be generally applicable to members of the cytochrome P450 I, II, III, IV, VI, XIA, XIB, XVII, XIX, XXI and XXVI family. However, for commercial applications it is proposed that preferred cytochrome P450 for application in connection with the present invention will be the steroid hydroxylases, steroid biosynthetic enzymes P450 XIA1 (SCC), P450 XIB1 (11β), P450 XVIIA1 (17α), P450 XIXA1 (aromatase) and P450 XXI (C21) and the xenobiotic metabolizing enzymes P450 I (P₁ and P₃), P450 II (1, LM2, mp, dbl, and j), P450 III (nf) and P450 IV (LA).

Moreover, although the present invention is exemplified in terms of an *E. coli* bacterial host, there is no reason why other types of bacteria cannot be employed in place of *E. coli*. For example, one may desire to employ a member of the gram negative family Enterobacteriaceae, which comprise 18 genera. The most closely related to *E. coli* are Salmonella and Shigella, and less closely related are the Enterobacter, Serratia, Proteus and Erwinia. Of these, expression of P450 in Salmonella, Bacillus and Pseudomonas, may be preferred.

A particularly surprising aspect of the present invention is the finding that recombinant bacteria have been found to produce a biologically active eukaryotic cytochrome P450 enzyme without the need for an associated eukaryotic cytochrome P450 reductase. Although cytochrome P450 enzymes require the presence of a reductase or associated electron transfer capability in order to function, it is apparently the case that the bacterial system set forth herein produce an electron transfer capability that is capable of substituting for eukaryotic P450 reductases. However, for certain applications it may be necessary to cotransform bacteria with an appropriate eukaryotic or prokaryotic P450 reductase expression plasmid in order to achieve a maximally active enzyme. The inventor proposes that this reductase may most preferably be introduced on a plasmid together with the selected P450 enzyme gene or on a separate plasmid under a different antibiotic selection than the recombinant P450. Alternatively, the cDNA encoding the reductase may be integrated into the *E. coli* genome to produce a bacterial cell line which synthesizes this auxiliary enzyme. Additionally, the reductase need not be of eukaryotic origin as the reductase moiety of cytochrome P450 BM3 (of *Bacillus magaterium*) has been shown to be capable of electron transfer to eukaryotic P450s.

The present invention also encompasses another surprising mechanism for obtaining cytochrome P450 activity. The inventors have shown that it is possible to express a functional "fusion protein" comprising a eukaryotic P450 domain fused to a reductase domain in a bacterial system. With such a fusion protein, there is no need to supply an associated eukaryotic cytochrome P450 reductase in a separate manner. Therefore, there would be no need to introduce either a separate plasmid containing such a reductase, or the need to place such a reductase on a separate region of the plasmid containing a selected P450 enzyme gene. The inventor proposes that the fusion also will allow for greater P450 activity since the fusion protein places P450 and reductase domains in close proximity.

Of course, one unique feature of a fusion protein that has been expressed in a bacterial system as opposed to a eukaryotic system is the lack of typical eukaryotic glycosylation in conjunction with the protein. It is proposed that this lack of glycosylation will render fusion proteins produced in bacterial systems particularly useful. For example, it is proposed that the non-glycosylated proteins may be easier to purify or have greater enzymatic activity.

In an exemplary embodiment of the present invention, the inventors expressed a functional bovine P450 17A1 fused to a rat liver NADPH-P450 reductase. The fused reductase is truncated and linked with a dipeptide linker of SerThr to the carboxy-terminal end of cytochrome P450. The fusion protein is expressed in E. coli, in the membrane fraction of all disrupted E. coli cells. Where desired, the fusion protein may be solubilized using detergents such as CHAPS, Triton X 100, Brij series, Emulgen 911, Emulgen 913, Cholate or the Tween series.

Purification of fusion proteins is achievable by various methods. Various degrees of purity may be obtained by employing these methods. Of course, the degree of purity desired will depend largely upon the application for which the purified fusion protein is to be put to use. For example, were one to desire to do x-ray crystallography studies on the structure of a fusion protein, he or she would need extremely pure protein, however, if one's goal is to metabolize a dangerous substrate into less dangerous metabolites, substantially less pure fusion protein might be employed. For some applications, it might be sufficient to make use of whole bacterial cells which express the fusion protein. For other applications, one may wish to use disrupted cells or fusion proteins which have been solubilized using any of the above detergents. Should further purification be required, there are a number of techniques which are well known in the art for purifying proteins, including cellulose chromatography followed by affinity chromatography on 2'-5' ADP sepharose or NADP sepharose, hydroxylapatite, and/or gel filtration. In the exemplary embodiment of the fusion protein invention discussed above, purification of the fusion protein is achievable by chromatography, and SDS-PAGE analysis shows the fusion protein to be a single protein with molecular weight of about 118 kD. This purified protein was enzymatically active with NADPH in the 17α-hydroxylation of progesterone and pregnenolone.

An interesting aspect of the fusion protein embodiment of the present invention is that at least some fusion proteins produce metabolites which are different from those produced by a corresponding P450 domain that is not fused to a reductase. The inventors anticipate that such differential metabolism may allow for the selection of P450 fusions which produce unique metabolites. This selection would be accomplished by selecting a eukaryotic P450 enzyme or fusion protein which produces the desired compound from the substrates on hand. Furthermore, it is contemplated that fusion proteins may be able to utilize different substrates from the native P450 enzymes from which they are derived.

In many embodiments of the fusion protein invention, the P450 domain is fused to the reductase domain by means of a "linker region." Linker regions tend to be rather short polypeptide sequences that connect two domains of a protein in a manner that allows for biological activity of those domains. Generally, linker regions are short, i.e., less than or equal to 10 amino acids in length with a C-alpha extent of 2–8 Å. However, in some situations it may prove advantageous to employ longer linker regions of up to 300 amino acids in length. For example, it is anticipated that linkers of 10–50 amino acids may serve to separate the domains of a fusion protein and avoid any interference between the functioning of the domains. Furthermore, it may prove feasible to incorporate a new domain of entirely different activity as part of the region linking the P450 and the reductase domains. Linker regions typically have no major kinks or bends in their main chain, and hydrophobic residues are usually absent from linker regions. Of the specific amino acids which could comprise a particular linker region, Ser, Thr, and/or Gly are presumed to be most useful in composing the major portion of the linker. However, small amounts of Asp, Lys, Glu, Asn, and Ala are also allowable in linker regions, as well as one to an unlimited number of Pro residues (Argos 1989). Of course, the inventors do not limit themselves to claiming fusion proteins whereby the fusion of the reductase domain to the P450 domain is accomplished only by the means of a linker region meeting the above requirements. It is anticipated that biologically active fusion proteins may be obtained without the use of the above linker regions.

In the exemplary embodiments of the fusion protein invention where the inventors have expressed a functional bovine P450 17A1 fused to a rat liver NADPH-P450 reductase, a SerThr dipeptide linker was used to fuse the carboxy terminal end of the cytochrome P450 to the amino terminal end of the reductase.

In some embodiments of the fusion protein invention, it is necessary to truncate hydrophobic domains that are in proximity to the region of fusion of the reductase domain to the P450 domain. For example, the inventors have found that it is necessary to truncate the hydrophobic anchoring domain of the amino terminus of the utilized reductase in order to obtain a maximal activity from a fusion protein in which the reductase is fused to the carboxy-terminus of bovine P450 17A1. In the exemplary embodiment of the invention, the rat P450 reductase was truncated at a point immediately following the Lys56 trypsin sensitive side, in order to eliminate potential protease digestion. The inventors anticipate that a systematic series of deletions within bacterially expressed fusion protein systems may identify truncation points with maximal enzymatic activity for each fusion protein produced. Furthermore, while truncation has been required to obtain maximal fusion protein activity from those embodiments of the invention thus far created, the inventors propose that there may be fusion protein constructs or reductase domains which do not require such truncation.

Certain aspects of this invention are exemplified by the utilization of an expression construct that contains unique restriction sites which allow the facile interchange of other P450 domains in the fusion protein sequence. Rat P450 4A1 domains and bovine P450 17A1 domains have been interchanged in the fusion protein construct and were expressed as enzymatically functional fusion proteins. It is anticipated that the restriction sites in the fusion protein constructs will be valuable in allowing the selection of P450 domains which metabolize specific substrates and easy insertion of the selected domains into expression protein constructs. However, the inventors in no way limit themselves to claiming only fusion protein constructs containing such restriction sites.

As noted, the present invention also concerns methods for the production of biologically active eukaryotic cytochrome P450 enzymes, P450 enzyme hybrids or fusion proteins in a recombinant bacterium which includes preparing a bacterial cell as discussed above and culturing the cell under conditions appropriate to effectuate expression of the protein in a biologically active form.

In still further embodiments, the invention concerns a method for the metabolism of a cytochrome P450 substrate which includes preparing a bacterial cell which expresses a biologically active cytochrome P450 domain as discussed above, wherein the expressed enzyme is selected to be capable of metabolizing the substrate, and subjecting the substrate so produced under conditions which will allow the substrate to be metabolized. Of course, the cytochrome P450 enzyme gene is selected such that the encoded enzyme will function to metabolize the particular substrate. While one may desire to at least partially purify the enzyme from the bacterium prior to subjecting the substrate to the enzyme, it is proposed that one may simply employ the recombinant bacteria directly, in that P450 substrates are typically hydrophobic compounds and would be expected to diffuse across biological membranes of intact bacteria to encounter the enzyme. Alternatively, one may desire to first partially purify the desired protein by, for example, simply isolating bacterial membrane fractions which include the enzyme. This is achieved most readily by breakage of the recombinant bacteria by enzymatic, mechanical or sonic disruption and then isolating the bacterial membranes via differential centrifugation.

In still further embodiments, the invention concerns a method for obtaining bacterial expression of biologically active proteins comprising a eukaryotic cytochrome P450 domain. This includes first obtaining a DNA segment which comprises a selected P450 domain encoding gene and modifying the segment so as to operatively combine the gene with the bacterially compatible ribosome binding site, spacer region, transcription terminator and promoter to form a bacterial expression unit. Next, bacteria are transformed with the bacterial expression unit to form transformant colonies. Then a transformant colony which expresses the gene in a biologically active fashion is selected and cultured under conditions to effect expression of the desired protein.

The inventors propose that a particularly advantageous method for achieving expression is to form the promoter, ribosome binding site, spacer region, as well as the various genetic modifications discussed above for effecting improved bacterial expression, into a single bacterial expression plasmid which can be universally employed with any of the P450 domain or fusion protein genes. It is envisioned that such a plasmid will be universally applicable and will comprise the bacterial control elements in combination with the first 10 or so codons modified for bacterial expression, followed by restriction enzyme site(s) which will allow one to splice this amino terminal coding region into the cDNA of the P450 or fusion proteins one wishes to express. Using standard techniques one of these restriction sites will be introduced into the chosen P450 cDNA between the st and 40th codons, and most preferably, between the 12th and 22nd codons. One may then clone this cDNA into the expression plasmid such that the elements necessary for efficient bacterial expression (i.e. promoters, rbs, spacer region and the modified amino terminal codons) are placed in front of the cDNA that encodes the desired protein. Thus, a hybrid P450 or fusion protein is created in which the native 5' codons of any eukaryotic P450 or fusion protein are effectively replaced by modified codons which have a demonstrated ability to promote bacterial expression.

As described above, a particularly preferred DNA coding segment to be used in combination in such an expression plasmid is ATG GCT CTG TTA TTA GCA GTT TTT CTG (SEQ ID NO:2), derived from the 5'-end of the bovine 17α-hydroxylase gene. When the chosen cytochrome P450 gene is cut at an appropriate restriction site and inserted into a plasmid containing this sequence, it can then be expressed in bacteria in a hybrid form in which the 9 N-terminal residues will correspond to those of bovine 17α-hydroxylase, i.e. Met Ala Leu Leu Leu Ala Val Phe Leu (SEQ ID NO:1). However, it will be appreciated that expression plasmids may be constructed in accordance with the present invention which may contain 10 or so other codons in which certain nucleotides (and perhaps the amino acids thus encoded) may be substituted, whilst maintaining the general features herein described to be advantageous for bacterial expression.

BRIEF DESCRIPTION OF THE DRAWINGS

FIG. 5. Alignment of P450 N-terminal amino acid sequences with the first 9 amino acids of the N-terminus of bovine P450 17A1. Boxed areas show the identity of regions between the various P450s. Regions of conservative amino acids present in the alignment are not highlighted. Reading from the top to the bottom, these amino acid sequences represent SEQ ID NO:6 through SEQ ID NO:12.

FIG. 8. (A) Diagram disclosing the DNA sequence and deduced amino acid sequence of the region of fusion between the bovine 17A1 P450 domain and the rat cytochrome c reductase domains. The numbering refers to the last amino acid of original bovine P450 17A1 (Pro509) and the beginning of the truncated rat liver cytochrome c reductase domain (Ile57). The Sal 1 and the hybrid Sal 1/Xho 1 sites are underlined. These amino acid and nucleotide sequences are SEQ ID NO:13 and SEQ ID NO:14, respectively. (B) The fusion of a rat 4A1 P450 domain and the rat cytochrome c reductase domain. These amino acid and nucleotide sequences are SEQ ID NO:15 and SEQ ID NO:16, respectively.

FIG. 9. Diagram showing the modification of the amino terminal of the rat P450 4A1 in preparation for creating a fusion protein. Numbered residues in bold are those of the rat P450 4A1. These amino acid and nucleotide sequences are SEQ ID NO:17 and SEQ ID NO:18, respectively.

DETAILED DESCRIPTION OF PREFERRED EMBODIMENTS

Figure 1:
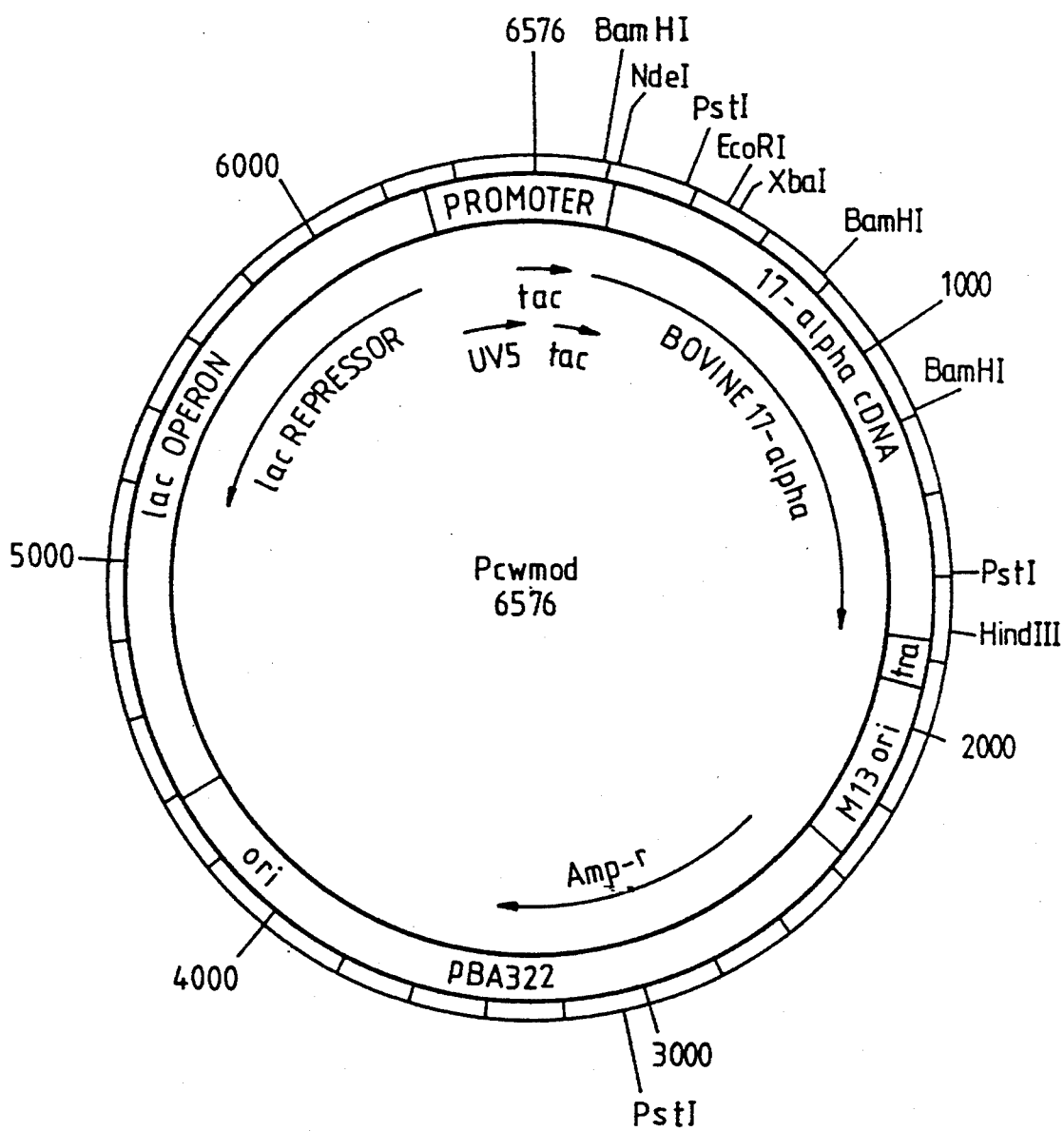
FIG. 1. Restriction map of the pCWmod17 plasmid employed in the preparation of recombinant bacteria which express $P450_{17\alpha}$(ATCC accession number 68511).

The present invention has developed bacterial expression systems for producing mammalian cytochrome P450s and fusion proteins in an enzymatically active form. Generally speaking, this has been achieved through the modification of a eukaryotic cytochrome P450 gene to incorporate bacterial expression elements including a bacterially compatible ribosome binding site, spacer region, transcription terminator and promotor.

As discussed in general terms above, the inventor has determined that one may find it necessary to modify the coding sequence of a gene comprising a eukaryotic P450 domain or fusion protein to render the amino terminal coding region acceptable for bacterial expression. In certain embodiments, these modifications may include changes in the second and/or the fourth or fifth codons of the structural gene encoding the eukaryotic cytochrome P450. However, in other embodiments, the most advantageous method of preparing an N-terminal region for effective bacterial expression may be to create a hybrid protein a cytochrome P450 domain in which the N-terminal amino acids are derived from a distinct eukaryotic P450 enzyme, and most preferably, in which the first 9 amino acids are derived from bovine 17α-hydroxylase.

The aspects of the present invention concerning codon modification are exemplified through the expression of bovine 17α-hydroxylase ($P450_{17\alpha}$), whereas the bacterial expression of cytochrome P450 hybrids is exemplified using cytochromes 1A2, 3A4, 1A1 and 2C8. However, it is proposed that the techniques and modifications disclosed herein will be applicable to eukaryotic cytochrome P450s in general.

Although the invention is herein exemplified through the use of an E. coli host, it is proposed that the invention will be generally applicable to other bacterial hosts, particularly those related to E. coli, and their uses not excluded. Surprisingly, it has been found that the bacterial host used to exemplify the invention contains an electron transport system that can substitute for the mammalian microsomal NADPH-cytochrome 450 reductase in supporting the 17α-hydroxylase and 17, 20-lyase activities of $P450_{17\alpha}$. Thus, it is proposed that one may often be able to employ such hosts without the need for adding extrinsic reductase or incorporating a separate mammalian reductase gene into the bacterial host.

An important aspect of the present invention is the use of a bacterial ribosome binding site, spacer region and terminator. Suitable elements in this regard are well known in the art and they may be combined with the selected gene in appropriate fashion through the application of well known techniques.

Although there are hundreds of E. coli promoter sequences, only a handful of these are typically employed in bacterial expression systems. These tend to be strong promoters that are highly regulated. The most commonly employed, and those generally preferred for use in the present invention, are the trp, lac (or hybrids of these such as the lac UV5 tac and trc promoters), $\lambda P_L$, as well as promoters found in the genes of other E. coli viruses such as T7 or T3. The tac promoter has proved to be particularly beneficial. If one does not desire to employ the tac promoter, it is believed that other promoters may be substituted, with the lacZ, $T_7$ and $\lambda P_L$ being preferred. However, the present invention is by no means limited to these embodiments and one may refer to publications such as Hawley et al., 1983, and Hoopes et al., (1987 for other useful promoters.

Although the conventional wisdom is that strong promoters are the best promoters, the inventor's studies have indicated that this may not hold true for the functional expression of a protein with a eukaryotic cytochrome P450 domain, such as $P450_{17\alpha}$. The reason for this is that when the modified $17\alpha$ cDNA is placed into an expression vector containing a promoter, ribosome binding site and spacer region of gene 10 from T7 virus, it was expressed in *E. coli* in large amounts but most of the protein was spectrally inactive and found in a relatively insoluble form in the cells. Interestingly, the T7 promoter is one of the strongest promoters yet identified and the RBS and spacer region are most certainly very efficient in translation initiation and elongation. However, clones containing a highly regulated 120 promoter T7 gene 10 RBS spacer sequence upstream of the native or modified 17 alpha cDNA sequence yield large amounts of active enzyme. While the reason for this is unclear, the inventor's working hypothesis in this regard is that eukaryotic P450s need to be synthesized slowly in a highly regulated manner such that the cells are given time to metabolically adapt to the production of this foreign protein.

The use of a bacterially compatible ribosome binding site also appears to play an important role in the practice of this invention. Generally speaking, it is believed that most known ribosome binding sites, and their associated spacer regions, may be employed to some advantage in connection with this invention. Numerous such RBS are known (Gren, 1984). The Gren article, in fact, discloses a large number of ribosome binding sites and their associated spacer regions which have been sequenced from RNA phage, DNA phage and *E. coli* genes. While it is believed that virtually any of these ribosome binding sites may find utility in connection with the present invention, it is believed that the particularly preferred ribosome binding sites will be those from λDNA phage, the T7 phage, as well as various *E. coli* genes. Of these, those that are particularly preferred are the RBS and spacer from the T7 gene 10, *E. coli* lac a, lac z, trp A, trp B, trp C, trp D, trp E, trp L, trp R, and trp S. For the optimization of RBS structure, one may wish to refer to DeBoer et al., (1990).

The upstream region of the inventor's most preferred embodiment, the pCW plasmid (discussed in more detail below), is 5=-ATCGATGCTTAGGAGGT CATATG-3'(SEQ ID NO:19), wherein the first underlined portion is the RBS and the second is the initiation codon (ATG). The rbs here is seven nucleotides and is combined with a rather short spacer of three nucleotides (CAT). Thus, the RBS is longer than necessary while the spacer is suboptimally short, at least this is what one would expect based on what is known about most RBS/spacer combinations.

The use of a bacterial transcription terminator is also an important aspect of the invention. In general, it is believed that one may employ virtually any bacterial terminator sequence. A useful listing of terminator sequences which the inventor believes one may use in connection with the present invention can be found in Rosenberg et al., 1979. Generally speaking, simple bacterial terminators are characterized by a series of thymidine residues at the 3' end of the gene, preceded by a GC-rich region of dyad symmetry in the DNA. Some terminators have a run of adenines (preceding the GC-rich region) that can apparently provide a symmetric counterpart to the uridine-encoding region, and should thus function in both directions. This has been demonstrated for rho independent terminators and for the rrnB operon.

Terminators seem to be important in the stability of plasmids carrying strong promoters. The terminators which are most frequently used in expression vectors are the trp or the ribosomal terminators, rrnB. Terminator sequences from T7 phage have also been used frequently in expression vectors since they contain RNase III cleavage sites which leave a stem-loop structure at the 3' ends of mRNAs that apparently slows down the degradation of these messages in *E. coli* (Danayotatos et al., 1985).

An important aspect of the invention concerns the modification of a gene comprising a eukaryotic cytochrome P450 domain to insure a nucleotide sequence that favors expression in a bacterial host. A principal focus of these modifications is the codon which codes for the second amino acid of the enzyme, measured from the initiation codon, ATG. Studies undertaken by others have demonstrated that the second codon can influence the expression efficiency of the lac Z structural gene, and found that certain codons are preferred over others where an enhanced efficiency is desired (Looman et al., 1987). Surprisingly, the present inventor has found that the second codon, at least in the context of eukaryotic cytochrome P450 expression, plays a role in the generation of biologically active eukaryotic P450 enzymes as well. For example, when the second codon of $P450_{17\alpha}$ is modified to incorporate a codon highly preferred for bacterial expression, in combination with additional modifications discussed below, a biologically active enzyme is produced. However, when the second codon of $P450_{17\alpha}$ is left unchanged in its natural state (TGG), and additional modifications are not made, no detectable biologically active enzyme is produced.

The inventor proposes that one will desire to modify the second codon of a selected cytochrome P450 domain gene so as to ioncorporate a codon preferred for bacterial expression. Exemplary preferred codons include GCT (Ala), AAA (Lys), ACC, ACT (Thr), TAT (Tyr), AAT, AAC (Asn), CAC, CAT (His), CGT, AGA, CGC (Arg), TTT (Phe), ATC, ATA, ATT (Ile), GTA (Val), TTG, CTT, CTC, TTA (Leu), GCC, GCA (Ala), GAA (Glu), AGC, AGT (Ser). Of these, the GCT codon is particularly preferred. Of course, where possible, one will desire to modify the second codon so as to maintain the same primary amino acid structure of the resultant expressed enzyme. This will be possible, however, only where the second amino acid is Phe, Leu, Ile, Val, Thr, Ala, Arg, Asn, Glu, His, Lys, Ser, or Tyr, in that no preferred codons exist for the remaining amino acids (Met, Pro, Gln, Asp, Cys, Gly, Trp).

Just as some codons are to be preferred at the second position, certain codons are to be avoided. For example, the inventor has prepared a construct which comprised the native $P450_{17\alpha}$ sequence, except that the second codon was changed to GGG (Gly), placed downstream from the strong trc promoter. This construct failed to produce any immunodetectable protein. Thus, GGG is to be avoided. It is believed that other codons which should be avoided include TTC (Phe), CTA, CTG (Leu), TCA, TCT, TCC, TCA, TCG (Ser), CCG, CCT, CCC, CCA (Pro), ACA, ACG (Thr), GCG (Ala), CAG, CAA (Gln), GAT, GAC (Asp), GAG (Glu), TGT, TGC (Cys), TGG (Trp), CGG, AGG (Arg), GGT, GGC, GGA, GGG (Gly), ATG (Met), GTT, GTC, GTG (Val), TAC (Tyr), and AAG (Lys).

A second consideration which appears to be important in the modification of P450 genes to effect biologically active bacterial expression is the nucleotide sequence between nucleotides 10 and 15 (i.e., codons 4 and 5). It has been proposed by Stormo, et al. (1982) that it is important to maintain an AT richness in this region where one desires to promote bacterial expression. Thus, in modifying eukaryotic P450 domain containing genes for bacterial expression, one will desire to introduce codons which have at least two A or T residues, and preferably three such residues. These modifications will preferably result in "silent" mutations which will not change the resultant amino acid structure of the enzyme. Of course, certain amino acids are encoded only by codons which, at most, have only one A or T residue (e.g., Gly, Ala, or Pro). Where the fourth or fifth amino acid of the selected P450 domain is one of these, it may be necessary to modify the primary amino acid sequence in order to introduce an appropriate codon sequence at these positions.

An additional modification which may prove beneficial is the introduction of homology sequences which will promote transcription initiation and or elongation in *E. coli*. These considerations are based on the finding by Peterson et al., 1988, that the vast majority of *E. coli* mRNAs (greater than 98%) contain at least three consecutive nucleotides from the sequence 5' TCAAACTCTTCAATTT 3' within the first 21 nucleotides following the ATG initiation codon. It will be noted that the modified codons of P450$_{17\alpha}$ described herein contain several of these nucleotides in the prescribed location. Namely, the sequence CTCT is found within codons two (GCT) and three (CTG) while the triplet TTT is found reiterated in codons seven and eight (GTT TTT). Such sequences are thought to be involved in base pairing with the 5' terminus of bacterial 15S ribosomal RNA, which is an important step in efficient transcription initiation and or elongation in *E. coli*. Such sequences are preferably introduced into eukaryotic P450 cDNA sequences if they do not already contain them.

Additionally, it is proposed that the presence of rare Codons, especially AGA and AGG coding for Arg, within the first 25 codons will be deleterious to efficient expression (Chen et al., 1990). Additional rare codons which one might seek to avoid include CTA, TCA, AGT, ACA, GGA, CCC, ATA, GGG, CGA, CGG, AGA, and AGG.

Another matter of potential focus concerns the second amino acid. Others have found that the size of the side chain of the second amino acid determines whether the N-terminal Met residue will be removed (Hirtel et al., 1989; Dalboge et al., 1990). This becomes important in light of studies by Bachmair et al. (1988), which demonstrate that the N-terminal amino acid of a protein determines its rate of degradation in the cell. If the native second amino acid leads to N-terminal Met processing and the next exposed amino acid gives rise to a protein with a short half-life, one will desire to alter this residue to prevent such an occurrence. Thus, one may consider ensuring that the second amino acid is Ser, Ala, Thr, or Val.

A particularly useful approach to create a eukaryotic cytochrome P450 domain in which the N-terminus is adapted for bacterial expression is to create a hybrid P450 domain in which the N-terminal amino acids of the protein are derived from another eukaryotic cytochrome P450. The inventors have determined that the addition of a 27 nucleotide segment from the bovine 17α-hydroxylase gene is particularly advantageous in this regard. The codons ATG GCT CTG TTA TTA GCA GTT TTT CTG (SEQ ID NO:2) can be used to direct the bacterial expression of a P450 enzyme hybrid or fusion protein in which the first 9 N-terminal amino acids are Met Ala Leu Leu Leu Ala Val Phe Leu (SEQ ID NO:1). Cytochrome P450 enzyme hybrids expressed in this manner exhibit the properties of the chosen P450 enzyme.

Active P450 hybrid enzymes or fusion proteins could be produced in which the additional residues form an N-terminal extension to the P450, or alternatively, in which the additional residues replace part of the N-terminus of the original protein. The inventors contemplate that the nucleotides encoding between 1 and 40, and more preferably, between 12 and 22 of the amino acids originally at the N-terminal of the chosen P450 domain gene may be deleted before the addition of the preferred N-terminal sequence. The P450 hybrid enzymes thus created may have a slightly different molecular weight than the native protein, but will retain full catalytic activity.

It is proposed that virtually any bacterial expression vector which is adapted for the particular bacterial host that is selected can be employed in the practice of the present invention. Of course, it may be necessary to modify the expression vector to take into account the considerations discussed above in terms of not only the appropriate ribosomal binding site, spacer region and effective promoter, but also the various modifications for effecting improved bacterial expression. Nevertheless, it is proposed that virtually any appropriate bacterial expression plasmid may be employed where desired, at least as a starting point. These may include but are not limited to pBR322, pAS1, pUC7-19, pKK (223-3, 233-2, 177-3, 240-11), pTrc99A-C, pDR540, pDR720, pPL-lambda, pKC30, pSK(±), Pin-iii, pCZ198, pTTQ8,9,18,19 and 181, pGEMEX-1 and 2, pET1-5, pT7-3-7 and the like.

A preferred plasmid for use in connection with the present invention is designated pCW, which has a restriction map as shown in FIG. 1. The pCW plasmid which was employed in connection with certain aspects of this invention is a derivative of the plasmid disclosed in Muchmore et al. (1989). Synthesis of cloned cDNAs is driven from two copies of a tac promoter/ribosome binding site cassette (Pharmacia 27-4883-01). The activity of this promoter is negatively regulated by the production of the lac repressor from a cloned copy of the lac I gene present in this plasmid. (The pCW vector has very tight regulation of expression, since this vector contains the lac I$^q$ gene, which may be an important factor for expressing eukaryotic P450s in *E. coli*). Upon addition of IPTG to the cells, repression is relieved and synthesis proceeds from the tac promoters through the inserted cDNA and stops at a downstream transcription terminator.

While information provided to the inventor by the developer of this plasmid indicated that the DNA sequence between the last tac promoter and the ATG codon of the cloned DNA (i.e., the "spacer region") is derived from the T4 lysozyme gene, a preliminary search of the lysozyme gene failed to uncover the presence of this sequence. Furthermore, this spacer also contains an ATG codon which may also initiate protein synthesis due to its proximity to ribosome binding sites in the tac promoter cassette. Therefore, in that the precise structure of this clone is not clear, the inventor has deposited samples of the clone which contain the modified $P450_{17\alpha}$ gene discussed in the examples below with the ATCC on Jan. 9, 1991, as deposit number 68511, under the provisions of the Budapest Treaty.

In order to use this plasmid for the expression of other P450 genes, Nde I (CATATG) restriction enzyme site is preferably introduced at the ATG initiation codon of the P450 cDNA in question if one does not naturally occur there. In addition, other sequence alterations (described in detail herein) may also need to be introduced into the 5'-coding sequence of the P450 cDNA. A unique restriction enzyme cloning site downstream of the P450 coding sequence is preferably employed to clone the P450 DNA fragment into the plasmid expression vector. A Hind III site (AAGCTT) is preferred since this is the site found in the present plasmid. (However, other unique restriction sites may be rendered compatible to this Hind III site through standard molecular biology techniques). These alterations are most easily accomplished by the synthesis of oligonucleotide containing the desired sequence changes and the introduction of these mutations into the P450 gene by standard PCR mutagenesis techniques (Higuchi et al., 1988). To introduce the alternative P450 coding sequence into the expression vector, the plasmid DNA would be digested with the appropriate enzymes, in this case Nde I and Hind III. The vector DNA fragment is isolated from the $P450_{17\alpha}$ insert fragment and mixed with the approximately digested alternative P450 cDNA sequence in the presence of T4 DNA ligase. The vector now carrying the alternative P450 domain cDNA sequence is introduced into E. coli by standard techniques and used to produce the P450 enzyme by the methods described herein.

Of course, where bacteria other than E. coli are employed, one will desire to use a plasmid that is specifically adapted for use in the selected host. Representative shuttle vectors that replicate in E. coli and B. subtilis are the pHV series plasmids and derivatives of pVB110. Representatives of Streptomyces plasmids are the high copy number plasmids pIJ, pFJ and their derivatives. While the present invention is exemplified in terms of an E. coli host, it is believed that virtually any bacterial host that is amenable to cloning an expression of foreign genes may be employed in connection with this invention. A number of exemplary hosts other than E. coli are known in the art to be useful for this purpose and include Bacillus, Streptomyces, and Pseudomonads. The inventor proposes that one will desire to employ a member of the gram negative family Enterobacteriaceae, which is the family of which E. coli is a member. It is proposed that many members of the other 18 genera of the family Enterobacteriaceae will be suitable expression host. The most closely related E. coli are Salmonella and Shigglia, which are also found in the intestinal tracts of vertebrates.

Enterobacter, Serratia, Proteus and Erwinia are less closely related genera. Of all these bacteria, expression of a protein with P450 activity in Salmonella may have commercial value since this is the host organism for the Ames test which is used to evaluate the carcinogenic activity of chemicals. Expression of proteins with the drug metabolizing activity of P450's in Salmonella could allow for carcinogen activation in vivo as opposed to preincubation of the chemical with a liver extract which is presently necessary to detect compounds which must first be metabolized before they become mutagenic. Other bacteria that might express eukaryotic P450s or fusion proteins are those which synthesize bacterial forms of P450 enzymes. P450s have been identified in Bacillus and Pseudomonas. These are by no means the only bacteria which contain P450 but rather the only ones in which P450s have been well characterized.

One should also consider the fact that eukaryotic P450s are not self sufficient enzymes in that they require oxygen and a reductase enzyme which transfers electrons from NADPH to the P450. Thus, potential expression hosts can not be anaerobes but must be aerobes or facultative anaerobes. The bacteria must be able to grow in the presence of $O_2$. Secondly, the host organism must have a protein capable of transferring electrons to the P450 enzyme. From the inventor's data it appears that E. coli contains such a protein. One might reasonably conclude that other bacteria (especially those bacteria closely related to E. coli) also contain an identical or similar protein. Even if a given bacteria lacks such a reductase it is possible to co-express this protein along with the desired P450.

With the foregoing considerations in mind, the inventor proposes that the present invention will be generally applicable to all eukaryotic cytochrome P450s. A large number of eukaryotic cytochrome P450s have been cloned and their cDNA sequences published and therefore generally available to the art. The following table, Table 1, was generated from the article of Nebert et al., (1989) and sets forth all of the known P450 families, representative members of each family, and references which describe the particular P450 genes. One may wish to refer to the original publication (Nebert et al., 1989) for the particular reference citations, which are not quoted in the Table 1 which follows. It will be appreciated that Table 1 also includes many of the known bacterial P450s, including those from C. tropicalis, Ps. putiva, and B. megaterium.

TABLE 1

| | | | | | |
|---|---|---|---|---|---|
| | | | P450 Genes and Their Products | | |
| Family | Locus Symbol | Protein Name | Trivial Name | Species and Source[a] | References |
| I | CYPIAI | IAI | c | Rat | D Sogawa et al. (1984) |
| | | | | | R Yabusaki et al. (1984) |
| | | | | | D Hines et al. (1985) |
| | | | $P_1$ | Mouse | R Kimura, S. et al. (1984b) |
| | | | | | R Kimura, S. et al. (1987b) |
| | | | $P_1$ | Human | R Jaiswal et al. (1985a) |

TABLE 1-continued

P450 Genes and Their Products

| Family | Locus Symbol | Protein Name | Trivial Name | Species and Source[a] | References |
|---|---|---|---|---|---|
| | | | | | D Jaiswal et al. (1985b) |
| | | | | | R Quattrochi et al. (1985) |
| | | | | | D Kawajiri et al. (1986) |
| | | | form 6 | Rabbit | R Okino et al. (1985) |
| | | | | | R Kagawa et al. (1987) |
| | | | IA1 | Trout | R D Heilmann et al. (1988) |
| | CYP1A2 | IA2 | d | Rat | R Kawajiri et al. (1984) |
| | | | | | D Sogawa et al. (1985) |
| | | | | | P Haniu et al. (1986) |
| | | | $P_3$ | Mouse | R Kimura, S. et al. (1984a) |
| | | | | | R Kimura, S. et al. (1984b) |
| | | | $P_2$ | Mouse | R Kimura and Nebert (1986) |
| | | | $P_3$ | Human | R Jaiswal et al. (1986) |
| | | | | | R Jaiswal et al. (1987) |
| | | | form 4 | Human | R Quattrochi et al. (1985) |
| | | | | | R D Quattrochi et al. (1986) |
| | | | LM4 | Rabbit | P Fujita et al. (1984) |
| | | | | | R Okino et al. (1985) |
| | | | | | P Ozols (1986) |
| | | | | | R Kagawa et al. (1987) |
| IIA | CYP2A1 | IIA1 | a1 | Rat | R Nagata et al. (1987) |
| | CYP2A2 | IIA2 | a2 | Rat | R Matsunaga et al. (1988) |
| | CYP2A3 | IIA3 | a3 | Rat | R Kimura, S. et al. (1989) |
| | | | 15α | Mouse | R Squires and Negishi (1988) |
| | | | P450(1) | Human | R Phillips et al. (1985a) |
| | | | HA3 | Human | R Yamano, S. et al. |
| IIB | CYP2B1 | IIB1 | b | Rat | R Fujii-Kuriyama et al. (1982) |
| | | | | | R Gotoh et al. (1983) |
| | | | | | P Yuan et al. (1983) |
| | | | | | R Phillips et al. (1983) |
| | | | | | R Affolter and Anderson (1984) |
| | CYP2B2 | IB2 | c | Rat | R Fujii-Kuriyama et al. (1982) |
| | | | | | D Mizukami et al. (1983) |
| | | | | | P Yuan et al. (1983) |
| | | | | | R Phillips et al. (1983) |
| | | | | | R Affolter and Anderson (1984) |
| | CYP2B3 | IIB3 | IIB3 | Rat | R Labbé et al. (1988) |
| | CYP2B4 | IIB4 | LM2 | Rabbit | P Heinemann and Ozols (1983) |
| | | | | | P Tarr et al. (1983) |
| | | | p54 | | R Komori et al. (1988) |
| | | | B0 | | R Gasser et al. (1988) |
| | | | $P-450_1$, b15 | | R Komori et al. (1988) |
| | | | B1 | | R Gasser et al. (1988) |
| | | | b46 | | R Komori et al. (1988) |
| | CYP2B4P | (pseudogene) | | Rabbit | D Zaphiropoulos et al. (1986) |
| | CYP2B5 | IIB5 | b52 | Rabbit | R Komori et al. (1988) |
| | | | B2 | | R Gasser et al. (1988) |
| | | | HP1 | | R Komori et al. (1988) |
| | CYP2B6 | IIB6 | LM2 | Human | R Miles et al. (1988) |
| | CYP2B7 | IIB7 | | Human | R Yamano, S. et al. |
| | CYP2B8 | IIB8 | | Human | R Yamano, S. et al. |
| | CYP2B9 | IIB9 | pf26 | Mouse | R Noshiro et al. (1988) |
| | CYP2B10 | IIB10 | pf3/46 | Mouse | R Noshiro et al. (1988) |
| IIC | CYP2C1 | IIC1 | PBc1 | Rabbit | R Leighton et al. (1984) |
| | CYP2C2 | IIC2 | PBc2,K | Rabbit | R Leighton et al. (1984) |
| | | | | | D Govind et al. (1986) |
| | | | | | R Imai et al. (1988) |
| | CYP2C3 | IIC3 | PBc3 | Rabbit | R Leighton et al. (1984) |
| | | | 3b | | P Ozols et al. (1985) |
| | CYP2C4 | IIC4 | 1-88 | Rabbit | R Johnson et al. (1987) |
| | | | PBc4 | | R Zhao et al. (1987) |
| | CYP2C5 | IIC5 | form 1 | Rabbit | R Tukey et al. (1985) |
| | CYP2C6 | IIC6 | PB1 | Rat | R Gonzales et al. (1986a) |
| | | | pTF2 | | R Friedberg t al. (1986) |
| | | | | | R Kimura, H. et al. (1988) |
| | CYP2C6P | (pseudogene) | | Rat | R Kimura, H. et al. (1988) |
| | CYP2C7 | IIC7 | f | Rat | R Gonzales et al. (1986a) |
| | | | pTF1 | | R Friedberg t al. (1986) |
| | CYP2C8 | IIC8 | form 1 | Human | R Okino et al. (1987) |
| | | | IIC2 | | R Kimura, S. et al. (1987a) |
| | | | mp-12, mp-20 | Human | R Ged et al. (1988) |
| | CYP2C9 | IIC9 | IIC1 | Human | R Kimura, S. et al. (1987a) |
| | | | | | R Yasumori et al. (1987) |
| | | | | | R Meechan et al. (1988a) |
| | | | mp-4 | | R Ged et al. (1988) |
| | CYP2C10 | IIC10 | mp | Human | R Umbehauer et al. (1987) |
| | | | mp-8 | Human | R Ged et al. (1988) |

TABLE 1-continued

P450 Genes and Their Products

| Family | Locus Symbol | Protein Name | Trivial Name | Species and Source[a] | References |
|---|---|---|---|---|---|
| | CYP2C11 | IIC11 | h, M-1, 16α | Rat | R Yoshioka et al. (1987) |
| | | | | | D Morishima et al. (1987) |
| | | | | | R Zaphiropoulos et al. (1988) |
| | CYP2C12 | IIC12 | i, 15β | Rat | R Zaphiropoulos et al. (1988) |
| | CYP2C13 | IIC13 | g | Rat | R McClellan-Green et al. (1988) |
| | CYP2C14 | IIC14 | pHP3 | Rabbit | R Imai (1987) |
| | CYP2C15 | IIC15 | b32-3 | Rabbit | R Imai et al. (1987) |
| IID | CYP2D1 | IID1 | db1 | Rat | R Gonzales et al. (1987) |
| | | | CMF2 | Rat | R Ishida et al. (1988b) |
| | CYP2D2 | IID2 | db2 | Rat | R Gonzales et al. (1987) |
| | | | CMF2 | Rat | R Ishida et al. (1988b) |
| | CYP2D3 | IID3 | db3 | Rat | R Matsunaga, E. et al. |
| | CYP2D4 | IID4 | db4 | Rat | R Matsunaga, E. et al. |
| | | | CMF3 | Rat | R Ishida et al. (1988b) |
| | CYP2D5 | IID5 | db5 | Rat | R Matsunaga, E. et al. |
| | | | CMF1b | Rat | R Ishida et al. (1988b) |
| | CYP2D6 | IID6 | db1 | Human | R Gonzales et al. (1988b) |
| | | | | | R Gonzales et al. (1988c) |
| | CYP2D7 | IID7 | | Human | D Kimura, S. et al. |
| | CYP2D8 | IID8 | | Human | D Kimura, S. et al. |
| | CYP2D9 | IID9 | 16α | Mouse | R Wong et al. (1987) |
| | CYP2D10 | IID10 | cb | Mouse | R Ichikawa et al. (1989) |
| IIE | CYP2E1 | IIE1 | j | Human | R Song et al. (1986) |
| | | | | | D Umeno et al. (1988a) |
| | | | | Rat | R Song et al. (1986) |
| | | | | | D Umeno et al. (1988b) |
| | | | 3a | Rabbit | R Khani et al. (1987) |
| | | | | | R Imai et al. (1988) |
| | | | | | D Khani et al. (1988) |
| | CYP2E2 | IIE2 | IIE2 | Rabbit | D Khani et al. (1988) |
| IIF | CYP2F1 | IIF1 | | Human | R Nhamburo et al. |
| IIG | CYP2G1 | IIG1 | olf1 | Rat | R Nef et al. (1989) |
| IIH | CYP2H1 | IIH1 | PB15 | Chicken | R Hobbs et al. (1986) |
| IIIA | CYP3A1 | IIIA1 | pcn1 | Rat | R Gonzales et al. (1985) |
| | CYP3A2 | IIIA2 | pcn2 | Rat | R Gonzales et al. (1986b) |
| | CYP3A3 | IIIA3 | HLp | Human | R Molowa et al. (1986) |
| | CYP3A4 | IIIA4 | nf-25 | Human | R Beaune et al. (1986) |
| | | | pcn1 | | R Gonzales et al. (1988a) |
| | | | nf-10 | | R Bork et al. (1989) |
| | CYP3A5 | IIIA5 | pcn3 | Human | R Aoyama, T. et al. |
| | CYP3A6 | IIIA6 | 3c | Rabbit | R Dalet et al. (1988) |
| IVA | CYP4A1 | IVA1 | LAω 1 | Rat | R Hardwick et al. (1987) |
| | CYP4A2 | IVA2 | LAω 2 | Rat | R Kimura, S. et al. |
| | CYP4A3 | IVA3 | LAω 3 | Rat | D Kumara, S. et al. |
| | CYP4A4 | IVA4 | p-2 | Rabbit | R Matsubara et al. (1987) |
| | CYP4A5 | IVA5 | LAω 1 | Rabbit | R Johnson, E. F. et al. |
| | CYP4A6 | IVA6 | LAω 2 | Rabbit | R Johnson, E. F. et al. |
| | CYP4A7 | IVA7 | LAω 3 | Rabbit | R Johnson, E. F. et al. |
| IVB | CYP4B1 | IVB1 | Lung P450 | Human | R Nhamburo et al. |
| | | | form 5 | Rat | R R. Gasser and R. M. Philpot |
| | | | form 5 | Rabbit | R R. Gasser and R. M. Philpot |
| VIA | CYP6A1 | VIA1 | | House Fly | R Feyereisen, R. et al. (1989) |
| XIA | CYP11A1 | XIA1 | scc | Human | R Chung et al. (1986b) |
| | | | | | D Morohashi et al. (1987a) |
| | | | | Cow | R Morohashi et al. (1984) |
| | | | | | P Chashchin et al. (1986) |
| XIB | CYP11B1 | XIB1 | 11β | Cow | R Chua et al. (1987) |
| | | | | | R Morohashi et al. (1987b) |
| XVII | CYP17 | XVIIA1 | 17α | Cow | R Zuber et al. (1986) |
| | | | | Human | R Chung et al. (1987) |
| | | | | | D Picado-Leonard and Miller (1987) |
| | | | | | R Bradshaw et al. (1987) |
| | | | | | D Kagimoto et al. (1988) |
| | | | | Pig | R Chung et al. (1987) |
| | | | | Rat | R Nishihara et al. (1988) |
| | | | | | R Namiki et al. (1988) |
| | | | | Chicken | R Ono et al. (1988) |
| XIX | CYP19 | XIXA1 | arom | Human | R Simpson et al. (1987) |
| | | | | | R Chen, S. et al. (1988) |
| | | | | | R Corbin et al. (1988) |
| | | | | Chicken | R McPhaul et al. (1988) |
| XXI | CYP21A1 | XXIA1 | c21A | Mouse | D Chaplin et al. (1986) |
| | | | c21 | Cow | D Chung et al. (1986a) |
| | | | | | R John et al. (1986) |
| | | | | | R Yoshioka et al. (1986) |

TABLE 1-continued

P450 Genes and Their Products

| Family | Locus Symbol | Protein Name | Trivial Name | Species and Source[a] | References |
|---|---|---|---|---|---|
| | | | c21 | Pig | P Haniu et al. (1987) |
| | CYP21A1P | (pseudogene c21A) | | Human | D Higashi et al. (1986) |
| | | | | | D White et al. (1986) |
| | CYP21A2 | XXIA2 | c21B | Human | D Higashi et al. (1986) |
| | | | | | D White et al. (1986) |
| | | | | | R Matteson et al. (1987) |
| | CYP21A2P | (pseudogene c21B) | | Mouse | D Chaplin et al. (1986) |
| XXV | CYP26 | XXVIA1 | 26-ohp | Rabbit | R Anderson, S. et al. |
| | CYP51 | P450LI | 14DM | S. cerevisiae | D Kalb et al. (1987) |
| | | | | | D Ishida et al. (1988) |
| | | | | C. tropicalis | D Chen, C. et al. (1988) |
| | CYP52 | P450LII | alk | C. tropicalis | D Sanglard and Loper (1989) |
| | CYP101 | P450CI | cam | P. putida | P Haniu et al. (1982) |
| | | | | | D Unger et al. (1986) |
| | CYP102 | P450CII | BM-3 | B megaterium | D Ruettinger, R. T. et al. | aD, DNA; R, CDNA derived from RNA; P, protein sequence.

A surprising aspect of the present invention is the finding that, at least in the case of E. coli, the host bacterial organism produces an electron-donating capability that can substitute for mammalian cytochrome P450 reductase function. However, it may be the case that for certain P450s or certain bacterial expression hosts, one will desire to co-express a mammalian P450 reductase or other compatible reductase molecule. This would be achieved by cloning the cDNA for the reductase into an expression plasmid carrying an antibiotic resistance marker distinct from that carried by the pCWmod17 plasmid so that both expression plasmids may replicate in the same E. coli cell. Rat liver NADPH-cytochrome P450 reductase has been expressed previously in E. coli (Porter et al., 1987). The reductase coding sequence will be placed downstream of an appropriate E. coli promoter(s), ribosome binding site and spacer region in the plasmid expression vector using standard molecular cloning techniques.

It is proposed that the reductase molecule need not be of eukaryotic origin. For example, the as yet unidentified endogenous E. coli reductase or the reductase moiety of P450 BM-3 (of Bacillus megaterium) may also serve as electron donors for the bacterially expressed eukaryotic P450. Furthermore, the cloned reductase expression unit need not be on a separate plasmid distinct from the pCWmod17 plasmid. A suitable location may be found on the pCWmod17 plasmid where the reductase expression unit may be appropriately placed such that both the P450 and reductase cDNAs will reside on the same plasmid. Alternatively, the reductase expression unit can be incorporated into the E. coli chromosome via phage mediated transduction or lysogeny.

Further embodiments of the invention include the expression of a biologically functional fusion protein comprising a functional P450 domain fused to a functional P450 reductase domain. With such a fusion protein, there is no need to supply a separate eukaryotic cytochrome P450 reductase in a separate manner in order to obtain activity from a bacterially produced P450 enzyme. Accordingly, there is no need to introduce a reductase into the employed bacteria via a separate plasmid or by placing the reductase domain on a separate region of the plasmid containing the selected P450 domain gene. Furthermore, although at least some recombinant bacteria produce a biologically active enzyme without the need for an associated eukaryotic cytochrome P450 reductase, the inventors anticipate that fusion protein constructs will allow a broader range of bacterial genera and species to be employed in the production of active eukaryotic P450 enzymes. The inventors propose that such a fusion will allow for greater P450 activity since the fusion protein places a P450 enzymatic domain and a reductase domain in close physical proximity of each other at all times.

The inventors anticipate that any of the cytochrome P450 enzymes thus far mentioned will have utility in this fusion protein embodiment of the invention. These would include cytochrome P450s of the cytochrome P450 I, II, III, IV, VI, XIA, XIB, XVII, XIX, XXI or XXVI family. For commercial applications, it is proposed that the preferred cytochrome P450 application in connection with the fusion protein embodiment of the present invention will include the previously mentioned steroid, fatty acid, lipid, prostaglandin, leukotriene, vitamin or zenobiotic metabolizing enzymes. It is anticipated that more preferred embodiments of the fusion protein embodiments of the present invention will comprise cytochrome P450 enzymes from the 17α-hydroxylase group. In the most preferred embodiments of this aspect of the invention, the inventors anticipate the use of bovine P450 17A1 and rat P450 4A1 in the cytochrome P450 domain of the fusion protein.

It is proposed that reductase domains from mammalian, other eukaryotic, and bacterial enzymes with P450 reductase activity will provide the necessary reductase activity for this fusion protein system. In the preferred embodiments of the invention, rat liver reductase has been employed as the donor of the reductase domain. However, the inventors anticipate that eukaryotic P450 reductases from human, bovine, rabbit, or other mammals, other vertebrates, or yeast could be employed with utility in this invention. Furthermore, the reductase need not be of eukaryotic origin, for example, the reductase moiety of cytochrome P450 BM3 (of Bacillus magaterium) has been shown to be capable of electron transfer to eukaryotic P450s.

The inventors have typically employed a "linker region" to accomplish the fusion of the P450 domain to the reductase domain in the fusion protein embodiment of the present invention. However, the invention is in no way limited to fusion proteins which contain linker regions. The general characteristics of linker regions should be as follows: 1–300 amino acids in length, a C-alpha extent of at least 2 Å, no kinks or bends in the main chain, a maximal 300 Å$^2$ water accessible surface area (WASA) covered by the non-linker portion of the protein and no hydrophobic residues (Ala, Ile, Val, Leu, Met, Cys, His, Tyr, Trp, or Phe). From these general characteristics, four classes of linker regions can be proposed: Those consisting of Ser, Thr, and/or Gly exclusively; those consisting of primarily Ser, Thr, and/or Gly along with one Asp, Lys, Glu, Asn, Ala, or Pro residue; those containing predominantly Ser, Thr and/or Gly and unlimited Pro residues; and finally, those linker domains containing Ser, Thr and/or Gly, only one Asp, Lys, Glu, Asn, or Ala residue and unlimited Pro residues (Argos 1989).

The inventors anticipate that linker regions following the above described rules and compositions will be useful in preferred embodiments of the fusion protein embodiment of the present invention. Linker regions of any length required can be made in accordance with these rules. In the more preferred embodiments of the present invention, it is anticipated that great utility can be obtained from linker regions comprising Ser, Thr, and/or Gly. In the most preferred embodiment of the linker region of the fusion protein, a SerThr dipeptide linker is employed.

One of the advantages of the SerThr linker is the ability to generate a unique Sal I restriction site within the linker region. Such an expression construct containing the restriction site allows for the facile interchange of other P450 domains previously expressed in E. coli. For example, the presence of the Sal I site in the construction of the fused P450-cytochrome c reductase fusion protein allowed the cytochrome P450 domain from bovine P450 17A1 to be excised from the plasmid with Nde I and Sal I and replaced with rat P450 4A1. The preferred embodiments of the present fusion protein invention may contain such restriction sites. There are hundreds of known restriction sites, and the inventors anticipate that any of them may have utility in the present invention. For the purpose of illustration only, but not limitation of the invention, some exemplary restriction sites which are unique to the vector and the reductase sequence are: Xho I, Spe I, Stu, I, Xba I, and Nhe I. In the most preferred embodiment of the invention, the restriction site will be a Sal I restriction site within close proximity to the linker region.

The inventors have truncated the P450 reductase in the exemplary embodiments of the fusion protein invention. This was done because directly fusing the hydrophobic anchoring domain to the carboxy-terminus of the bovine P450 17A1 prevented expression of a functional P450 fusion protein, presumably because the hydrophobic region interfered with the correct folding of the P450 hydrophobic core. In one embodiment of the present embodiment, rat P450 reductase was truncated at a point immediately following the Lys56 trypsin sensitive site, in order to eliminate potential protease digestion. The inventors anticipate that a systematic series of deletions within the bacterially expressed fusion protein systems may identify a truncation point with higher enzymatic activity. Truncation has been required to obtain maximal fusion protein activity from those fusion proteins thus far created. However, it is anticipated that other modifications in fusion protein constructs such as the addition of new protein domains may result in fusion protein constructs or reductase domains which do not require such truncation.

Biologically active fusion proteins have been obtained from an arrangement whereby the P450 carboxy-terminus is fused to the truncated amino terminus of the reductase. Others have attempted expression in a construct whereby the carboxy-terminus of the reductase was fused to the amino terminus of the P450 in a yeast expression system, the activity of the fusion protein thus obtained was minimal (Sakaki et al., 1990). However, the inventors in no way limit themselves to the P450-reductase arrangement of subunits that is the preferred embodiment of their present invention. It is anticipated that variations in the truncation procedures or linking methodologies employed, such as changes in linker length and sequence could result in functional fusion proteins in which the carboxy-terminus of the reductase is fused to the amino terminus of the P450 enzyme.

Interestingly, the enzymatic specificity of the P450 domain has been altered by fusion to the reductase domain in the creation of a fusion protein. The fusion protein exhibits new enzymatic activities and the production of the new metabolites not seen in reconstituted systems consisting of separate p450s and reductases (see FIGS. 11 and 12). The inventors anticipate that these new enzymatic activities may prove valuable in the production of selected metabolites out of selected substrates.

The growth conditions of the E. coli are believed to be of paramount importance for active and high level bacterial expression of proteins comprising cytochrome P450 domains. For example, growth of cells in standard Luria Broth gives a very low yield of expressed protein. Moreover, growth of cells in Luria Broth or TB media at the standard optimal growth temperature of 37° C. yields significant levels of expressed enzyme, but the cells show no characteristic absorption at 450 nm when in the reduced and carbon monoxide bound state (indicating that the enzyme is produced but is in an inactive state). Additionally, different bacterial strains show marked differences in their ability to produce the enzyme. Thus, it seems clear that factors other than the expression plasmid and the cDNA are important in the production of active enzyme in large quantities.

The following Examples are included to demonstrate preferred modes for the practice of the present invention. Those of skill in the art will appreciate, in light of the present disclosure and their general familiarity with associated technical methodologies, that modifications and variations may be employed without departing from the spirit and scope of the invention.

EXAMPLE I

Expression of Biologically Active Cytochrome P450$_{17\alpha}$ in E. Coli

In the present Example, the cDNA encoding bovine 17α-hydroxylase (P450,$_{17\alpha}$) was employed to demonstrate the utility of E. coli as an expression system for eukaryotic P450s. This microsomal P450 catalyzes the regio- and stereospecific 17α-hydroxylation of the C21-steroids pregnenolone and progesterone in the pathway leading to the production of cortisol in the adrenal cortex of most mammalian species. P450$_{17\alpha}$ also converts these 17α-hydroxylated products to the C19-androgen precursors of sex hormones via the 17,20-lyase reaction in the gonads of all species of mammals. P450$_{17\alpha}$ (product of the CYP17 gene (Nebert et al., 1989; 1991) is a typical representative of the large number of microsomal P450 enzymes and it is expected that the techniques employed in connection with the bacterial expression of this specific P450 will be generally applicable.

In order to express this P450 in bacteria, the cDNA for the coding region of bovine P450$_{17\alpha}$ (Zuber et al., 1986) was cloned into the *E. coli* expression vector pCW, a derivative of pHSe5 (Muchmore et al., 1989), containing two tac promoter cassettes (Pharmacia #27-4883-01) upstream of Nde I (CATATG) restriction enzyme cloning site coincident with the initiation ATG codon. This vector also contained a strong trp A transcription terminator sequence and the lac I$^q$ gene encoding the lac repressor molecule which prevents transcription from the tac promoters prior to addition of the inducer IPTG. Upon transformation of this expression plasmid containing the native codons of P450$_{17\alpha}$ into the *E. coli* strain JM109, no immunoreactive P450 protein was produced following derepression of the tac promoters.

Figures 2A, 2B:
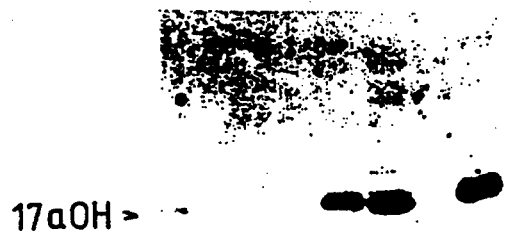
FIG. 2(A): the nucleotide changes (indicated in bold letters) introduced through the use of PCR mutagenesis of plasmid pCD17α-2. The modified amino acid and nucleotide sequences (mod 17) are SEQ ID NO:1 and SEQ ID NO:2, respectively, and the native amino acid and nucleotide sequences (nat17) are SEQ ID NO:4 and SEQ ID NO:5, respectively.
FIG. 2(B): immunoblot analysis of bacterially expressed 17α hydroxylase. Lane 1, 9.4 μg bovine adrenocortical microsomes; lane 2, 50 μg total cell protein (TCP) JM109 (pCWnat17-)+IPTG; lane 3, 50 μg TCP JM109 (pCWmod17) IPTG;—lane 4, 50 μg TCP JM109 (pCWmod17-)+IPTG; lane 5, a mixture of samples in lanes 6 & 7; lanes 6 and 7, 225,000× g supernatant and pellet fractions from a 200 μl culture of JM109 (pCWmod17-)+IPTG, respectively.

Examination of the amino terminal coding sequence of P450$_{17\alpha}$, based on the reports by others that this region may play an important role in expression levels in *E. coli*, led to the introduction of modifications into the cDNA by PCR mutagenesis as indicated in FIG. 2A in an attempt to optimize parameters for the bacterial expression. Specifically, the native second codon was changed from TGG (Trp) to GCT (Ala) a preferred second codon for expression of lac Z (Looman et al., 1987), and codons 4 and 5 were changed to TTA (silent mutations) since this region of *E. coli* mRNAs has been shown to be rich in A and U nucleotides fStormo et al., 1982). Also the last nucleotide of codons 6 and 7 were changed to A and T respectively (silent mutations) to minimize secondary structure formation in the messenger RNA (Scharder et al., 1989).

The nucleotide changes (indicated in bold letters in FIG. 2A) were introduced by means of PCR mutagenesis (Higuchi et al., 1988), amplifying the sequences between the ATG initiator codon and a unique EcoRI restriction site of the plasmid pCD17α-2 (Zuber et al., 1986). Following sequencing of the amplification products, the expression plasmids were constructed by the simultaneous ligation of Nde I/Hind III cleaved pCW vector DNA with a 1257 bp EcoRI fragment containing the native or modified cDNA PCR fragments encoding amino acids 1-91. The final pCW expression plasmids (pCWnat17 and pCWmod17) were subjected to diagnostic restriction enzyme analysis prior to transformation into *E. coli*.

Immunoblot analysis (FIG. 2B) indicated that these alterations had a profound effect on expression of P450$_{17\alpha}$ in *E. coli* and that this expression was efficiently repressed in the absence of IPTG. Fractionation of transformed *E. coli* into membranes and cytosol (Osborne et al., 1974) established that the expressed P450$_{17\alpha}$ was associated with the membranes. JM109 cells harboring the P450$_{17\alpha}$ expression plasmids were grown to an OD$_{550}$=0.4–0.8 in TB broth containing 50-100 μg/ml ampicillin at 37° C. (FIG. 2B). Where indicated, induction of the tac promoters was initiated by 1 mM IPTG. The cells were shifted to 28° C. and gently shaken for 48 hrs, pelleted, washed once in MOPS buffer (50 mM MOPS, 100 mM KCl, 1 mM EDTA, 1 mM DTT, pH 7.5) and resuspended in the same buffer (1/20 volume of the original culture). Lysozyme was added to a final concentration of 0.2mg/ml and the cells were incubated on ice for 30 min. PMSF, leupeptin and aprotinin were added to final concentrations of 1 mM, 0.1 μg/ml and 0.04 U/ml respectively, and the resulting sheroplasts were lysed by sonication in a salt ice bath. Unbroken cells and debris were pelleted at 1,200 xg for 10 min. MgCl$_2$ (6 mM) was added to the supernatant which was centrifuged at 225,000 xg for 30 minutes at 4° C. The resultant membrane pellet was resuspended in MOPS buffer containing 6 mM MgCl$_2$ by gentle homogenization and recentrifuged at 225,000 x g as before. Following centrifugation this washed membrane pellet was resuspended in MOPS buffer. TCP was prepared by boiling cells in 62.5mM Tris-HCl, pH 6.8, 2% SDS. Samples were fractionated on 8% SDS-polyacrylamide gels and transferred to nitrocellulose membranes for immunoblot analysis (Zuber et al., 1985).

Figure 3A:
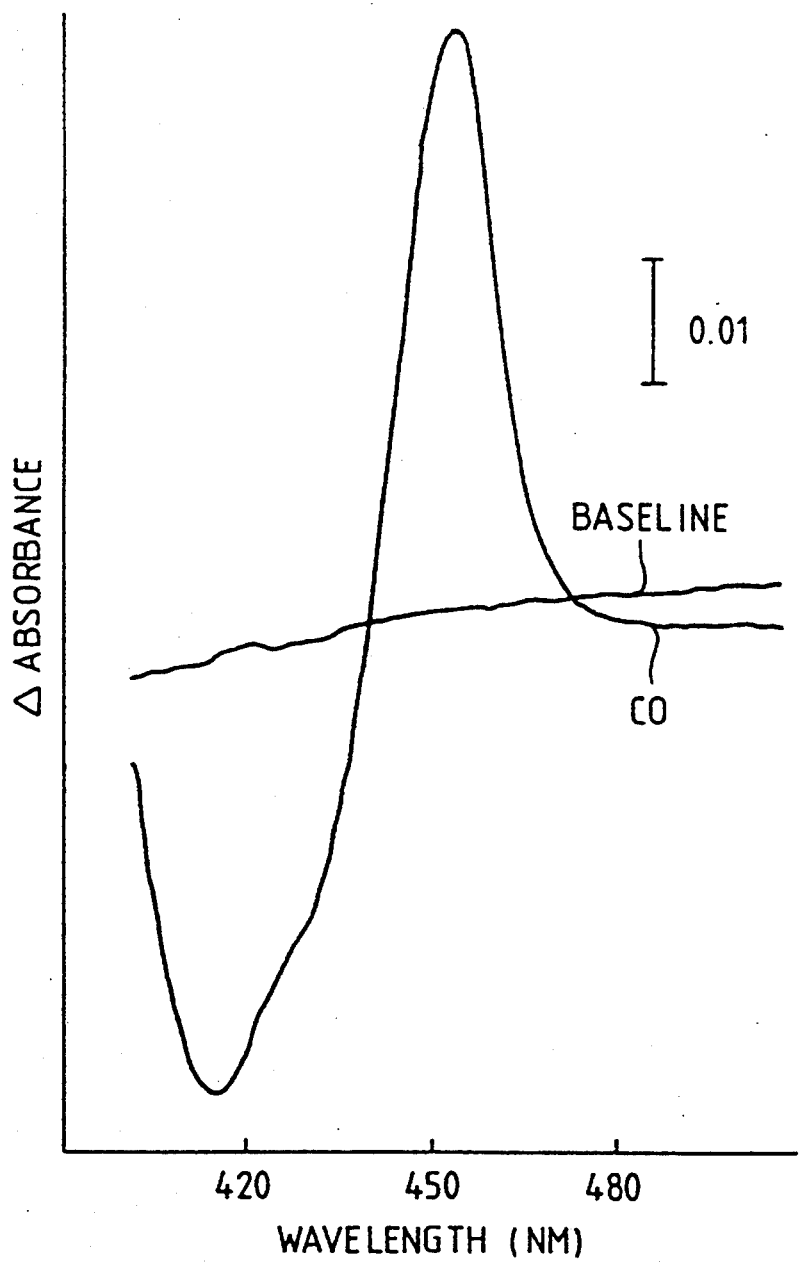
FIG. 3. Reduced CO-difference spectrum (A) and substrate binding spectra (B) of $P450_{17\alpha}$ in intact E. coli cells. Also shown: spectra obtained for bacterially expressed $P450_{17\,\alpha}$, spectrally saturated with steroids and ethanol; and representative baseline tracing recorded from 350 to 510.

Not only was the P450$_{17\alpha}$ protein expressed in *E. coli*, this protein was found to have the spectral characteristics of functional P450$_{17\alpha}$ (FIG. 3A). The reduced CO-difference spectrum obtained in intact *E. coli* showed the characteristic 450 nm absorbance maximum of all cytochromes P450 (Omura et al., 1962). In these studies, 200 ml of JM109 harboring pCWmod17 were cultured and induced as described above for the FIG. 2 studies. Cells were washed and resuspended in 10 ml MOPS buffer. Aliquots of concentrated cells (0.5 ml) were diluted with 5.5 ml of MOPS buffer containing 10mM glucose and divided equally between two cuvettes. Several grains of sodium dithionite were added to each cuvette and the baseline reduced difference spectrum was recorded in an Aminco DW-2A spectrophotometer. Carbon monoxide was then bubbled through the sample cuvette and the reduced-CO bound difference spectrum was recorded.

Figures 1, 3B:
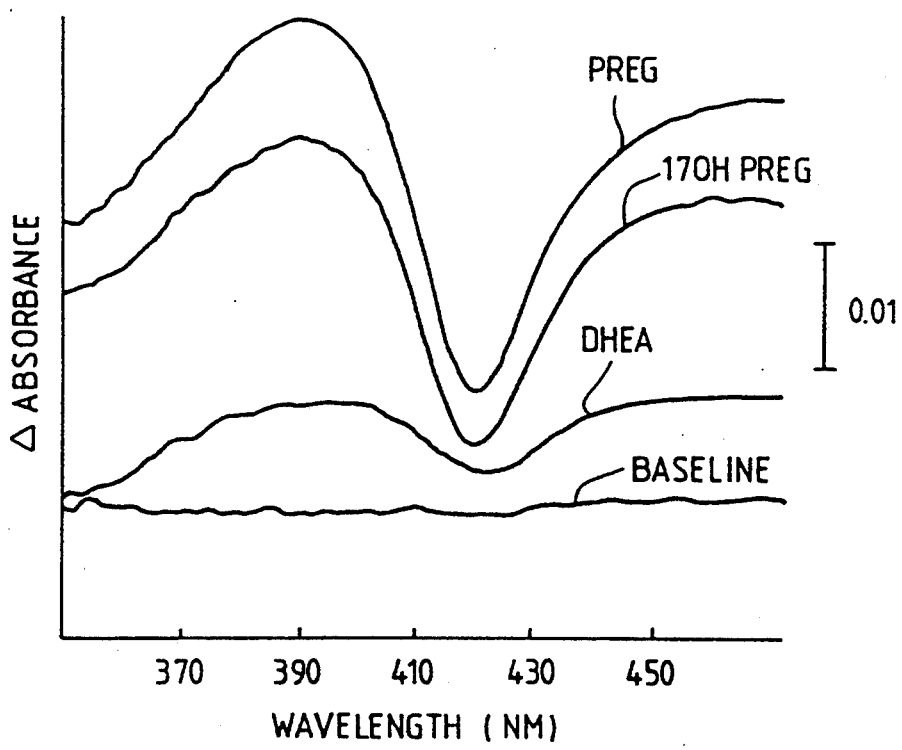
Figures 2, 3B:
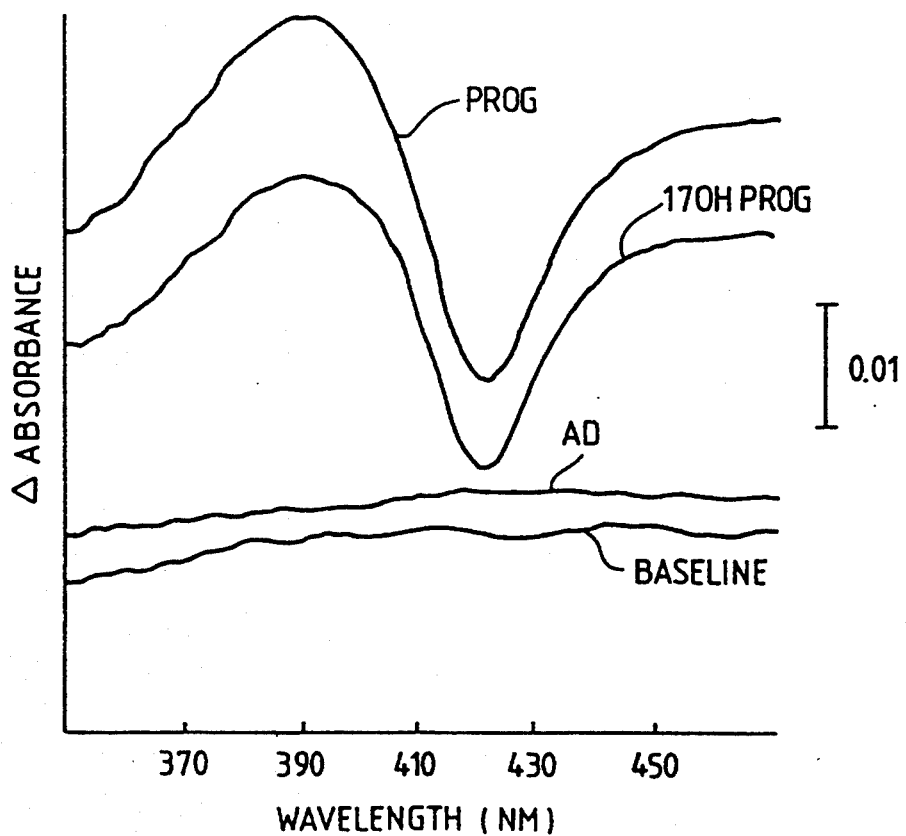
FIG. 2. Nucleotide and amino acid sequences at the 5'-ends of native (nat17) and modified (mod17) $P450_{17\alpha}$cDNAs and their expression in E. coli.

As shown in FIG. 3B, binding of substrates was also observed by detection of substrate-induced difference spectra (Narasimhulu et al., 1965) in intact bacteria following addition of the C21 steroids pregnenolone, progesterone, 17α-hydroxyregnenolone or 17α-hydroxyprogesterone. The C19 steroid product of the 17,20-lyase reaction, dehydroepiandrosterone, showed much less binding while another C19 steroid, androstenedione which is not a product of bovine 17,20-lyase, showed no binding. The functional role of the binding of C21 steroids to the expressed P450$_{17\alpha}$ was determined by incubation of transformed E. coli with radiolabeled substrates and HPLC analysis of substrates and products.

For the studies shown in FIG. 3B, substrate binding spectra were obtained by adding steroid to the indicated final concentration: (preg) pregnenolone 22 μM, (17OH preg) 17α-hydroxypregnenolone 40 μM, (DHEA) dehydroepiandrosterone 46 μM, (AD) androstenedione 46 μM. A volume of washed cells containing 1.6 nmoles P450$_{17\alpha}$ was diluted to 6 ml with MOPS buffer and divided into the sample and reference cuvettes of an Aminco DW-2A spectrophotometer. A baseline tracing was recorded from 350 to 510 nm (representative shown). Steroid was added in 10 μl aliquots (1-2mg/ml in ethanol) to the sample with an equal volume of ethanol added to the reference. Additional aliquots of steroids and ethanol were added until the bacterially expressed P450$_{17\alpha}$ was spectrally saturated (spectra shown).

Figure 4A:
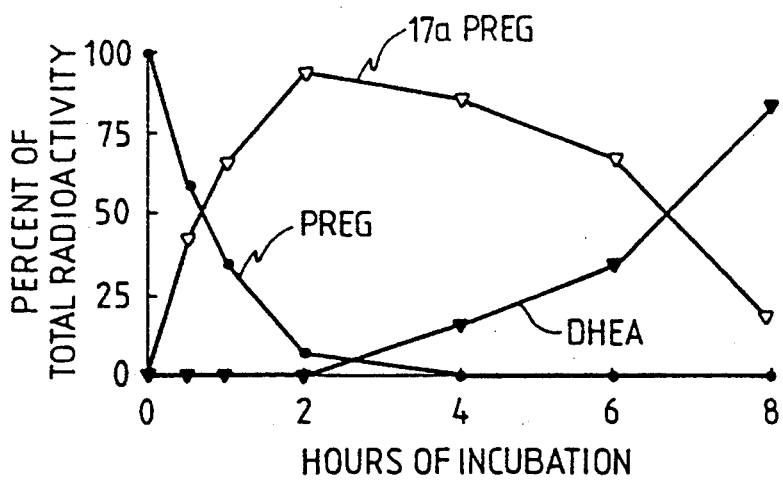
FIG. 4. Steroid metabolism by bacterially expressed bovine 17α-hydroxylase in intact E. coli. Initial substrates were pregnenolone, 17α-hydroxypregnenolone, and progesterone.
Figure 4B:
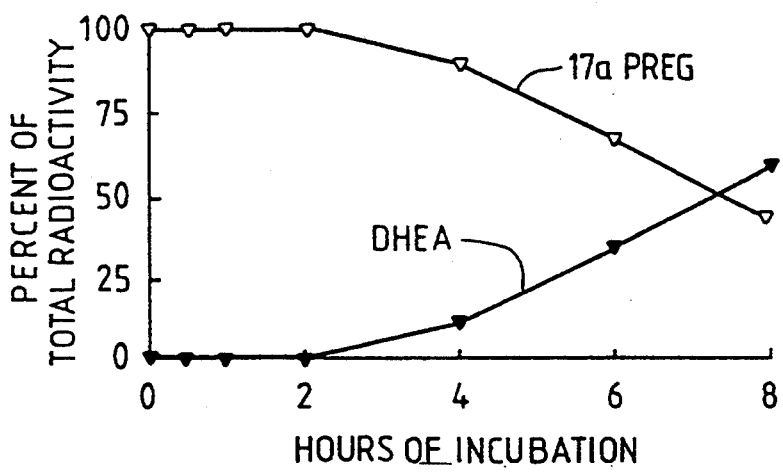
Figure 4C:
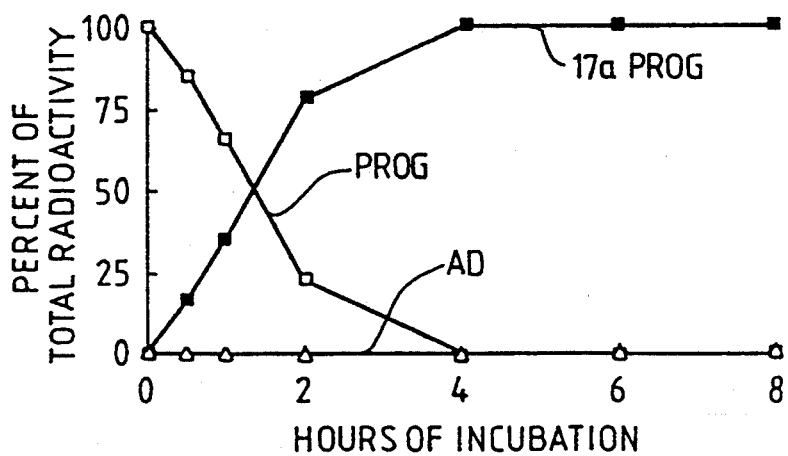

FIG. 4 demonstrates steroid metabolism by bacterially expressed bovine 17α-hydroxylase in intact *E. coli*. The initial substrates employed were pregnenolone, 17α-hydroxypregnenolone, and progesterone. For these studies, E. coli were grown and induced as described for the FIG. 2 studies. Cells were pelleted, washed once in MOPS buffer and resuspended in the same buffer at 1/20 volume of the original bacterial culture. A volume of concentrated cells corresponding to 3.7–4.2 nmoles P450$_{17\alpha}$ was diluted to 5ml MOPS buffer containing 10 mM glucose, 2.5 μM steroid and 100,000 cpm/ml of $^3$H-labeled radioactive steroid. Samples were incubated at. 28° C. with gentle shaking. Aliquots (0.5 ml) were removed at 0, 0.5, 1, 2, 4, 6 and 8 hours after steroid addition. Following extraction of cells and culture media steroids were analyzed by HPLC as previously described (Estabrook et al., 1988). Addition of glucose was not required for metabolism, no significant levels of additional steroid products were observed and ketoconazole, a P450 specific inhibitor (Loose et al., 1983), was found to inhibit 17α-hydroxylase activity.

The enzymatic profile (FIG. 4) of the expressed P450$_{17\alpha}$ in bacteria was the same as observed in other heterologous systems, COS 1 cells (Estabrook et al, 1988) and yeast (Sakaki et al., 1988). Briefly, pregnenolone and progesterone were readily converted to their 17α-hydroxylated products and 17α-hydroxyprogesterone was not converted to androstenedione. Furthermore, when pregnenolone was added as substrate it is first converted almost entirely to 17α-hydroxypregnenolone before 17,20-lyase metabolism occurs. A similar pattern of metabolism is also observed upon expression in COS 1 cells (Estabrook et al., 1988). Consequently bovine P450$_{17\alpha}$ expressed in E. coli was indistinguishable from that expressed in monkey kidney cells or yeast.

Surprisingly, E. coli were capable of supporting the enzymatic activities of P450$_{17\alpha}$ (FIG. 4) without added cytochrome P450 reductase. The flavoprotein, NADPH-cytochrome P450 reductase, is a ubiquitous enzyme in eukaryotic cells which is generally required to support the activity of microsomal P450s. Furthermore P450 reductase from one species is able to support the activity of P450s from other species. However, the presence of this enzyme in E. coli has not been detected immunologically (Porter et al., 1987). A unique form of cytochrome P450 in B. megaterium (P450$_{BM3}$) is found to be a fusion protein between the P450 and a flavoprotein which resembles the eukaryotic P450 reductase in primary sequence, by binding both FAD and FMN and by utilizing NADPH as a source of reducing equivalents. Also, NADPH-sulfite reductase in S. typhimurium and E. coli is a bacterial flavoprotein reported to have properties similar to P450 reductase (Ostrowski et al., 1989). Perhaps sulfite reductase or another E. coli flavoprotein is able to transfer electrons to P450$_{17\alpha}$ localized in the bacterial cell membranes to support these hydroxylation reactions. The present inventor has observed in vitro that 17α-hydroxylase activity can only be reconstituted by mixing membranes and the soluble fraction from transformed E. coli, and is not present in either fraction alone.

These results establish for the first time that a eukaryotic P450 can be expressed in bacteria such as E. coli in a functional form and that strain JM109 is able to support all the known activities of bovine P450$_{17\alpha}$ leading to metabolic profiles indistinguishable from those observed in eukaryotic cells. Consequently, by altering sequences within the first seven codons of the bovine P450$_{17\alpha}$ cDNA to optimize for expression in E. coli, a bacterial expression system has been obtained.

EXAMPLE II

Preferred Growth Conditions

The following have shown to be optimal conditions for the production of P450$_{17\alpha}$ in E. coli.

The starting material is a colony of E. coli strain JM 109 transformed with the plasmid pCWmod17 grown overnight at 37° C. on an LB (Luria Broth) plate (10 g Bacto-Tryptone; 5 g Bacto-Yeast Extract; 5 g NaCl; 15 g Bacto-Agar per liter of H$_2$O) containing 50 μg/ml ampicillin. A single isolated colony is streaked out on a fresh LB Amp plate and grown overnight at 37° C. A single isolated colony from this plate is placed in several ml of LB Amp media (same as above minus Bacto-agar) and grown with vigorous shaking until the culture media reaches an OD$_{600}$ of 0.3. Sterile glycerol is added to this culture for a final concentration of 20%. These cells are frozen at −70° C. in 1 ml aliquots and will serve as inoculum for future experiments.

The standard expression protocol is as follows. Three to five ml of LB Amp media is seeded with several microliters of thawed inoculum. This culture is grown overnight with vigorous shaking at 37° C. This intermediate culture is diluted 1/200 into TB media (24 g/l Bacto-Yeast Extract; 12 g/l Bacto Tryptone; 0.4% Glycerol; 17 mM KH$_2$PO$_4$; 72 mM K$_2$HPO$_4$ (Phosphate added after autoclaving from a 10 fold concentrated stock) containing 50 μg/ml ampicillin. Typically a 500 ml Erlenmeyer flask will contain 50 to 200 ml of media. This inoculated culture is then incubated at 37° C. with vigorous shaking until the OD$_{600}$ of the media is 0.4 to 0.8. At this time the culture is removed and allowed to cool to below 30° C. At this point IPTG (isopropyl-β-D-thiogalactopyranoside) is added from a 100 mM stock for a final concentration of 1 mM. The culture is then transferred to a 30° C. incubator and gently shaken for 48 to 60 hours at which point the level of P450 production is maximal.

Although these conditions have proved adequate to produce bovine 17α-hydroxylase in E. coli several possible adjuvants may lead to improvements in the overall yield. These include but are not limited to the following. Addition of metal salts (Fe, Na, Mg, Mn, Mo etc.), amino acids, glucose and vitamins to the culture media may lead to improved yields especially since strain JM 109 may be impaired in its ability to synthesize the amino acid proline and the vitamin thiamine when grown under the conditions listed above. Another type of media supplement that may improve the production of P450s in bacteria are heme or heme precursors (glutamate or 5-aminolevulinic acid). Since P450s are hemoproteins the synthesis of heme in bacteria may become limited if large amounts of P450 are being synthesized in the cell. Thus, addition of these compounds may counteract this possible limitation.

It may also prove beneficial to add additional aliquots of IPTG to the media during the growth of the culture to insure a proper amount of this inducing agent throughout the long incubation period. Finally, the control of pH and dissolved oxygen in the culture can have a dramatic affect on cell viability and yield of recombinant protein. These parameters are most easily controlled in chemostat culture although the use of alternative buffering agents may suffice to control pH in batch culture. Oxygen tension may be an important parameter since others have reported that high O$_2$ concentrations are deleterious to the stability of 17α-hydroxylase in eukaryotic cells.

EXAMPLE III

Expression of Cytochrome P450 SCC in *E. coli*

The expression of bovine mitochondrial cholesterol side chain cleavage (SCC) in *E. coli* was investigated using the pTRC 99A vector containing a trc promoter and lac ribosome binding site and spacer region was utilized. In eukaryotes, SCC is synthesized as a precursor which then undergoes post translational proteolytic cleavage of the first 39 amino acid residues to form the mature enzyme. An attempt was made to produce both of these forms in *E. coli*. The nucleotide and amino terminal amino acid sequences of these constructs are shown below and represent, in turn, SEQ ID NO:20 and SEQ ID NO:25, respectively:

```
precursor:
ATG GTA GCA AGG GGG CTT CCC CTG CGC TCA GCC CTG GTC AAA GCC TGC CCA CCC ATC
Met  Val Ala Arg Gly Leu Pro Leu Arg Ser Ala Leu Val Lys Ala Cys Pro Pro Ile
 1    2   3   4   5   6   7   8   9   10  11  12  13  14  15  16  17  18  19 mature:
ATG GTC TCC ACA AAG ACC CCT CGC CCC TAC AGT GAG ATC CCC TCC CCT GGT GAC AAT
Met Val Ser Thr Lys Thr Pro Arg Pro Tyr Ser Glu Ile Pro Ser Pro Gly Asp Asn
 *   *   41  42  43  44  45  46  47  48  49  50  51  52  53  54  55  56  57
```

Bold lettering indicates alteration of the native sequences; and the numbers refer to the amino acid sequences of the precursor protein.

When the above sequences were introduced into the pTRC vector, only the mature sequence produced immunoreactive protein as detected in subcellular fractions of these cells. Furthermore, this protein was localized to the *E. coli* membranes, and exhibited a typical reduced CO difference spectra and substrate binding spectra. Initial studies indicated that full enzymatic activity was observed when the bacterially expressed protein was combined in vitro with the electron transport components of bovine adrenal mitochondria. However, other studies indicated that the SCC enzyme was not active in *E. coli* without exogenous reductase. It appeared that the endogenous *E. coli* reductase described earlier could not transfer electrons to SCC produced in this manner. The amount of SCC produced by the pTRC vector was less that the amount of 17α-hydroxylase produced by the pCW vector.

EXAMPLE IV

Expression of Other Cytochrome P450s in *E. coli*

IV. A. Human liver microsomal P450 3A4

The native 5' nucleotide and corresponding N-terminal amino acid sequence of human liver nifedipine oxidase P450 3A4 (Beaune et al., 1986) are shown below and represent SEQ ID NO:24 and SEQ ID NO:25, respectively:

```
ATG GCT CTC ATC CCA GAC TTG GCC ATG GAA ACC TGG CTT CTC CTG GCT GTC AGC CTG
Met Ala Leu Ile Pro Asp Leu Ala Met Glu Thr Trp Leu Leu Leu Ala Val Ser Leu
```

In initial bacterial expression studies the following nucleotide sequences were introduced to create the nucleotide and amino acid sequences, SEQ ID NO:26 and SEQ ID NO:27, represented below:

```
         T                    T
ATG GCT CTC ATT CCG GAT CTG GCT ATG GAA ACC TGG CTT CTC CTG GCT GTC AGC CTG
Met Ala     Ile Pro Asp Leu Ala Met Glu Thr Trp Leu Leu Leu Ala Val Ser Leu
``` with variable third codons of TTT, CTT and a variable seventh codon of TTG or CTG, creating a total of four distinct sequences. When these modified cDNAs were introduced into the pCW vector and transformed into *E. coli* no P450 reduced CO difference spectra was observed. It was then noticed that the 3A4 protein contained several amino acid residues between the N terminal methionine residue and its hydrophobic signal peptide (the region underlined above), whereas in most P450s this hydrophobic region follows immediately after the first methionine residue. Therefore, the following construction was made which contained the first nine codons of the modified 17α-hydroxylase cDNA (lower case) attached at the 21st codon of IIIA4 (capitals) as shown by the nucleotide and amino acid sequences, SEQ ID NO:28 and SEQ ID NO:29, represented below:

```
atg gct ctg tta tta gca gtt ttt ctg GTG CTC CTC TAT CTA TAT GGA ACC CAT TCA
met ala leu leu leu ala val phe leu Val Leu Leu Tyr Leu Tyr Gly Thr His Ser
```

When this cDNA in plasmid pCW was introduced into *E. coli* a characteristic P450 CO difference spectra was observed in these cells indicating high level production of active nifedipine oxidase P450 enzyme.

IV. B. Human liver microsomal P450 1A2

The inventors proposed that while it is possible to "customize" the 5' end of each P450 cDNA to optimize translational efficiency for that sequence, as discussed in detail in Example I, it would be easier to utilize the 5' end of a modified eukaryotic P450 as a "generic" N-terminal sequence for the expression of other eukaryotic P450s in bacteria. The use of such a generic N-terminal sequence would maintain the favorable secondary structural interactions of the resultant mRNA with the ribosome binding region to confer increased expression; and may also aid the correct folding, localization and membrane insertion of cytochrome P450 thus produced.

On aligning a block of 9 amino acids from the N-terminal sequence of bovine 17α-hydroxylase (17A1) with several different cytochrome P450s, a region of homology was identified (FIG. 5). In light of this homology, and the efficient expression of a modified bovine 17A1-human 3A4 hybrid in *E. coli*, the inventors proposed that this sequence may find utility as such a generic N-terminal sequence for the high-level bacterial expression of other cytochrome P450s.

A cDNA for human liver P450 1A2 was cloned from a human liver cDNA λgt11 library by Dr. Linda Quattrochi (Quattrochi et al., 1986). The plasmid pTZ18R was obtained from Pharmacia, and competent *E. coli* DH5α cells were obtained from BRL.

A construct was created to examine the bacterial expression of human P450 1A2 in this manner:

```
                          21  22  23  24  25
Met Ala Leu Leu Leu Ala Val Phe Leu Phe Cys Leu Val Phe
ATG GCT CTG TTA TTA GCA GTT TTT CTG TTC TGC CTG GTA TTC
```

In these nucleotide and amino acid sequences (SEQ ID NO:30 and SEQ ID NO:31, respectively, bold codons indicate the sequence transferred from the modified bovine P450 17A1 to the P450 1A2 cDNA, and the numbering refers to that of the original P450 sequence.

Modifications to the 5' and 3' ends of the cDNA were performed by PCR amplification with primers incorporating the desired sequences which included a Nde I site (CATATG) at the start methionine and an Xba I site 3' to the termination codon. PCR conditions were as follows: 50 mM KCl, 20 mM Tris-HCl, pH 7.5, 1.5 mM MgCl, 50 μM each dNTP, 1.25 U Taq polymerase in a 50 μl reaction volume. Cycling conditions were 94° C., 30 sec; 30° C., 15 sec; 72° C., 30 sec. The reaction was cycled 30 times then extended at 72° C. for 5 min. The reaction product was extracted with chloroform, filled-in with the Klenow fragment of DNA polymerase I, and phosphorylated with T4 kinase. The phosphorylated product was isolated on a low melting point agarose gel and extracted with phenol twice and chloroform once. The PCR product was ligated into the Sma I site of pTZ18R and transformed into DH5α cells. Recombinant colonies were screened by hybridization with $^{32}$P labeled 5' PCR oligonucleotide. The positive clones were sequenced in their entirety with internal oligonucleotide to detect any PCR errors. The Nde I-Xba I fragment was excised from the pTZ18R construct and ligated into pCWori+ which had been digested with Nde I and Xba I. *E. coli* DH5' cells were transformed with the pCWori+ plasmid containing the human P450 insert.

The conditions for the expression of P450 1A2 were modified from those described previously as follows: An overnight culture of the transformed *E. coli* was grown at 37° C. in Luria-Bertani media containing 100 μg/ml ampicillin. A 10 ml aliquot was used to inoculate 1 liter of Terrific broth (Tartof & Hobbs, 1987) containing ampicillin, 1 ml of a mixture of trace elements (Baver & Shiloach, 1974) and 1 mM IPTG. The cells were grown in Fernbach flasks for 72 hours at 30° C. using gentle shaking (125 rpm). The cells were chilled on ice for 1 hour, harvested by centrifugation at 5,000 rpm for 10 minutes, and the pelleted cells washed by resuspending in one fifth the volume of 10 mM potassium phosphate buffer, 0.15M NaCl, pH 7.5, and centrifuging at 10,000 rpm for 10 minutes. This pellet was drained, weighed and the cells resuspended using a Dounce homogenizer with a volume of 75 mM Tris-HCl, 250 mM sucrose, 0.25 mM EDTA, pH 7.5 (TSE buffer) 2-times the wet weight of cells. These cells were divided into 100 ml aliquots and frozen at −70° C.

For the preparation of membranes, cells were thawed and subjected to two-cycles of disruption with a cooled French pressure cell. The disrupted cells were diluted with 2-volumes of TSE buffer and centrifuged at 5,000 rpm for 10 minutes to remove unbroken cells. The supernatant was centrifuged at 100,000 g for 60 minutes, the pellet resuspended in a minimal volume of TSE buffer, divided into aliquots and then stored frozen at −70° C.

On expression of this P450 1A2 hybrid enzyme, a spectrally active P450 enzyme was produced. The level of cytochrome P450 1A2 expression was determined spectrophotometrically by measuring the magnitude of absorbance change at 450nm using an Aminco DW2 Wavelength Scanning Spectrophotometer, following the addition of carbon monoxide to samples to which a few crystals of sodium dithionite had been added, with the exception for in vivo assays where 2 mM glucose was also added to the bacterial suspension.

Figure 6:
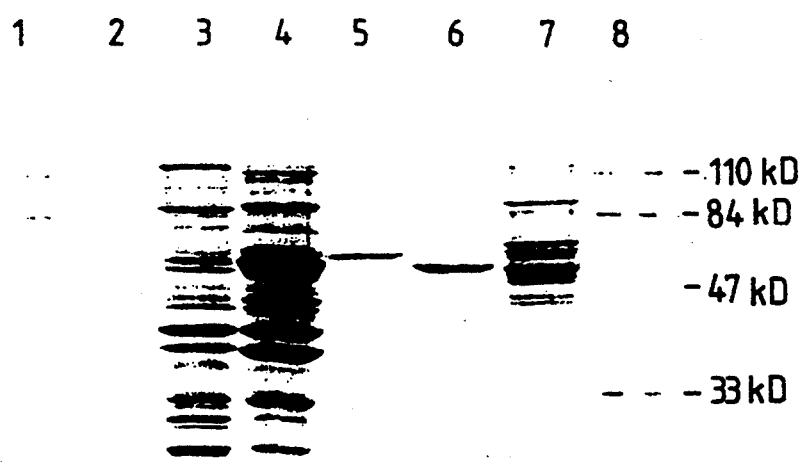
FIG. 6. SDS polyacrylamide (10%) gel electrophoresis of E. coli membranes containing recombinant P450 1A2. Lanes 1 & 8, molecular weight standards of 110k, 84k, 47k, 33k Da; lane 3, 15 μg membrane protein from E. coli transformed with the pCWori+vector with a nonexpressed insert; lane 4, 15 μg membrane protein from E. coli transformed with the pCWori+ vector containing the P450 1A2 modified cDNA; lanes 5 & 6, 1μg purified rat P450 1A1 (form c) and P450 2B1(form b); lane 7, 15 μg rat liver microsomal membranes from β-naphthoflavone treated rats.

Growth in 1 L Fernbach flasks resulted in 1A2 expression of approximately 1000 nmol of spectrophotometrically detectable P450 per litre of growth media (−12 g wet weight of cells). This was calculated to correspond to approximately 4% of the total *E. coli* protein. During disruption of the 1A2-producing cells with the French pressure cell approximately 50% of the spectrophotometrically detectable P450 was lost. However, the membrane fraction, obtained by centrifugation at 100,000 g for one hour, had an average P450 content of about 2nmol/mg of protein (i.e. ∼10% of the membrane protein). High levels of a ∼52kD protein were observed in SDS/PAGE gels of the membrane fraction of 1A2-expressing cells, but not in *E. coli* containing the vector without an insert (FIG. 6). The recombinant P450 1A2 produced by these cells had a similar electrophoretic mobility to rat P450 1A1 and P450 2B1 (FIG. 6). The level of P450 1A2 expression in *E. coli* was determined to be higher than that induced in the livers of rats treated with β-naphthoflavone (see FIG. 6, lane 7) containing an equal protein concentration of liver microsomes from rats treated in this way).

Preliminary studies indicated that about 40% of the recombinant P450 1A2 can be solubilized (i.e. will not sediment after 2 hours of centrifugation at 100,000 g) by the addition of 0.1% Triton X-100 to diluted membrane samples (2mg protein/ml). The ability to solubilize P450 1A2 from the membrane by low concentrations of detergent offers the opportunity to purify large amounts of this human microsomal P450 following expression in bacteria.

Membranes from P450 1A2-expressing *E. coli* were incubated with pure NADPH-cytochrome P450 reductase and the activity for the P450 directed oxidation of a number of substrates was determined.

The hydroxylation of estradiol was assayed using $^3$H labeled estradiol (Aoyama et al., 1989). Briefly, membrane preparations were diluted with 50 mM Tris-HCl, 150 mM KCl, 10 mM MgCl$_2$, 0.1 mM ascorbic acid, pH 7.5, to give 0.5 nmol P450/ml. Purified recombinant rat liver NADPH-cytochrome P450 reductase was added to give a ratio of flavoprotein to P450 of 1:1. The mixture was incubated at 37° C. with mixing for 10 minutes at which time radioactive steroid was added to give final concentrations of between 1 and 25 μM. One minute later the reaction was started by the addition of NADPH (0.3 mM final concentration) and a regenerating system containing 4 mM sodium isocitrate and 0.3 units of isocitrate dehydrogenase. The final volume of the reaction mixture was 6 ml. Aliquots (0.5 ml) were removed at the times indicated and added to 5 ml of methylene chloride, vigorously mixed, extracted, and the organic phase removed and evaporated to dryness with a stream of nitrogen. The sample was dissolved in 100 μl of methanol:water (1:1) containing 1.5 mM ascorbic acid and immediately analyzed by HPLC. Aliquots were automatically injected onto a C18 μBondapak column and metabolites resolved using a 30 minute linear gradient of 70:20:10 (water:methanol:acetonitrile) to 90:10 (methanol:acetonitrile) using a Waters 840 HPLC system connected to a Radiometer Flo-1 radiodetector. The acetonitrile solution contained 1% acetic acid. The eluted products were assayed by tritium detector and their retention times compared with known standards (Aoymam et al., 1989).

Ethoxyresorufin and ethoxycoumarin O-deethylase activities were assayed fluorometrically using an Aminco-Bowman fluorometer as previously described (Burke & Mayer, 1974; Ullrich & Weber, 1972). Reactions were performed at 37° C. in 2 mls of 25 mM Tris-HCl, 150 mM KCl, 10 mM MgCl$_2$, pH 7.4. Substrates were added as DMSO solutions in less than 0.1% of the final volume. The reactions were initiated by the addition of 10 μl of 50 mM NADPH.

The kinetic parameters determined for reactions catalyzed by P450 1A1-containing E. coli membranes, in the presence of purified NADPH-cytochrome P450 reductase, are presented below. Recombinant P450 1A2 was found to be active in the O-deethylation of ethoxyresorufin and ethoxycoumarin and the conversion of estradiol to the 2-OH metabolite.

| Substrate | Vmax | Km |
|---|---|---|
| | (mol/min/mol P450) | (μM) |
| Estradiol | 1.5 | 13 |
| Ethoxycoumarin | 0.36 | 44 |
| Ethoxyresorufin | 2.5 | 0.01 |

Results from further studies indicated that only the 2-hydroxylated estradiol product is formed during the first 5 minutes of the 1A2-catalyzed reaction, using membranes that had not been subjected to repeated freezing and thawing. The initial rate of estradiol metabolism, using a ratio 1:1 ratio of P450 to flavoprotein reductase, was found to be 1 mol/min/mol of P450. This value is similar to that reported for P450 1A2 expressed in human Hep G2 cells by vaccinia virus technology (Aoyama et al., 1990).

Upon incubation times of greater than 15 minutes, or when freeze-thawed membranes were used, the formation of 4-OH estradiol and a more polar unknown metabolite was observed. The generation of water soluble metabolites was most marked when greater than 30–40% of the substrate was converted. It is possible that either the metabolites formed were unstable, or that the properties of the P450 were modified during prolonged incubation. Such an explanation may also account for the late appearance of unknown estradiol metabolites reported by Aoyama et al, (1990).

The influence of varying concentrations of flavoprotein reductase on the rate of O-deethylation of ethoxyresorufin by a fixed concentration of membrane-bound P450 1A2 was investigated. It was determined that, in order to obtain a half-maximal reaction rate, approximately 2.5 molecules of flavoprotein were required for each molecule of P450 1A2. Preliminary studies indicated that this ratio depended upon the composition of the reaction medium, with higher concentrations of salts being required for higher activity.

IV. C. Human liver microsomal P450s 1A1 and 2C8

The bacterial expression of the human microsomal P450s 1A1 and 2C8 was investigated, using the techniques described above, following the construction of hybrids containing the 9 N-terminal amino acids from bovine 17α-hydroxylase, as detailed below:

Human 1A1

```
                                              19   20   21   22   23
Met  Ala  Leu  Leu  Leu  Ala  Val  Phe  Leu  Phe  Cys  Leu  Val  Phe
ATG  GCT  CTG  TTA  TTA  GCA  GTT  TTT  CTG  TTC  TGT  CTG  GTA  TTC
```

Human 2C8

```
                                              16   17   18   19   20
Met  Ala  Leu  Leu  Leu  Ala  Val  Phe  Leu  Leu  Leu  Ser  Leu  Trp
ATG  GCT  CTG  TTA  TTA  GCA  GTT  TTT  CTT  CTC  TTT  TCA  CTC  TGG
```

The cDNA for human liver P450 1A1 was amplified from dioxin induced HEPG2 cells by Dr. Linda Quattrochi. The cDNA for human liver 2C8 (Umbenhauer et al., 1987) was purchased from Dr. Fred Guengerich, Vanderbilt University (Nashville, Tenn.). In these sequences, bold codons indicate the sequence transferred from the modified bovine P450 17A1 to chosen P450 cDNA, and the numbering refers to that of the original P450 sequence. The 1A1 nucleotide sequence is SEQ ID NO:32, and the 2C8 nucleotide and amino acid sequences are SEQ ID NO:33 and SEQ ID NO:34, respectively.

The expression of these two hybrid P450s was also found to be possible in E. coli, and recombinant P450s expressed in this manner were found to be stable in cells frozen at −20° C. for as long as 3 months. The values obtained for the expression of all four P450 17A1-hybrids are presented overleaf.

| P450 | Expression level (nmol/L) |
|---|---|
| 1A1 | 30 |
| 2C8 | 300 |
| 3A4 | 150 |
| 1A2 | 1000 |

Levels of whole cell expression of P450. Hybrid P450 enzymes were introduced into the pCWori+ vector and used to transform E. coli DH5α cells and the cells were induced for expression of P450 in 1 L cultures. The levels of expression of P450 were assayed in whole cells.

However, cytochrome P450s 21A and 19A have not been successfully expressed in hybrid form using similar constructions and methodologies to those described above. The inventors propose that the deletion of codons corresponding to amino acid residues between the initiating methionine and the hydrophobic signal sequences may be necessary in some cases. Studies are in progress to express aromatase and C21 hydroxylase P450s using these guidelines. The aromatase enzyme contains the above mentioned extra peptide sequences while C21 does not.

It should be emphasized, however, that these studies were carried out under conditions that were optimized for the production of P450 17A1 and that no systematic attempt has been made to optimize these parameters for the expression of other P450s. It is known (Lopetzki et al., 1989; Schein et al, 1991) that adjustments in, e.g., inducer titration, oxygen levels and time and temperature of induction, can have a profound affect on the level of production of active recombinant proteins. Thus, for selected cytochrome P450s, one may desire to make moderate alterations in one or more of these parameters in order to achieve optimal expression. The inventors have seen that such factors can have a significant effect on the synthesis of P450 17A1 in $E.$ $coli.$ It would seem likely that these factors would have similar effects on the synthesis of other P450s in $E.$ $coli.$ In preliminary studies utilizing vectors containing modified bovine 17A1 coding sequence downstream of the lac promoter, T7 gene 10 ribosome binding site and spacer sequences the inventors have found that conditions somewhat different from the standard growth conditions discussed above are important for obtaining optimal production of recombinant protein. Specifically, IPTG concentrations as low as 30 μm, higher $O_2$ concentrations in the culture media and harvesting of cells only 6–12 hours after IPTG addition were required for high level production of active bovine 17A1 enzyme in this construct. These factors as well as the temperature at which the cells are grown and induced alter $E.$ $coli$ physiology and growth rate. Thus, it may be important to optimize the variables for each individual P450 enzyme.

The inventors have also noticed differences in recombinant P450 production in different common laboratory strains of $E.$ $coli.$ Other strains besides JM109 and DH52 as well as specially designed protease deficient strains (Gottesman, et al., 1990) should be assayed for their ability to produce these P450 enzymes. Finally, the failure of some P450s to be optimally expressed may be due to the titration of $E.$ $coli$ chaperonin proteins dnak, dnaJ, grpE, cpn10 and cpn60 which may be necessary for the proper folding of some P450s. In these instances, it may be important to overexpress these proteins for efficient P450 production.

In most cases, the procedure of alignment and 17A1-hybrid creation has allowed the successful bacterial expression human P450s in large quantities. It has proven particularly useful in allowing the high-level production of P450 1A2 and 3A4, forms of P450 found in the microsomal fraction of human liver, which can now be used in further detailed structural and functional analyses.

Importantly, these studies also demonstrate that the N-terminal modifications in the hybrid P450s do not interfere with the membrane-binding or catalytic properties of the resultant P450s expressed in bacteria. In other studies, recombinant rat P450 7A and recombinant rabbit P450 2E1 have been expressed without their N-terminal membrane-binding segments and yet have still retained their enzymatic activity (Larson et al., 1991; Li and Chang, 1991). Thus it seems that it is possible to modify the N-terminal segment of P450 proteins without adversely affecting the properties of the resultant expressed protein.

EXAMPLE V

Construction and Expression of P450-Reductase Fusion Proteins

The inventors have investigated techniques that make it possible to express a functional fusion protein comprising a eukaryotic P450 domain fused to a reductase domain in a bacterial system. As examples of this embodiment of the invention, both bovine P450 17A hydroxylase and rat P450 4A1 domains have been fused to rat liver reductase domains in the construction of fusion proteins. It is proposed that these two examples demonstrate the wide breadth of the fusion protein embodiment of the current invention.

V. Bovine P450 17A Hydroxylase-P450 Reductase Fusion Protein

Figure 7:
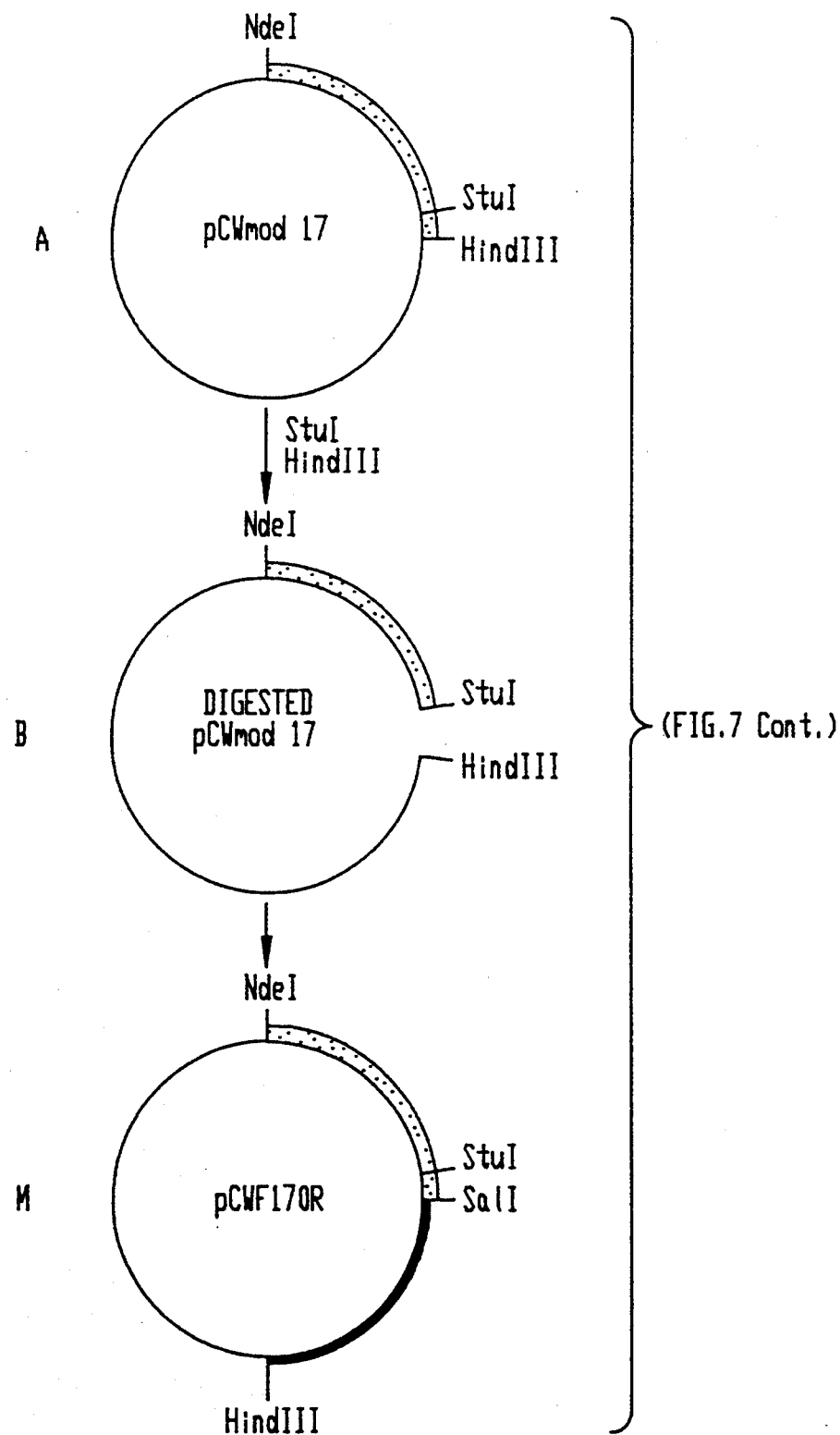
FIG. 7. A figure detailing the construction of a fusion of a DNA segment encoding a bovine P450 17A domain and a DNA segment encoding a rat liver P450 reductase domain. Steps in the modification of P450 reductase and the 3' end of the bovine P45017A are outlined.
Figure 7:
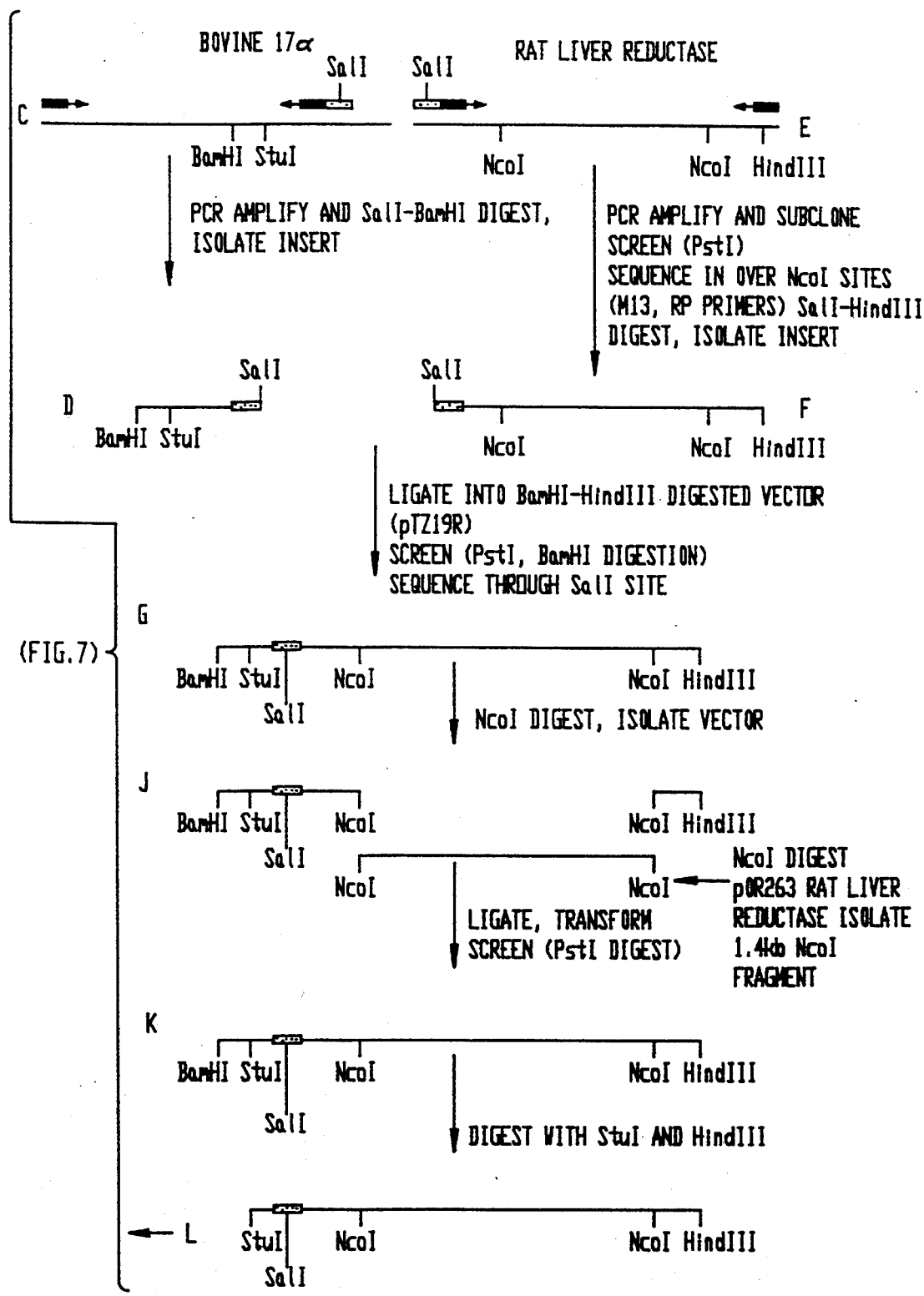

In one exemplary embodiment of the fusion protein embodiment of the invention, a plasmid containing a DNA segment encoding a bovine P450 17A1 reductase domain was fused to a DNA segment encoding a rat liver reductase domain by PCR mutagenesis. FIG. 7 outlines the construction of the fusion protein gene. In this exemplary embodiment, mutagenesis was performed to modify the coding sequence of both the carboxy-terminus of the bovine cytochrome P450 17A1 domain and the coding sequence for the amino-terminus of the rat liver reductase domain. These modifications allowed the fusion of these two domains with a SerThr dipeptide linker. FIG. 8(A) details the DNA sequence and deduced amino acid sequence of the linker region fusion between the encoded bovine P450 17A1 domain and the encoded rat cytochrome c reductase domain. In accordance with standard techniques, all regions constructed by PCR amplification were sequenced to ensure the integrity of the amplified sequence. Furthermore, to the degree possible, unmodified regions amplified by PCR were replaced with original plasmid derived DNA.

The bovine P450 17A1 domain utilized in the construction of this fusion protein gene was obtained by using the construct expressing bovine P450 17A1 in the pCWori+ vector (pCWmod17) as a starting material. This plasmid was digested at the methylated Stu I site by transforming it into the dcm-$E.$ $coli$ strain GM48 and preparing plasmid DNA. Digestion of the plasmid with Stu I and Hind III resulted in the deletion of a 40 bp fragment.

The DNA segment encoding the rat liver reductase domain utilized in this embodiment of the fusion protein was obtained from rat liver reductase cDNA. This rat liver reductase cDNA was PCR amplified using primers that deleted the amino-terminal membrane anchor region and incorporated a Sal I site which encoded SerThr as a linker region. The 3' reductase primer selected incorporated a Hind III site after the TAG stop codon. The PCR fragment was then subcloned into the Sma I site of pTZ19R. Finally, the 5' and 3' ends of the amplified sequenced were sequenced to the two internal Nco I sites.

The segment encoding the bovine P450 17A1 domain was PCR amplified with a 3' primer deleting the TGA codon and incorporating the same Sal I site encoding SerThr as the reductase 5=primer. This PCR product was then digested with BamH I and Sal I. Subsequently, the Sal I - Hind III reductase domain was ligated to the BamH I - Sal I P450 domain fragment and then PTZ19R digested with BamH I and Hind III. A positive clone was isolated and insequenced from the Stu I site to the Sal I site in the P450 domain.

The positive clone was digested with Nco I to remove the 1.4 kb internal Nco I - Nco I fragment from the PCR generated reductase domain. This 1.4 kb fragment was isolated from a plasmid preparation of the original rat reductase cDNA. The Nco I fragment was then ligated with the Nco I deleted vector construct. A construct with a replaced Nco I fragment in the correct orientation was identified and transformed into E. coli GM48 and digested with Stu I and Hind III. The resulting 1.9 kb Stu I - Hind III fragment was ligated with the original encoded bovine P450 17A1 domain in pCWori+ digested with Stu I - Hind III.

Positive colonies which contained the plasmid encoding for the fusion protein were identified by restriction digestion. These colonies were subsequently grown in liquid culture for expression as previously described and were screened for spectrally detectable P450 and cytochrome c reductase activities.

The fusion protein was expressed in E. coli at a level of approximately 100 nmol/liter of growth media under conditions described previously in the application. This level is approximately 20% of the level of expression obtained for bovine 17-hydrolase cytochrome P450 domain alone. The fusion protein was present in the membrane fraction of the disrupted E. coli cells and could be solubilized using detergents. In the present example, purification of the fusion protein was achieved by chromatography on DE-52 and 2', 5' ADP-sepharose. SDS-PAGE analysis suggested that the obtained fusion protein had a molecular weight of about 118 kd.

Figure 10:
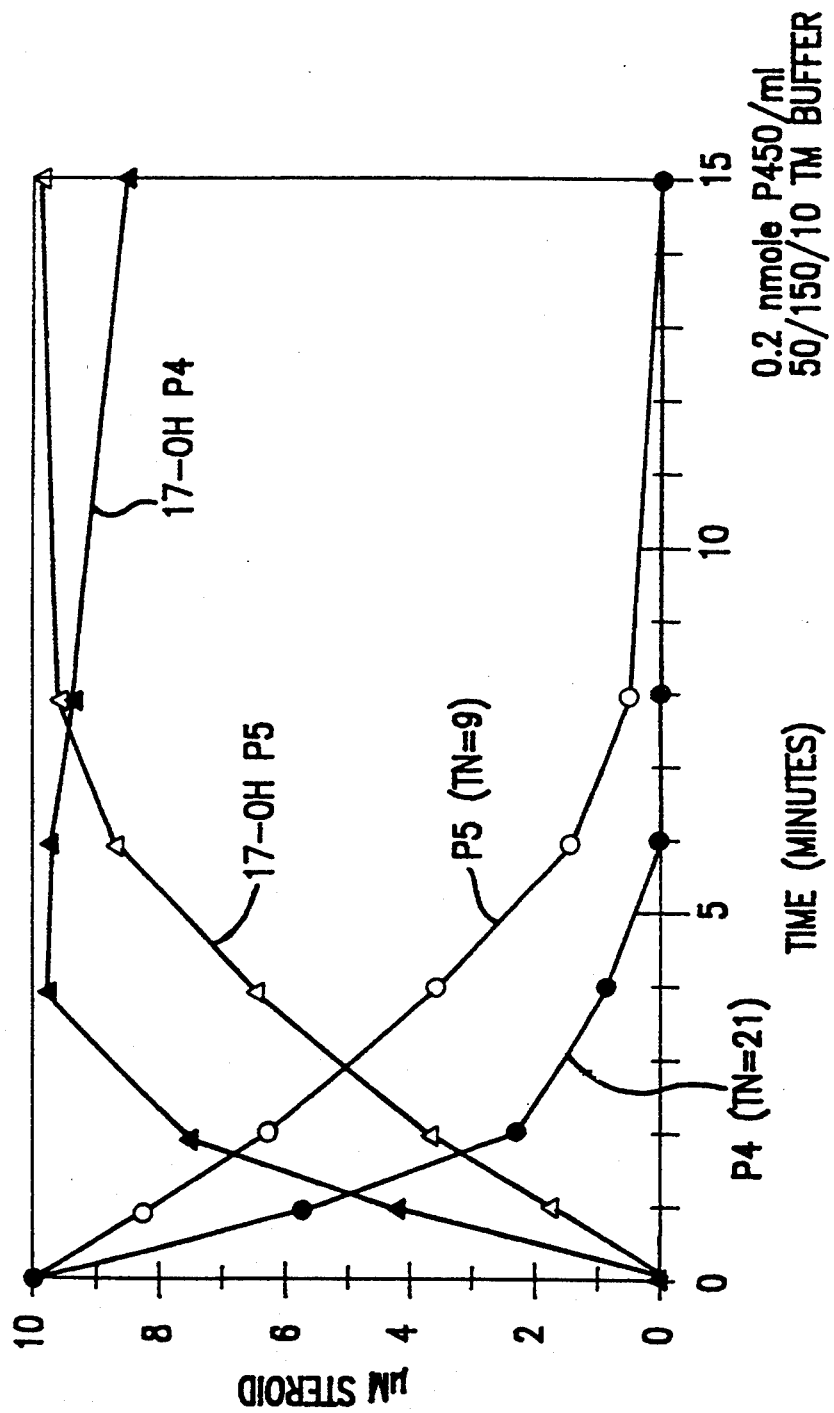
FIG. 10. Graph showing the enzymatic properties of the purified fusion protein obtained by fusing bovine 17A1 P450 domain to a rat cytochrome C reductase domain. The membrane-bound form of the fused enzyme is competent in catalyzing the 17α-hydroxylation of both progesterone and pregnenolone, albeit at a rather slow rate. Further, the membrane-bound fused enzyme appears to have lost one of the characteristics of the bovine P450 17α-hydroxylase by its inability to catalyze the lyase reaction for the oxidation of 17α-hydroxypregnenolone to dehydroepiandrosterone.
Figure 11A:
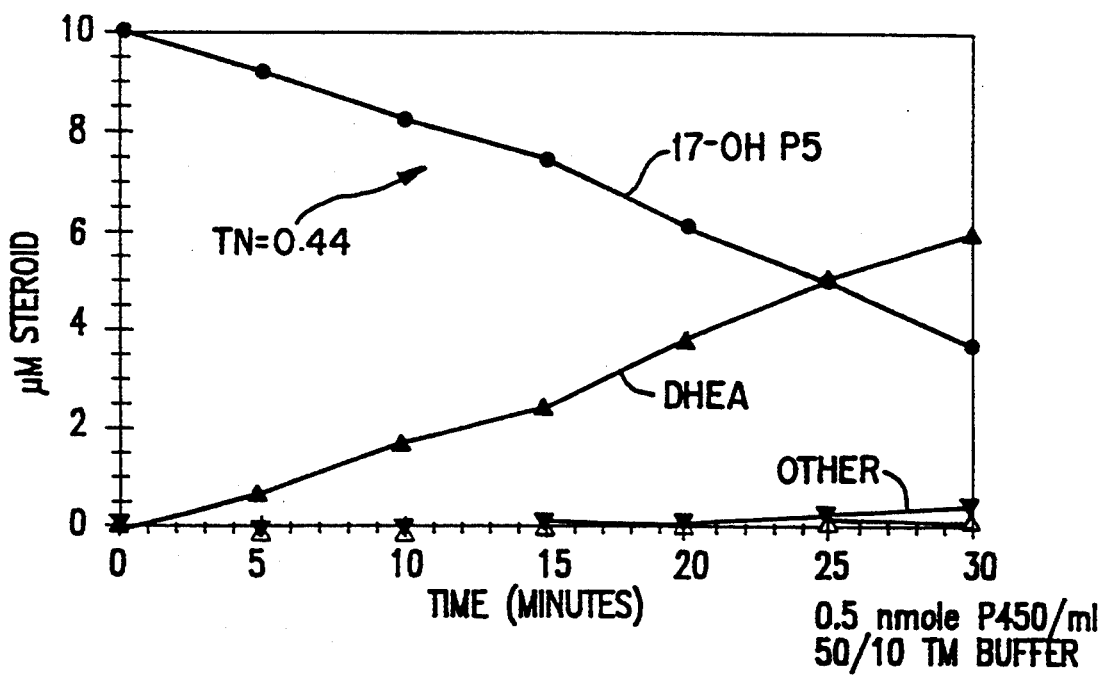
FIG. 11. (A) Graph showing that when 17α-OH P5 is incubated with the fusion protein, DHEA is formed in a time dependent manner. (B) Chromatography analysis showing the metabolites formed from the metabolism of 17-OH P5 by the fusion protein. Note that small amounts of metabolites other than DHEA are produced by metabolism by the fusion protein. Analysis was performed with reverse phase HPLC chromatography on a C18 column.
Figure 11B:
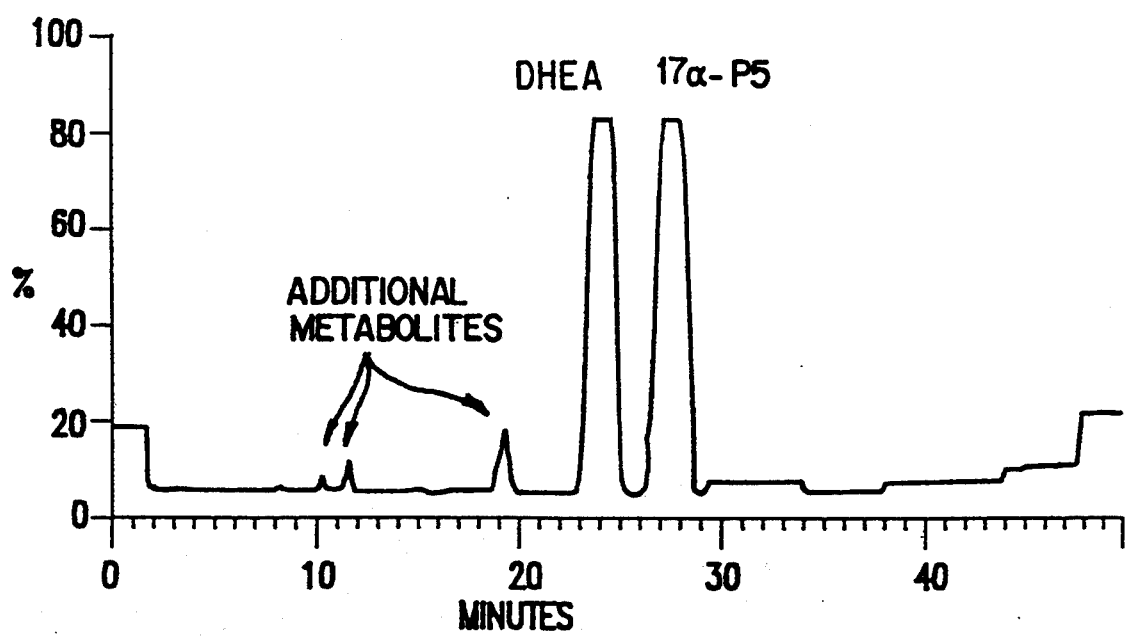
Figure 12A:
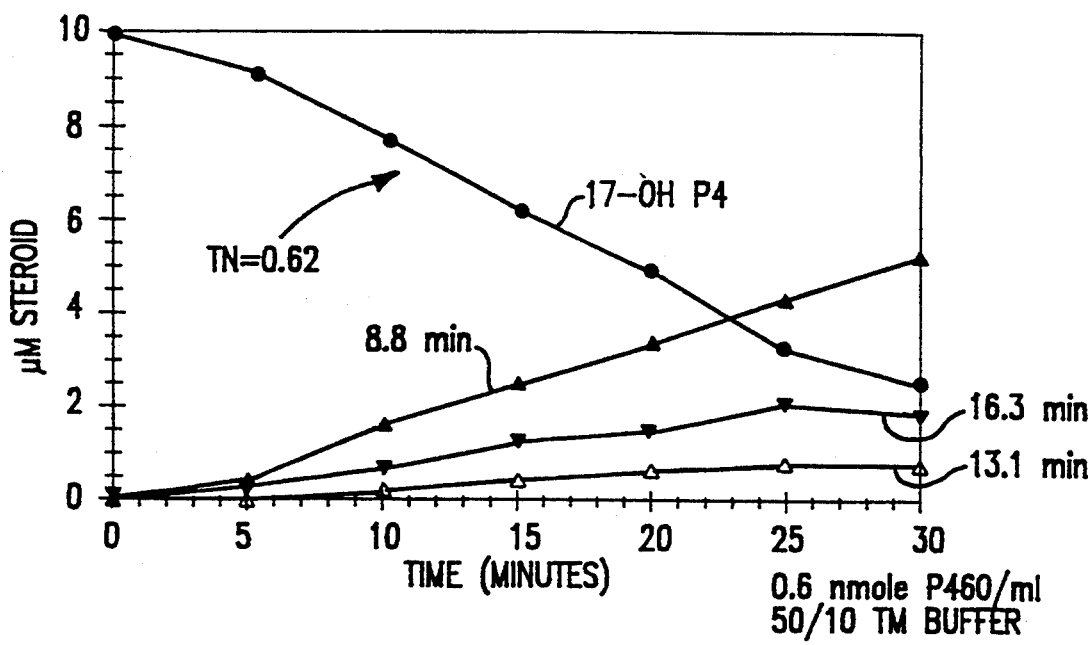
FIG. 12. (A) Graph showing the fusion protein ability to metabolize 17α-OH P4 to three distinct metabolites at a rate equivalent to that seen for the metabolism of 17α-OH P5. (B) Data from reverse phase HPLC chromatography on a C18 column showing that three distinct metabolites are formed from the metabolism of 17α-OH P5, and suggesting that new enzymatic activities, which are different from those which are in the native P450 enzyme, have been introduced in the fusion protein.
Figure 12B:
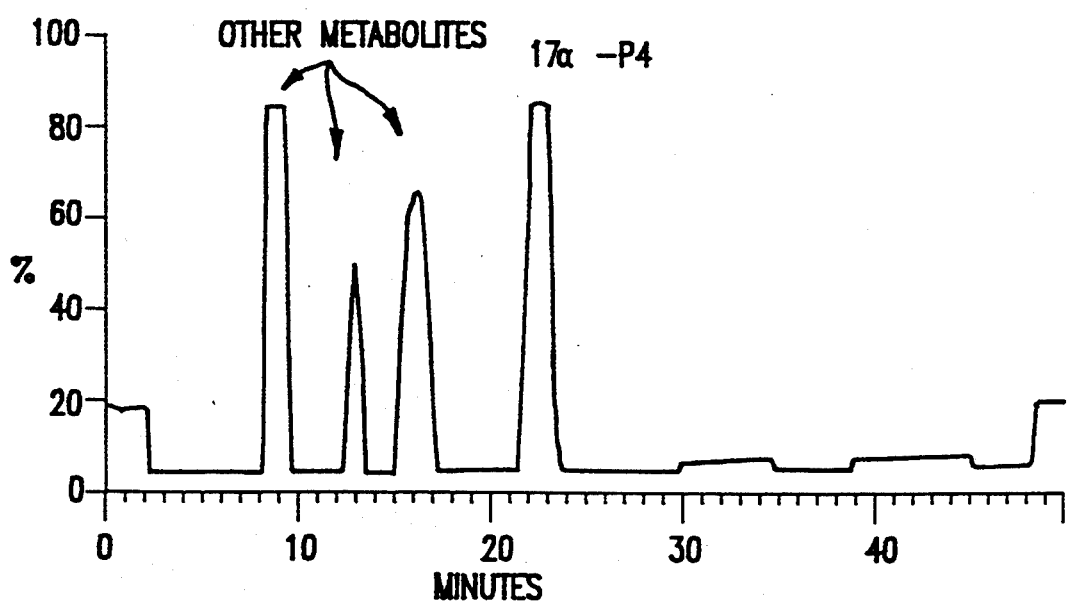

The bovine P450 17A1- rat liver reductase fusion protein exhibited spectrally detectable P450 and cytochrome reductase activities as detailed in FIGS. 10-12. In FIG. 10, a graph shows the enzymatic properties of the fusion protein obtained by fusing bovine 17A1 P450 domain to rat cytochrome c reductase domain. The fused enzyme is shown to be competent in catalyzing the 17 α-hydroxylation of both progesterone and pregnenolone, albeit at a rather slow rate. Further, the membrane-bound fusion protein appears to have lost the ability to catalyze the lyase reaction for the oxidation of 17 α-hydroxypregnenolone to dehydroepiandrosterone, which is one of the characteristics of native bovine P450 17 α-hydroxylase. Only after prolonged incubation times was there any suggestion of such activity. The bovine P450 17 α-hydroxylase is known to have no detectable activity for the conversion of 17 α-OH p4 to androstenedione, and it is included as a control in FIG. 10.

In FIG. 11, the purified fusion protein shows a remarkably high enzymatic activity when incubated with NADPH and either progesterone or pregnenolone. In both instances, the primary product formed is a 17 α-hydroxy-metabolite. However, after long incubation times there is evidence of the formation of other metabolites. When 17 α-OH P5 is incubated with the fusion protein, DHEA is formed in a time dependent manner, this is shown in FIG. 11(A). In addition to DHEA, small amounts of other, as yet unknown metabolites are formed after long incubation times, this is shown most readily in the chromatography analysis seen in FIG. 11(B).

FIG. 12 graphically shows the fusion protein's ability to metabolize 17 α-OH P4 to three distinct metabolites at a rate equivalent to that seen for the metabolism of 17 α-OH P5. This activity is not seen in the native P450 enzyme from which the domain used in the creation of this fusion protein was isolated, therefore new enzymatic activities have been introduced during the creation of the fusion protein.

V. B. Rat P450 ω-Hydroxylase-P450 Reductase Fusion

One of the particularly useful aspects of the fusion protein constructs generated in this embodiment of the inventions is that many of them can contain unique restriction sites which allow for the facile interchange of other P450 domains. Thus, the inventors were able to substitute rat P450 4A1 for the bovine P450 17A1 in the above described construct. The results of this interchange was expression of an enzymatically functional fusion protein consisting of a rat P450 4A1 domain fused to rat liver P450 reductase.

The DNA sequence encoding a rat P450 4A1 domain was constructed using PCR mutagenesis. In FIG. 9, a diagram shows the modifications of the amino terminal or the rat P450 4A1, which were necessary to accomplish this fusion. In order to allow the fusion of this sequence to the rat liver reductase domain encoding sequence with the same dipeptide linker of SerThr previously employed, mutagenesis was performed to modify the coding sequence of the amino-terminus and carboxyl-terminus of the rat cytochrome P450 4A1 encoding DNA segment. (see FIG. 8(B)).

In particular, the DNA segment encoding the rat liver ω-hydroxylase (P450 4A1) was prepared as follows. cDNA containing the P450 4A1 domain encoded in it was PCR amplified. The 5' primer utilized deleted a portion of the amino-terminal region of this DNA segment and replaced it with a 27 bp fragment of modified bovine P450 17A1 sequence, which has proved particularly useful in allowing bacterial expression of eukaryotic P450 domains. The 3' primer utilized incorporated a Xho I site encoding SerThr as a linker, thereby replacing the TAA stop codon. This PCR product was then digested with Nde I and Xho I. The bovine 17A1-rat P450 reductase fusion protein constructed in the above example was then digested with Nde I and Sal I to remove the P450 domain. The presence of the Sal I restriction enzyme site in the SerThr linker region greatly facilitated the removal of the bovine P450 domain. A plasmid containing solely the rat liver reductase domain was then ligated with the Nde I - Xho I PCR amplified rat P450 4A1 domain. A construct with the replaced Nde I - Xho I fragment in the correct orientation was identified by restriction digestion and transformed into E. coli cells.

Positive clones containing the rat P450 4Al-rat liver reductase fusion protein were identified by restriction digestion. Colonies were grown in liquid culture as previously described, and the expressed fusion protein exhibited spectrally detectable P450 and reductase activities in much the same manner as the bovine P450-rat reductase fusion protein.

While the compositions and methods of this invention have been described in terms of preferred embodiments, it will be apparent to those of skill in the art that variations may be applied to the compositions, methods, and in the steps or in the sequence of steps of the methods described herein without departing from the concept, spirit and scope of the invention. More specifically, it will apparent that certain agents which are both chemically and physiologically related may be substituted for the agents described herein while the same or similar results would be achieved. All sets of similar substitutes and modifications apparent to those skilled in the art in light of the present disclosure are deemed to be within the spirit, scope, and concept of the invention as defined by the appended claims.

REFERENCES

The references listed below are incorporated herein by reference to the extent that they supplement, explain, provide a background for or teach methodology, techniques and/or compositions employed herein.

Aoyama, T., Gonzalez, F. J., Gelboin, H. V., (1989) *Mol. Carcinog.* 2, 192–198.

Aoyama, T., Korzekwa, K., Nagata, K., Gillette, J., Gelboin, H. V. and Gonzalez, F. J. (1990) *Endocrinology* 126, 3101–3106.

Argos, P. (1989) An investigation of oligopeptides linking domains in protein tertiary structures and possible candidates for general gene fusion. *J. Mol. Biol.* 211, 943–958.

Asseffa, A., Smith, S. J., Nagata, K., Gillette, J., Gelboin, H. V. and Gonzalez, F. J. *Arch. Biochem. Biophys.* 274, 481–490 (1989).

Bachmair, A., Finley, D. and Varshansky, A. (1988), *Science*, 234:179–186.

Barnes, H. J., Arlotto, M. P. and Waterman, M. R. (1991), Expression and enzymatic activity of recombinant cytochrome P450 17α-hydroxylase in *Escherichia coli. Proc. Natl. Acad. Sci.* 88, 5597–5601.

Battula, N., Sagara, J. and Gelboin, H. V. (1987), *Proc. Natl. Acad. Sci. U.S.A.* 84, 407–4077.

Baver, S., and Shiloach, J. (1974) *Biotechnol. Bioengin.*, 16, 933–941.

Beaune, P. H. et al. (1986), *Proc. Natl. Acad. Sci. U.S.A.*, 83:8064–8068.

Burke, M. D. and Mayer, R. T. (1974) *Drug Metabol. Disp.* 2, 583–588.

Chen, G. F., and Inouye, M. (1990), *Nuc. Acids Res.*, 18:1465–1473.

Cullin, C., and Pompom, D. (1988), *Gene* 65:203–217.

Dalboge, H., et al. (1990), *FEBS Letts.*, 266:1–3.

Danayotatos, N., and Trvong, K. (1985), *Nucl. Acids Res.*, 7:2227–2240.

DeBoer, H. A., and Hri, A. S. (1990) *Methods in Enzymology*, Volume 185 Chapter 9, Academic Press, Inc., pp. 103–114.

Dreyfus, M. (1988) *J. Mol. Biol.*, 204:79–94.

Earnshaw, D., Dale, J. W., Goldfarb, P. S. and Gibson, G. G. (1988) Differential splicing in the 3' non-coding region of rat cytochrome P452 (P450 IVA) mRNA. *FEBS Lett.* 236, 357–361.

Estabrook, R. W., Mason, J. I., Martin-Wixtrom, C., Zuber, M. and Waterman, M. R. in *Oxidases and Related Redox Systems* (Eds., King, T. E., Mason, H. S. and Morrison, M.) 525–540 (Alan Liss, Inc., New York, 1988).

Fisher, C. W., Caudle, D. L., Martin-Wixtrom, C., Quattrochi, L. C., Tukey, R. H., Waterman, M. R. and Estabrook, R. W. (1992) High-level expression of functional human cytochrome P450 1A2 in *Escherichia coli. FASEB J.* 6, 759–764.

Gelboin, H. V. (1980), *Physiol. Rev.* 60:1107–1165.

George, H. J., L'italien, J. J., Pilacinski, W. P., Glassman, D. L. and Krzyzek, R. A. (1985) *DNA* 4, 273–281.

Gold, L., and Stormo, G. (1987), Chapter 78 in *Eschericia coli and Salmonella triphimerium Cellular and Molecular Biology*, F. C. Weidhardt, ed., p. 1302–1307, American Society for Microbiology. Washington, D.C.

Gotoh, O., Tagashira, Y., Iizuka, T., and Fujii-Kuriyama, Y. (1983), *J. Biochem. (Tokyo)*, 93:807–817.

Gottesman, S. (1990) *Meth. Enzy.*, 185:119–129Gren (1984), *Biochimie*, 66:1–29

Hall, P. F. (1980), *Vitam. Horm.*, 42:315–360.

Hansson, R., and Wikrall, K. (1980), *J. Biol. Chem.*, 755:1643–1649.

Hawley, D. K., and McClure, W. R. (1983), *Nuc. Acids Res.*, 11:2237–2255

Higuchi, R., Krummel, B. and Saiki, R. K. *Nucleic Acids Res.* 16, 7351–7367 (1988).

Hirtel, P. H., et al., (1989), *Proc. Natl. Acad. Sci. U.S.A.*, 86:8247–8751.

Hoopes, B. C. and McClure W. R. (1987), Chapter 75 in *Escherichia coli and Salmonella triphimurium Cellular and Molecular Biology*, F. C. Neidhardt, ed., p. 1231–1240, American Society for Microbiology, Washington, D.C.

Jaeger, et al. (1989), *Proc. Natl. Acad. Sci. U.S.A.*, 86:7706–7710.

Katagiri, M., Ganguli, B. N., and Gunsalus, I. C. (1988) *J. Biol. Chem.*, 243:3543–3546.

Kupfer, D. (1980), *Pharmacol. Ther.*, 11:469–496.

Looman, A. C., Bodlaender, J., Comstock, L. J., Eaton, D., Thurani, P., de Boer, H. A., and Van Knippenberg, P. H. *EMBO J.* 6, 2489–2492 (1987).

Loose, D. S., Kan, D. B., Hirst, M. A., Markus, R. A. and Feldman, D. (1983) *J. Clin. Invest.* 71, 1495–1499.

Lopetzki, E., Schumacher, G. and Buckel, P. (1989) *Mol. Gen. Genet.* 216, 149–155.

Lu, A. Y. H., and West, S. B. (1980), *Pharmacol. Rev.*, 31:227–295.

McCarthy, J. E. G., and Gualerzi, C. (1990) *Trends in Genetics*, 6:78–85.

McManus, M. E., Burgess, W. M., Veronese, M. E., Huggert, A., Quattrochi, L. C. and Tukey, R. H. (1990) *Cancer Research* 50, 3367–3376.

Muchmore, D. C., Mcintosh, L. P, Dahlquist, F. W. (1989) *Meth. Enzymol.* 177, 44–73.

Murakami, H., Yabusaki, Y., Sakaki, T., Shibata, M. and Ohkawa, H. (1987) A genetically engineered p450 monooxygenasee: Construction of the functional fused enzyme between rat cytochrome p450c and NADpH-cytochrome p450 reductase. *DNA* 6, 189–197.

Narashimhulu, S., Cooper, D. Y. and Rosenthal, D. (1965) *Life Sci.* 4, 2101–2107.

Nebert, D. W., Nelson, D. R., Adesnik, M., Coon, M. J., Estabrook, R. W., Gonzalez, F. J. Guengerich, F. P., Gunsalus, I.C., Johnson, E. F., Kemper, B., Levin W., Phillips, I. R., Sato, R. and Waterman, M. R. (1989) *DNA* 8, 1–13.

Nebert, D. W., Nelson, D. R., Coon, M. J. Estabrook, Feyereisen, R., Fujii-Kuriyama, Y., Gonzalez, F. J., Guengerich, F. P., Gunsalus, I. C., Johnson, E. F., Loper, J. C., Sato, R., Waterman, M. R. and Waxman, D. J. (1991) *DNA Cell Biol.* 10, 1–14.

Nelson, D. R. and Strobel, H. W. (1988) On the membrane topology of vertebrate cytochrome P0450 proteins *J. Biol. Chem.* 263, 6038–6050.

Oeda, K., Sakaki, T. and Ohkawa, H. (1985) *DNA* 4, 203–210.

Ohkawa, H., Yabusaki, Y., Sakaki, T., Murakami, H. and Shibata, M. (1989) Expression of cytochrome P-450 and NADPH-cytochrome P-450 reductase genes in yeast. In *Xenobiotic Metabolism and Disposition*, Eds. Kato, R., Estabrook, R. W. and Cayen, M. N., New York.

Osborn, M. J. and Munson, R. (1974) *Meth. Enzymol.* 31A, 642–653.

Ostrowski, J., Barber, M. J., Rueper, D. C., Miller, B. E., Siegel, L. M. and Kredich, N. M. (1989) *J. Biol. Chem.* 264, 15796–15808.

Peterson, G. B., Stockwell, P. A. and Hill, D. F. (1988), *EMBO J.*, 7:3957–3962.

Porter, T. D., Wilson, T. E. and Kasper, C. B. (1987), *Arch. Biochem. Biophys.* 254, 353–367.

Rosenberg, M. and Court, D. (1979), *Ann. Rec. Genet.*, 13:319–353.

Sakaki, T., Shibata, M., Yubasaki, Y., Murakami, H. and Ohkawa, H. (1989), *DNA* 8, 409–418.

Sakaki, T., Shibata, M., Yabusaki, Y., Murakami, H. and Ohkawa, H. (1990) Expression of bovine cytochrome P450C21 and its fused enzymes with yeast NADPH-cytochrome P450 reductase in *Saccharomyces cerevisiae. DNA Cell Biol.* 9, 603–614.

Schauder, B. and McCarthy, J. E. G. (1989), *Gene* 78, 59–72.

Schein, C. (1991) *Curr. Opin. in Biotech.*, 2, 746–750.

Schoner, B. E., Hsiung, H. M., Belagaje, R. M., Mayne, N. G., and Schoner, R. G. (1984) *Proc. Natl. Acad. Sci. USA* 81, 5403–5407.

Sesardic, D., Cole, K. J., Edwards, R. J., Davies, D. S., Thomas, P. E., Levin, W., and Boobis, A. R. (1990) *Biochem. Pharmacol.* 39, 499–506.

Shen, A., Porter, T. D., Wilson, T. E. and Kasper, C. B. (1989) Structural analysis of the FMN binding domain of NADPH-cytochrome P-450 oxidoreductase by site-directed mutagenesis. *J. Biol. Chem.* 264, 7584–7589.

Shibata, M., Sakaki, T., Yabusaki, Y., Murakami, H. and Ohkawa, H. (1990) Genetically engineered P450 monooxygenases: Construction of bovine P450c17/yeast reductase fused enzymes. *DNA* 9, 27–36.

Stormo, G. D., Schneider, T. D. and Gold, L. D. (1982), *Nucleic Acids Res.* 10, 2971–2996.

Tartof, K. D. and Hobbs, C. A. (1987), *Focus* 9:2, 12.

Ullrich, V. and Weber, P. (1972) *Hoppe-Seyler's Z. Physiol. Chem.* 353, 1171–1177.

Umbenhauer, D. R., Martin, M. V., Llyod, R. S., and Guengerich, F. P. (1987), *Biochemistry* 26, 1094–1099.

Unger, B. P., Gunsalus, I. C. and Sligar, S. G. (1986), *J. Biol. Chem.* 261, 1158–1163.

Yabusaki, Y., Murakami, H., Sakaki, T., Shibata, M. and Ohkawa, H. (1988) Genetically engineered modification of P450 monooxygenases: Functional analysis of the amino-terminal hydrophobic region and hinge region of the P450/reductase fused enzyme. *DNA* 7, 701–711.

Zuber, M. X., Simpson, E., Hall, P. F. and Waterman, M. R. (1985), *J. Biol. Chem.* 260, 1842–1848.

Zuber, M. X., John, M. E., Okamura, T., Simpson, E. R. and Waterman, M. R. (1986), *J. Biol. Chem.* 261, 2475–2482.

Zuber, M. X., Simpson, E. R. and Waterman, M. R. (1986), *Science* 234, 1258–1262.

---

What is claimed is:

1. A DNA segment comprising a gene encoding a fusion protein, said DNA segment being substantially free from total genomic DNA, the fusion protein having a eukaryotic cytochrome P450 hybrid enzyme domain and a cytochrome P450 reductase domain, wherein said gene comprises, in order of transcription, a promoter capable of effecting expression of the encoded fusion protein in a compatible bacterial cell positioned in operable linkage with a DNA region encoding the fusion protein, a ribosome binding site compatible with a bacterial cell, the DNA encoding the fusion protein, and a transcription terminator, wherein the DNA encoding the amino proximal portion of the fusion protein has been modified to allow bacterial expression of the fusion protein in a biologically active form within a bacterial transformant of the Enterobacteriaceae, wherein said eukaryotic cytochrome P450 hybrid enzyme doman has at its amino terminus the nine amino acids Met Ala Leu Leu Leu Ala Val Phe Leu.

2. The DNA segment of claim 1, wherein the encoded cytochrome P450 hybrid enzyme domain is selected from the group of cytochrome P450 families consisting of the I, II, III, IV, VI, XIA, XIB, XVII, XIX, XXI, and XXVI families.

3. The DNA segment of claim 2, wherein the encoded cytochrome P450 hybrid enzyme domain is a domain capable of metabolizing a substrate selected from the group consisting of the steroid, fatty acid, lipid, prostaglandin, leukotriene, vitamin, and xenobiotic metabolizing enzymes.

4. The DNA segment of claim 3, wherein the encode cytochrome P450 hybrid enzyme domain comprises a 17α-hydroxylase.

5. The DNA segment of claim 3, wherein the encoded cytochrome P450 hybrid enzyme domain comprises 1A2, 3A4, 1A1 or 2C8.

6. The DNA segment of claim 1, wherein the encoded cytochrome P450 hybrid enzyme domain comprises a cytochrome P450 enzyme hybrid in which the first nine amino acid residues are derived from bovine cytochrome P450 17α-hydroxylase.

7. The DNA segment of claim 1, wherein the sequence of codons encoding the first nine amino residues of the cytochrome P450 hybrid enzyme hybrid is ATG

GCT CTG TTA TTA GCA GTT TTT CTG (SEQ ID NO:2).

8. The DNA segment of claim 1, wherein the encoded cytochrome P450 enzyme domain comprises a cytochrome P450 enzyme hybrid comprising 1A2, 3A4, 1A1, or 2C8.

9. The DNA segment of claim 1, wherein the encoded reductase domain comprises a mammalian reductase.

10. The DNA segment of claim 1, wherein the encoded reductase domain comprises rat liver reductase.

11. The DNA segment of claim 1, wherein the encoded reductase domain comprises a human reductase.

12. The DNA segment of claim 1, wherein the encoded reductase domain comprises the reductase domain of P450BM3.

13. The DNA segment of claim 1, wherein the encoded fusion protein domain comprises a linker region positioned between the encoded P450 domain and the encoded reductase domain.

14. The DNA segment of claim 13, wherein the encoded linker region is further defined as comprising about 1-300 amino acids.

15. The DNA segment of claim 13 wherein the encoded linker region comprises Ser, Thr, and/or Gly.

16. The linker region of claim 15, further defined as comprising one Asp, Lys, Glu, Asn, Ala or Pro residue.

17. The linker region of claim 15, further defined as comprising unlimited Pro residues.

18. The linker region of claim 15, further defined as comprising only one Asp, Lys, Glu, Asu or Ala residue and unlimited Pro residues.

19. The DNA segment of claim 13, wherein the linker region comprises a SerThr dipeptide linker.

20. The DNA segment of claim 13, wherein the encoded linker region domain comprises a restriction site.

21. The DNA segment of claim 20, wherein the encoded restriction site is a Sal 1 restriction site.

22. The DNA segment of claim 1, wherein the amino terminus of the reductase is truncated.

23. The DNA segment of claim 22, wherein the amino terminus of the encoded reductase domain is truncated such that the hydrophobic anchoring domain of the carboxy terminus is removed.

24. The DNA segment of claim 22, wherein the encoded amino terminus of the reductase domain is truncated immediately following a trypsin sensitive site.

25. The DNA segment of claim 1, wherein the encoded reductase domain encodes rat P450 reductase in which the amino terminus is truncated immediately following the encoded trypsin sensitive site at Lys56.

26. The DNA segment of claim 1, wherein the encoded carboxyterminus of the P450 hybrid enzyme domain is fused to the encoded aminoterminus of the reductase domain.

27. The DNA segment of claim 1, further defined as a plasmid.

28. The DNA segment of claim 1, wherein the promoter comprises a tac, lac, lac UV5 tac, trc, $\lambda P_L$, T7 or T3 promoter.

29. The DNA segment of claim 1, wherein the ribosome binding site comprises an E. coli, $\lambda$, T7 or T3 ribosome binding site.

30. The DNA segment of claim 29, wherein the ribosome binding site comprises a T7 gene 10, or E. coli lac a, lac z, trp A, trp B, trp C, trp D, trp E, trp L, trp R, or trp S ribosome binding site.

31. The DNA segment of claim 1, wherein the ribosome binding site and spacer region comprise 5'- AG GAGGTCAT - 3'(SEQ ID NO:3).

32. The DNA segment of claim 1, wherein the terminator comprises a trp, $rrn^B$, or T7 terminator.

33. The DNA segment of claim 1, wherein the terminator comprises an RNase III cleavage site.

34. A purified fusion protein comprising a eukaryotic cytochrome P450 enzyme domain and a cytochrome P450 hybrid reductase domain, said protein being free of normal eukaryotic glycosylation, wherein said eukaryotic cytochrome P450 hybrid enzyme doman has at its amino terminus the nine amino acids Met Ala Leu Leu Leu Ala Val Phe Leu.

35. A transformed bacterial cell comprising the DNA segment of claim 1.

36. The bacterial cell of claim 35, the cell being further defined as being capable of expression of the DNA segment of claim 1.

37. The bacterial cell of claim 35, wherein the bacterial cell comprises a member of the gram negative family Enterobacteriaceae.

38. The bacterial cell of claim 37, wherein the bacterial cell comprises E. coli.

39. A method for obtaining a DNA segment comprising a gene encoding a fusion protein as claimed in claim 1, the method comprising:
(a) obtaining a DNA segment which comprises an encoded eukaryotic cytochrome P450 hybrid enzyme domain;
(b) obtaining a DNA segment which comprises an encoded reductase domain;
(c) fusing the DNA segment comprising the encoded P450 hybrid enzyme domain to the DNA segment comprising the encoded reductase domain, thereby creating a segment comprising an encoded fusion protein; and
(d) modifying the DNA segment comprising an encoded fusion protein so as to operatively combine the DNA segment comprising the encoded fusion protein with a bacterially compatible ribosome binding site, transcription terminator and promotor.

40. A method for the production of a fusion protein comprising preparing a bacterial cell in accordance with claims 35-38 and culturing said cell under conditions appropriate to effectuate expression of the fusion protein.

41. The method of claim 40, wherein the fusion protein produced by a bacterial cell prepared in accordance with claims 37 or 38 is further defined as being biologically active.

42. The method of claim 40, further comprising collecting the fusion protein so produced.

43. A method for preparing a bacterial cell comprising a DNA segment encoding a fusion protein, the method comprising the steps of:
(a) obtaining a DNA segment which comprises an encoded eukaryotic cytochrome P450 hybrid enzyme domain;
(b) obtaining a DNA segment which comprises an encoded reductase domain wherein said eukaryotic cytochrome P450 hybrid enzyme doman has at its amino terminus the nine amino acids Met Ala Leu Leu Leu Ala Val Phe Leu gene;
(c) fusing the DNA segment comprising the encoded P450 enzyme domain to the DNA segment comprising the encoded reductase domain thereby creating a segment comprising an encoded fusion protein;

(d) transforming bacteria with the segment comprising an encoded fusion protein, forming transformant colonies; and (e) selecting a transformant colony with the segment comprising an encoded fusion protein.

44. The method of claim 43, wherein the DNA segment encoding the fusion protein is modified by combining it with a bacterial expression cassette.

45. A method for obtaining bacterial expression of any DNA segment claimed in claim 1, the method comprising:

(a) obtaining a DNA segment which comprises an encoded eukaryotic cytochrome P450 hybrid enzyme domain wherein said eukaryotic cytochrome P450 hybrid enzyme domain has at its amino terminus the nine amino acids Met Ala Leu Leu Leu AlaVal Phe Leu;

(b) obtaining a DNA segment which comprises an encoded cytochrome P450 hybrid reductase domain;

(c) fusing the DNA segment comprising the encoded P450 enzyme domain to the DNA segment comprising the encoded cytochrome P450 reductase domain, thereby creating a segment comprising an encoded fusion protein;

(d) modifying the DNA segment comprising the encoded fusion protein to form a bacterial expression unit, said bacterial expression unit comprising, in order of transcription, a promotor placed in operable linkage with the DNA region encoding the fusion protein, said promotor capable of effecting expression of the encoded fusion protein in a compatible bacterial cell, a ribosome binding site compatible with a bacterial cell, the DNA region encoding the fusion protein, and a transcription terminator, wherein the DNA region encoding an amino proximal portion of the fusion protein has been modified to allow expression of the fusion protein in a biologically active form within a bacterial transformant of the Enterobacteriaceae;

(e) transforming a bacteria selected from the group Enterobacteriaceae with the bacterial expression unit, forming transformant colonies;

(f) selecting a transformant colony which expresses the fusion protein encoded in the bacterial expression unit in a biologically active manner; and (g) culturing the selected transformant under conditions effective to express the fusion protein.

46. A method for obtaining bacterial expression of any DNA segment claimed in claim 1, the method comprising the steps of:

(a) obtaining a DNA segment which comprises an encoded eukaryotic cytochrome P450 hybrid enzyme domain wherein said eukaryotic cytochrome P450 hybrid enzyme domain has as its amino terminus the nine amino acids Met Ala Leu Leu Leu Ala Val Phe Leu;

(b) obtaining a DNA segment which comprises an encoded cytochrome P450 reductase domain;

(c) fusing the DNA segment comprising the encoded P450 enzyme domain to the DNA segment comprising the encoded cytochrome P450 reductase domain, thereby creating a DNA segment comprising an encoded fusion protein;

(d) combining the DNA segment comprising the encoded fusion protein with a DNA segment encoding the first nine amino acid residues from bovine cytochrome P450 17α-hydroxylase, thereby modifying the DNA region encoding an amino proximal portion of the fusion protein to allow expression of the fusion protein in a biologically active form within a bacterial transformant of the Enterobacteriaceae;

(e) modifying the combined DNA to form a bacterial expression unit, said bacterial expression unit comprising, in order of transcription, a promotor placed in operable linkage with the DNA region encoding the fusion protein, said promotor capable of effecting transcription of the encoded fusion protein in a compatible bacterial cell, a ribosome binding site compatible with a bacterial cell, the DNA region encoding the fusion protein, and a transcription terminator;

(f) transforming a bacteria of the group Enterobacteriaceae with the bacterial expression unit, forming transformant colonies;

(g) selecting a transformant colony which expresses the encoded fusion protein in a biologically active manner; and (h) culturing the selected transformant under conditions effective to express the fusion protein.

47. The method of claim 46 wherein the cytochrome P450 enzyme utilized is a cytochrome P450 enzyme hybrid comprising 1A2, 3A4, A1 or 2C8.

48. The method of claim 46, wherein the DNA segment encoding the fusion protein is modified by combining it with a bacterial expression cassette.

49. A recombinant vector comprising the DNA segment of claim 1.

* * * * *

UNITED STATES PATENT AND TRADEMARK OFFICE
CERTIFICATE OF CORRECTION

PATENT NO. : 5,420,027

DATED : May 30, 1995

INVENTOR(S) : Charles W. Fisher, Henry J. Barnes, Ronald W. Estabrook

It is certified that error appears in the above-identified patent and that said Letters Patent is hereby corrected as shown below:

```
Claim 43, col. 58, ln. 65 after "val Phe Leu" delete --gene--

Claim 46, col. 60, ln. 12 after "P450" insert --hybrid--
therefor.
```

Signed and Sealed this

Twenty-ninth Day of August, 1995

Attest:

BRUCE LEHMAN

Attesting Officer      Commissioner of Patents and Trademarks

SEQUENCE LISTING ( 1 ) GENERAL INFORMATION:

( i i i ) NUMBER OF SEQUENCES: 34

( 2 ) INFORMATION FOR SEQ ID NO: 1:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( x i ) SEQUENCE DESCRIPTION: SEQ ID NO: 1:

Met Ala Leu Leu Leu Ala Val Phe Leu
1               5

( 2 ) INFORMATION FOR SEQ ID NO: 2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO: 2:
ATGGCTCTGT TATTAGCAGT TTTTCTG ( 2 ) INFORMATION FOR SEQ ID NO: 3:

( i ) SEQUENCE CHARACTERISTICS:
( A ) LENGTH: 10 base pairs (B) TYPE: nucleic acid
(C) STRANDEDNESS: single
(D) TOPOLOGY: linear (xi) SEQUENCE DESCRIPTION: SEQ ID NO: 3:
AGGAGGTCAT (2) INFORMATION FOR SEQ ID NO: 4:

(i) SEQUENCE CHARACTERISTICS:
(A) LENGTH: 8 amino acid residues
(B) TYPE: amino acid
(C) STRANDEDNESS: single
(D) TOPOLOGY: linear (xi) SEQUENCE DESCRIPTION: SEQ ID NO: 4:
Met Trp Leu Leu Leu Ala Val Phe
1               5

(2) INFORMATION FOR SEQ ID NO: 5:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 5:
ATGTGGCTGC TCCTGGCTGT CTTT                                      24

(2) INFORMATION FOR SEQ ID NO: 6:

(i) SEQUENCE CHARACTERISTICS:
(A) LENGTH: 39 amino acid residues
(B) TYPE: amino acid
(C) STRANDEDNESS: single
(D) TOPOLOGY: linear (xi) SEQUENCE DESCRIPTION: SEQ ID NO: 6:
Met Val Leu Glu Met Leu Asn Pro Ile His Tyr Asn Ile Thr Ser Ile
1               5                   10                  15
Val Pro Glu Ala Met Pro Ala Ala Thr Met Pro Val Leu Leu Thr
                20                  25                  30
Gly Leu Phe Leu Leu Val Trp
        35

(2) INFORMATION FOR SEQ ID NO: 7:

(i) SEQUENCE CHARACTERISTICS:
(A) LENGTH: 19 amino acid residues
(B) TYPE: amino acid
(C) STRANDEDNESS: single
(D) TOPOLOGY: linear (xi) SEQUENCE DESCRIPTION: SEQ ID NO: 7:
Met Val Leu Ala Gly Leu Leu Leu Leu Leu Thr Leu Leu Ser Gly
1               5                   10                  15
Ala His Leu (2) INFORMATION FOR SEQ ID NO: 8:

(i) SEQUENCE CHARACTERISTICS:
(A) LENGTH: 22 amino acid residues
(B) TYPE: amino acid
(C) STRANDEDNESS: single
(D) TOPOLOGY: linear (xi) SEQUENCE DESCRIPTION: SEQ ID NO: 8:
Met Leu Phe Pro Ile Ser Met Ser Ala Thr Glu Phe Leu Leu Ala Ser
1               5                   10                  15
Val Ile Phe Cys Leu Val
                20

(2) INFORMATION FOR SEQ ID NO: 9:

(i) SEQUENCE CHARACTERISTICS:
(A) LENGTH: 24 amino acid residues
(B) TYPE: amino acid
(C) STRANDEDNESS: single
(D) TOPOLOGY: linear (xi) SEQUENCE DESCRIPTION: SEQ ID NO: 9:

```
Met Ala Leu Ser Gln Ser Val Pro Phe Ser Ala Thr Glu Leu Leu Leu
1               5                   10                  15
Ala Ser Ala Ile Phe Cys Leu Val
                20
```

(2) INFORMATION FOR SEQ ID NO: 10:

(i) SEQUENCE CHARACTERISTICS:
        (A) LENGTH: 19 amino acid residues
        (B) TYPE: amino acid
        (C) STRANDEDNESS: single
        (D) TOPOLOGY: linear (xi) SEQUENCE DESCRIPTION: SEQ ID NO: 10:
```
Met Glu Pro Phe Val Val Leu Val Leu Cys Leu Ser Phe Met Leu Leu
1               5                   10                  15
Phe Ser Leu
```

(2) INFORMATION FOR SEQ ID NO: 11:

(i) SEQUENCE CHARACTERISTICS:
        (A) LENGTH: 23 amino acid residues
        (B) TYPE: amino acid
        (C) STRANDEDNESS: single
        (D) TOPOLOGY: linear (xi) SEQUENCE DESCRIPTION: SEQ ID NO: 11:
```
Met Ala Leu Ile Pro Asp Leu Ala Met Asp Thr Trp Leu Leu Leu Ala
1               5                   10                  15
Val Ser Leu Val Leu Leu Tyr
                20
```

(2) INFORMATION FOR SEQ ID NO: 12:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (xi) SEQUENCE DESCRIPTION: SEQ ID NO: 12:
```
Met Trp Leu Leu Leu Ala Val Phe Leu
1               5
```

(2) INFORMATION FOR SEQ ID NO: 13:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (xi) SEQUENCE DESCRIPTION: SEQ ID NO: 13:
```
Gly Ser Thr Pro Ser Thr Ile Gln Thr
1               5
```

(2) INFORMATION FOR SEQ ID NO: 14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 14:
```
GGTAGCACCC CGTCGACTAT CCAAACA                                    26
```

(2) INFORMATION FOR SEQ ID NO: 15:

(i) SEQUENCE CHARACTERISTICS:
        (A) LENGTH: 9 amino acid residues
        (B) TYPE: amino acid
        (C) STRANDEDNESS: single
        (D) TOPOLOGY: linear (xi) SEQUENCE DESCRIPTION: SEQ ID NO: 15:
```
Lys Lys Leu His Ser Thr Ile Gln Thr
1               5
```

(2) INFORMATION FOR SEQ ID NO: 16:

(i) SEQUENCE CHARACTERISTICS:

( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO: 16:

GGTAGCACCC CCTCGACTAT CCAAACA 27

( 2 ) INFORMATION FOR SEQ ID NO: 17:

( i ) SEQUENCE CHARACTERISTICS:
( A ) LENGTH: 14 amino acid residues
( B ) TYPE: amino acid
( C ) STRANDEDNESS: single
( D ) TOPOLOGY: linear ( x i ) SEQUENCE DESCRIPTION: SEQ ID NO: 17:

Met Ala Leu Leu Leu Ala Val Phe Leu Gly Leu Leu Leu Leu
 1               5                  10

( 2 ) INFORMATION FOR SEQ ID NO: 18:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( x i ) SEQUENCE DESCRIPTION: SEQ ID NO: 18:

ATGGCTCTGT TATTAGCAGT TTTTCTGGTT CTGCTGCTGG TC 42

( 2 ) INFORMATION FOR SEQ ID NO: 19:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO: 19:

ATCGATGCTT AGGAGGTCAT ATG 23

( 2 ) INFORMATION FOR SEQ ID NO: 20:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( x i ) SEQUENCE DESCRIPTION: SEQ ID NO: 20:

ATGGTAGCAA GGGGGCTTCC CCTGCGCTCA GCCCTGGTCA AAGCCTGCCC ACCCATC 5

( 2 ) INFORMATION FOR SEQ ID NO: 21:

( i ) SEQUENCE CHARACTERISTICS:
( A ) LENGTH: 19 amino acid residues
( B ) TYPE: amino acid
( C ) STRANDEDNESS: single
( D ) TOPOLOGY: linear ( x i ) SEQUENCE DESCRIPTION: SEQ ID NO: 21:

Met Val Ala Arg Gly Leu Pro Leu Arg Ser Ala Leu Val Lys Ala Cys
 1               5                  10                  15
Pro Pro Ile ( 2 ) INFORMATION FOR SEQ ID NO: 22:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( x i ) SEQUENCE DESCRIPTION: SEQ ID NO: 22:

ATGGTCTCCA CAAAGACCCC TCGCCCCTAC AGTGAGATCC CCTCCCCTGG TGACAAT 57

( 2 ) INFORMATION FOR SEQ ID NO: 23:

( i ) SEQUENCE CHARACTERISTICS:
( A ) LENGTH: 19 amino acid residues
( B ) TYPE: amino acid ( C ) STRANDEDNESS: single
( D ) TOPOLOGY: linear ( x i ) SEQUENCE DESCRIPTION: SEQ ID NO: 23:

Met Val Ser Thr Lys Thr Pro Arg Pro Tyr Ser Glu Ile Pro Ser Pro
1               5                   10                  15
Gly Asp Asn ( 2 ) INFORMATION FOR SEQ ID NO: 24:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:
ATGGCTCTCA TCCCAGACTT GGCCATGGAA ACCTGGCTTC TCCTGGCTGT CAGCCTG    57

( 2 ) INFORMATION FOR SEQ ID NO: 25:

( i ) SEQUENCE CHARACTERISTICS:
        ( A ) LENGTH: 19 amino acid residues
        ( B ) TYPE: amino acid
        ( C ) STRANDEDNESS: single
        ( D ) TOPOLOGY: linear ( x i ) SEQUENCE DESCRIPTION: SEQ ID NO: 25:

Met Ala Leu Ile Pro Asp Leu Ala Met Glu Thr Trp Leu Leu Leu Ala
1               5                   10                  15
Val Ser Leu ( 2 ) INFORMATION FOR SEQ ID NO: 26:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 26:
ATGGCTCTTA TTCCGGATCT GGCTATGGAA ACCTGGCTTC TCCTGGCTGT CAGCCTG    57

( 2 ) INFORMATION FOR SEQ ID NO: 27:

( i ) SEQUENCE CHARACTERISTICS:
        ( A ) LENGTH: 16 amino acid residues
        ( B ) TYPE: amino acid
        ( C ) STRANDEDNESS: single
        ( D ) TOPOLOGY: linear ( x i ) SEQUENCE DESCRIPTION: SEQ ID NO: 27:
Ile Pro Asp Leu Ala Met Glu Thr Trp Leu Leu Leu Ala Val Ser Leu
1               5                   10                  15

( 2 ) INFORMATION FOR SEQ ID NO: 28:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:
ATGGCTCTGT TATTAGCAGT TTTTCTGGTG CTCCTCTATC TATATGGAAC CCATTCA    57

( 2 ) INFORMATION FOR SEQ ID NO: 29:

( i ) SEQUENCE CHARACTERISTICS:
        ( A ) LENGTH: 19 amino acid residues
        ( B ) TYPE: amino acid
        ( C ) STRANDEDNESS: single
        ( D ) TOPOLOGY: linear ( x i ) SEQUENCE DESCRIPTION: SEQ ID NO: 29:

Met Ala Leu Leu Leu Ala Val Phe Leu Val Leu Leu Tyr Leu Tyr Gly
1               5                   10                  15
Thr His Ser ( 2 ) INFORMATION FOR SEQ ID NO: 30:

( i ) SEQUENCE CHARACTERISTICS:

(A) LENGTH: 42 base pairs
(B) TYPE: nucleic acid
(C) STRANDEDNESS: single
(D) TOPOLOGY: linear (xi) SEQUENCE DESCRIPTION: SEQ ID NO: 30:
ATGGCTCTGT TATTAGCAGT TTTCTGTTC TGCCTGGTAT TC 42

(2) INFORMATION FOR SEQ ID NO: 31:

(i) SEQUENCE CHARACTERISTICS:
(A) LENGTH: 14 amino acid residues
(B) TYPE: amino acid
(C) STRANDEDNESS: single
(D) TOPOLOGY: linear (xi) SEQUENCE DESCRIPTION: SEQ ID NO: 31:
Met Ala Leu Leu Leu Ala Val Phe Leu Phe Cys Leu Val Phe
1              5                   10

(2) INFORMATION FOR SEQ ID NO: 32:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO: 32:
ATGGCTCTGT TATTAGCAGT TTTCTGTTC TGTCTGGTAT TC 42

(2) INFORMATION FOR SEQ ID NO: 33:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO: 33:
ATGGCTCTGT TATTAGCAGT TTTCTTCTC TTTCACTCT GG 42

(2) INFORMATION FOR SEQ ID NO: 34:

(i) SEQUENCE CHARACTERISTICS:
(A) LENGTH: 14 amino acid residues
(B) TYPE: amino acid
(C) STRANDEDNESS: single
(D) TOPOLOGY: linear (xi) SEQUENCE DESCRIPTION: SEQ ID NO: 34:
Met Ala Leu Leu Leu Ala Val Phe Leu Leu Leu Ser Leu Trp
1              5                   10